United States Patent
Hensley et al.

(10) Patent No.: US 10,882,831 B2
(45) Date of Patent: *Jan. 5, 2021

(54) COMPOSITIONS USEFUL IN THERAPY OF AUTOPHAGY-RELATED PATHOLOGIES, AND METHODS OF MAKING AND USING THE SAME

(71) Applicants: The University of Toledo, Toledo, OH (US); Washington State University, Pullman, WA (US)

(72) Inventors: Kenneth Hensley, Toledo, OH (US); Travis Denton, Toledo, OH (US)

(73) Assignees: The University of Toledo, Toledo, OH (US); Washington State University, Pullman, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/487,960

(22) PCT Filed: Feb. 16, 2018

(86) PCT No.: PCT/US2018/018488
§ 371 (c)(1),
(2) Date: Aug. 22, 2019

(87) PCT Pub. No.: WO2018/156429
PCT Pub. Date: Aug. 30, 2018

(65) Prior Publication Data
US 2020/0010435 A1    Jan. 9, 2020

Related U.S. Application Data

(60) Provisional application No. 62/462,660, filed on Feb. 23, 2017.

(51) Int. Cl.
*C07D 279/12*    (2006.01)

(52) U.S. Cl.
CPC .................. *C07D 279/12* (2013.01)

(58) Field of Classification Search
CPC ..... C07D 279/12; C07F 9/6544; Y02P 20/582
See application file for complete search history.

(56) References Cited

U.S. PATENT DOCUMENTS

2019/0040091 A1*    2/2019    Hensley .................... A61P 9/10

OTHER PUBLICATIONS

Berges, et al, A spontaneous sulfoxide dehydration, J. of Org. Chem. 50(3), 413-15 (1985). (Year: 1985).*

* cited by examiner

*Primary Examiner* — Erich A Leeser
(74) *Attorney, Agent, or Firm* — MacMillan, Sobanski & Todd, LLC

(57) ABSTRACT

Lanthionine ketimine phosphonate (LK-P), lanthionine ketimine ester phosphonate (LKE-P), other lanthionine ketimine, lanthionine ketimine phosphonate, and lanthionine ketimine ester derivatives, and methods of making and using the same, are described.

29 Claims, 32 Drawing Sheets
(17 of 32 Drawing Sheet(s) Filed in Color)

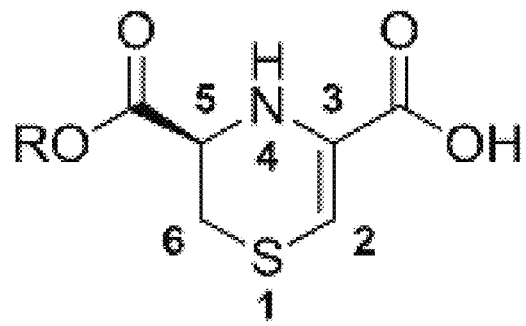
PRIOR ART FIG. 1
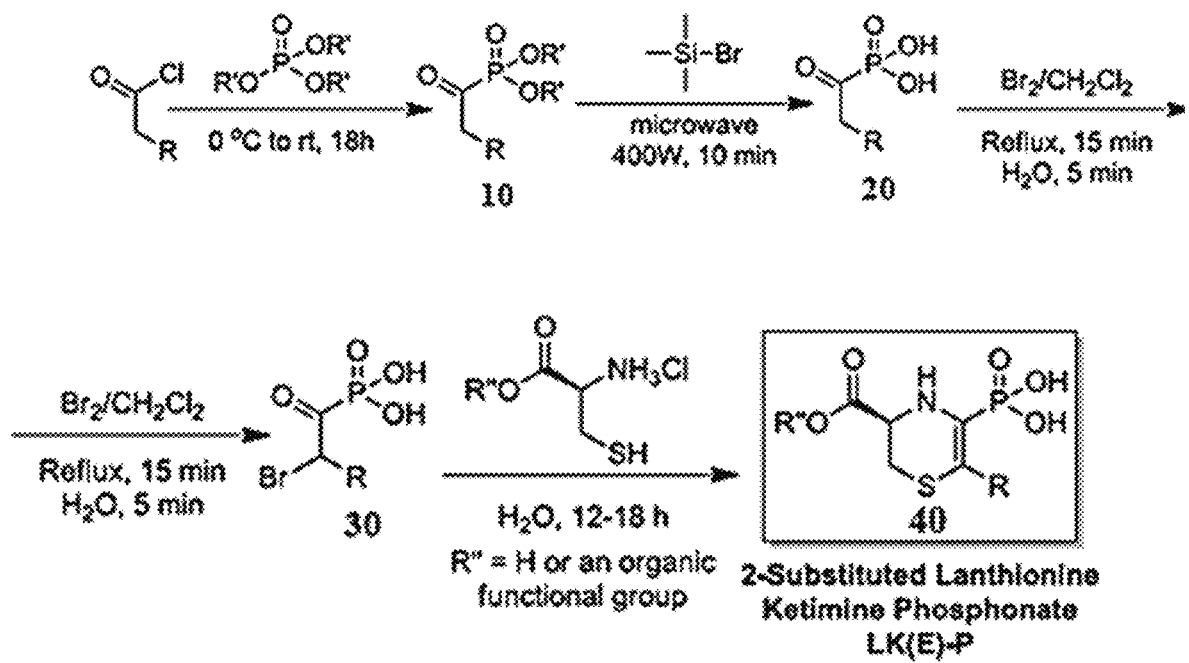
FIG. 2A – Scheme 1A

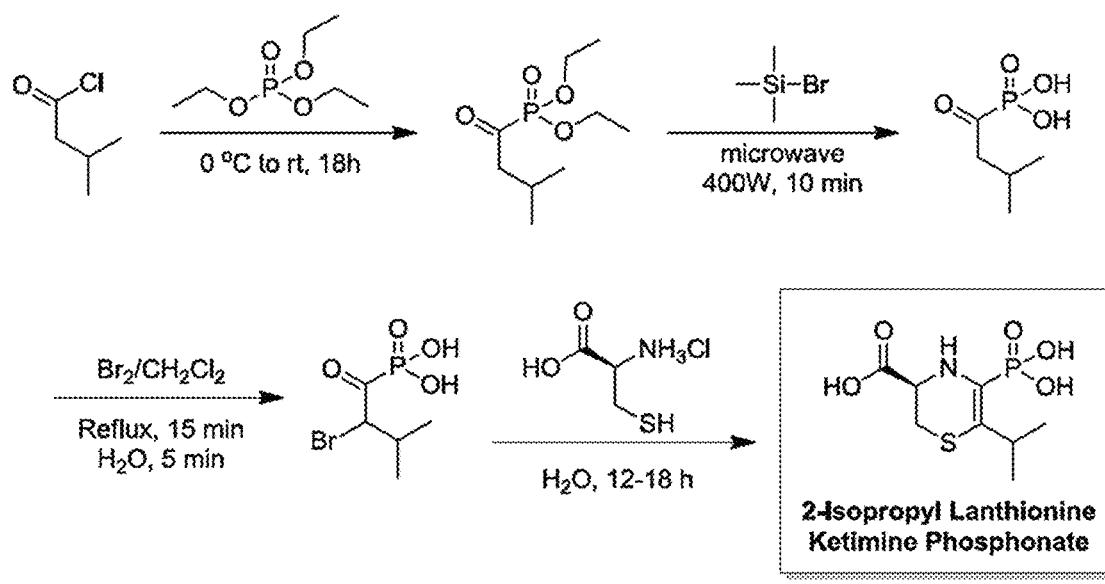
FIG. 2B – Scheme 1B
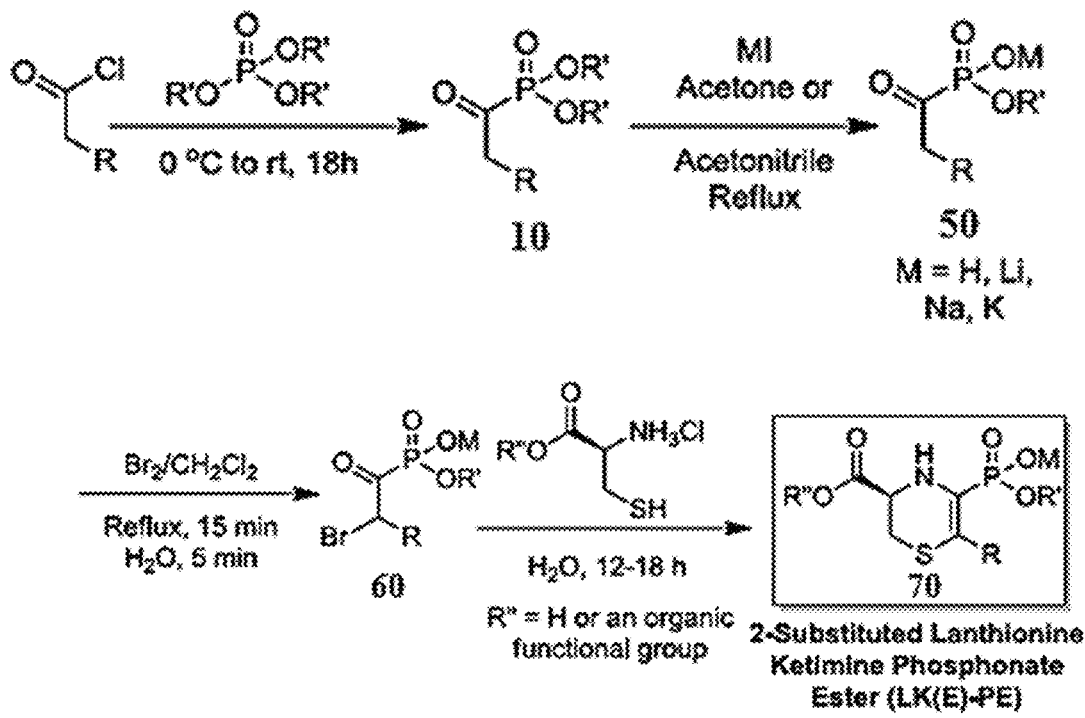
FIG. 3A – Scheme 2A

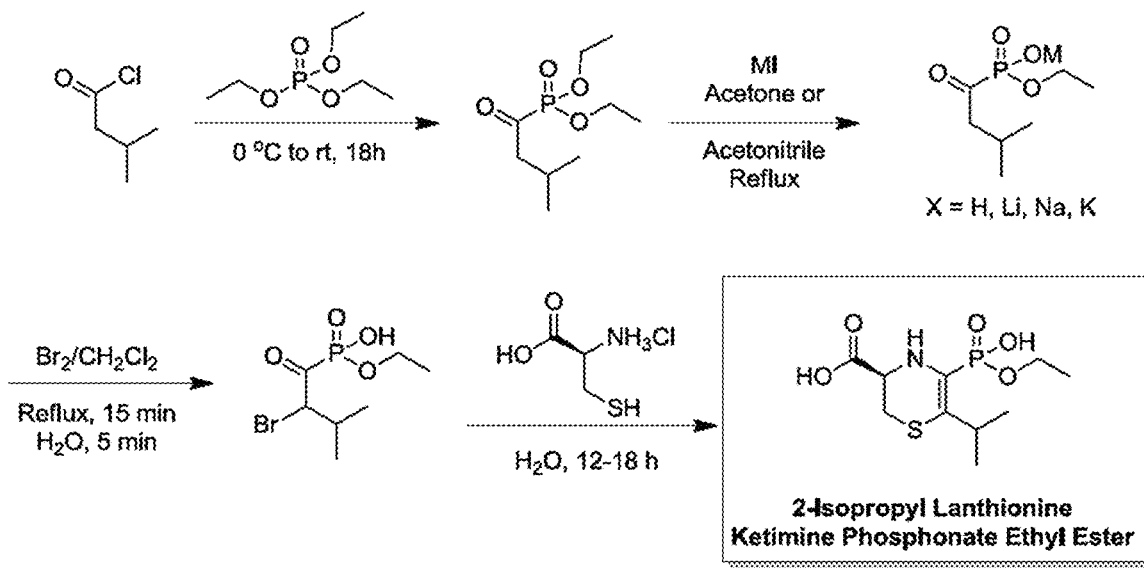
FIG. 3B – Scheme 2B
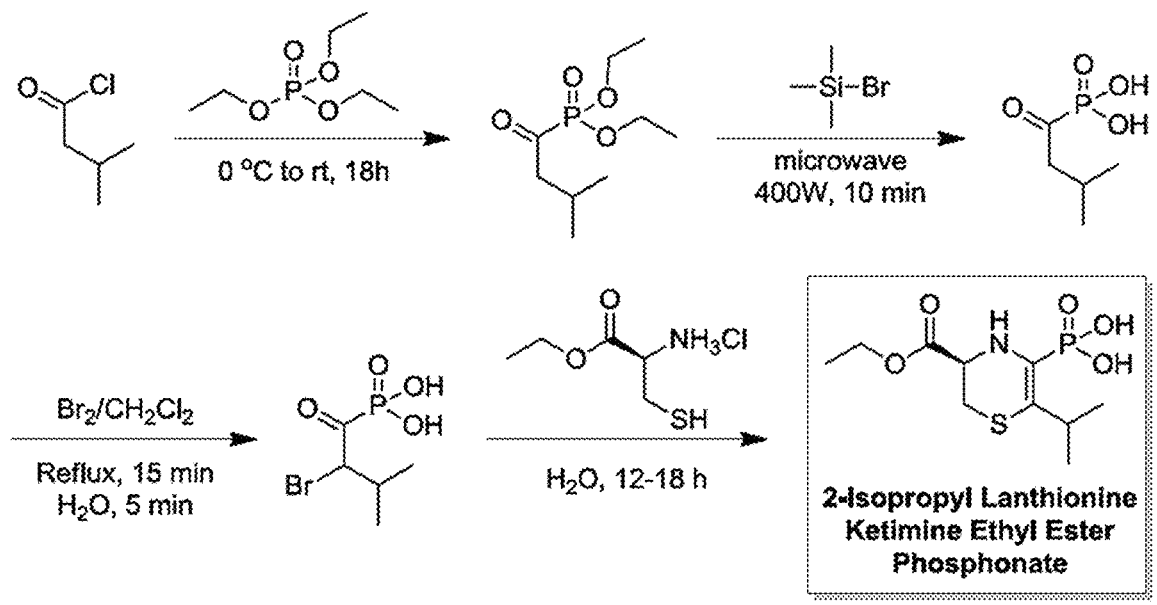
FIG. 4 – Scheme 3

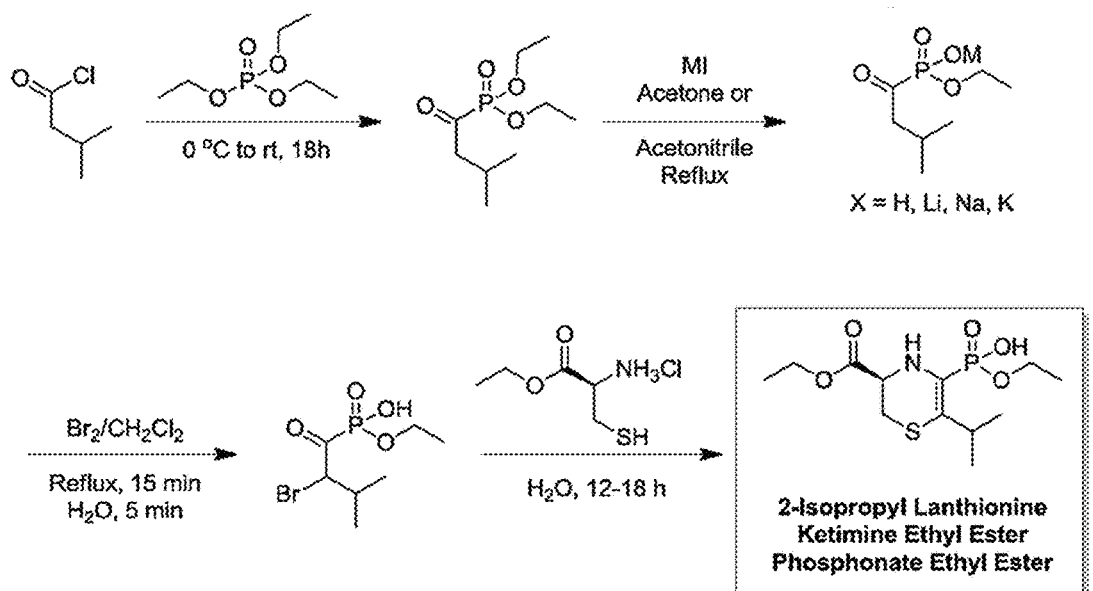
FIG. 5 – Scheme 4
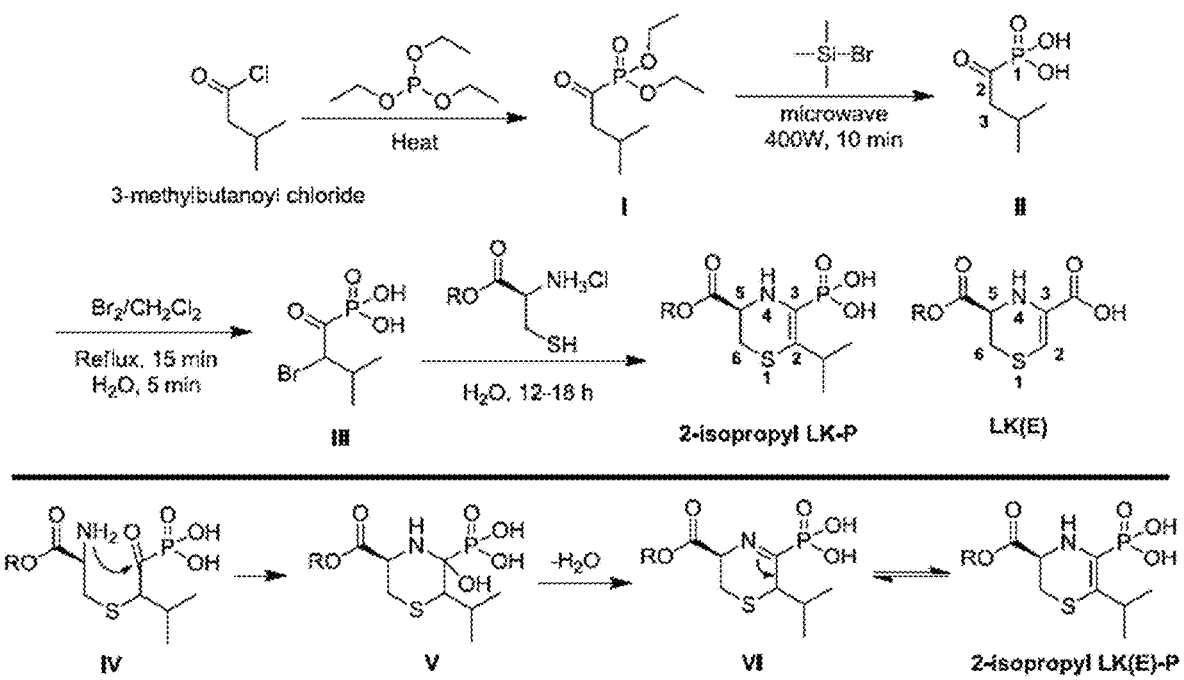
FIG. 6 – Scheme 5

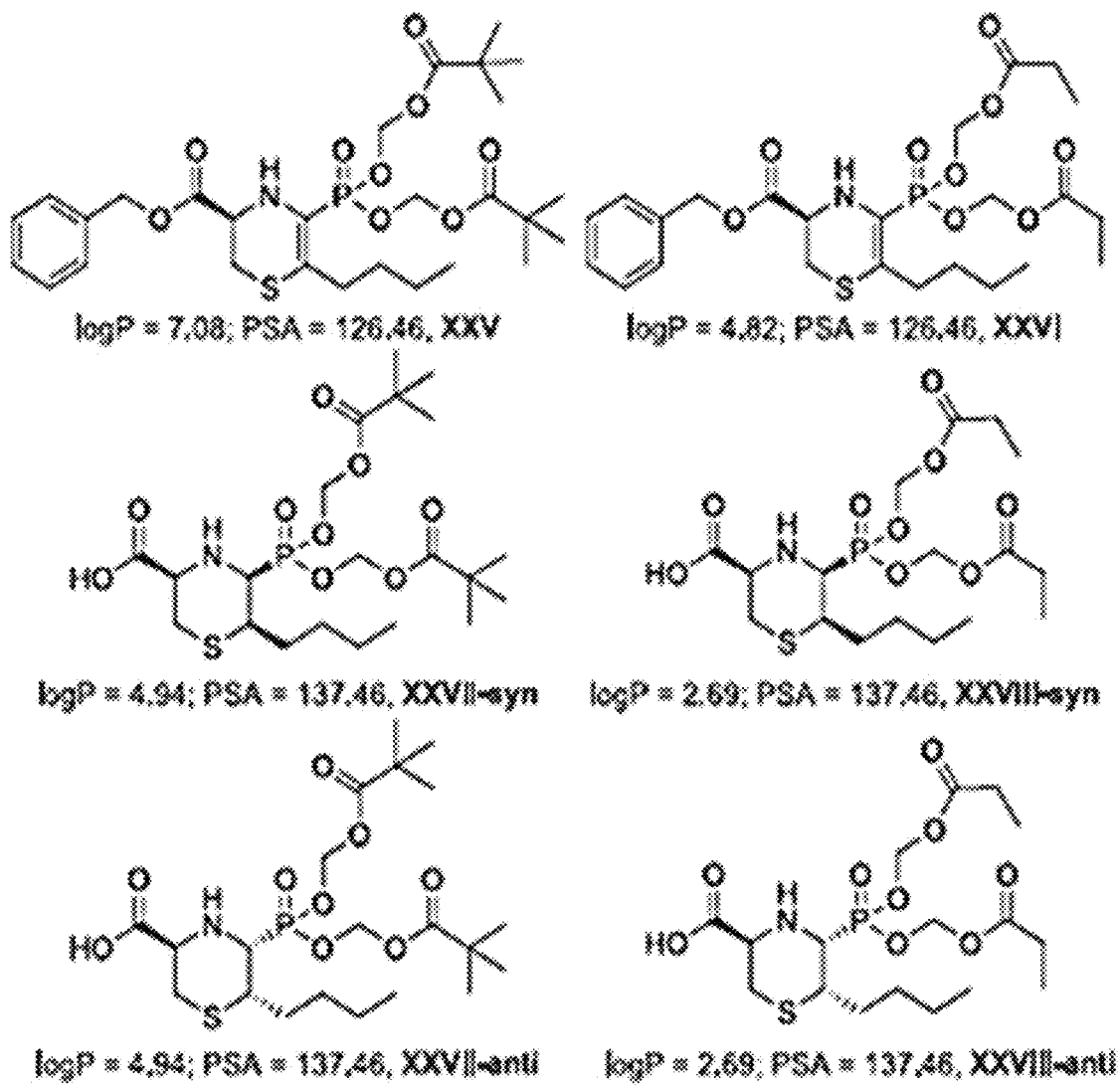
FIG. 11 CONT.
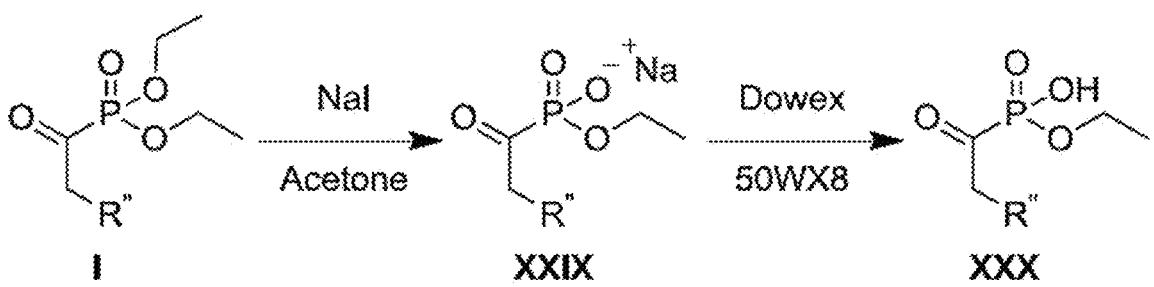
FIG. 12 – Scheme 6

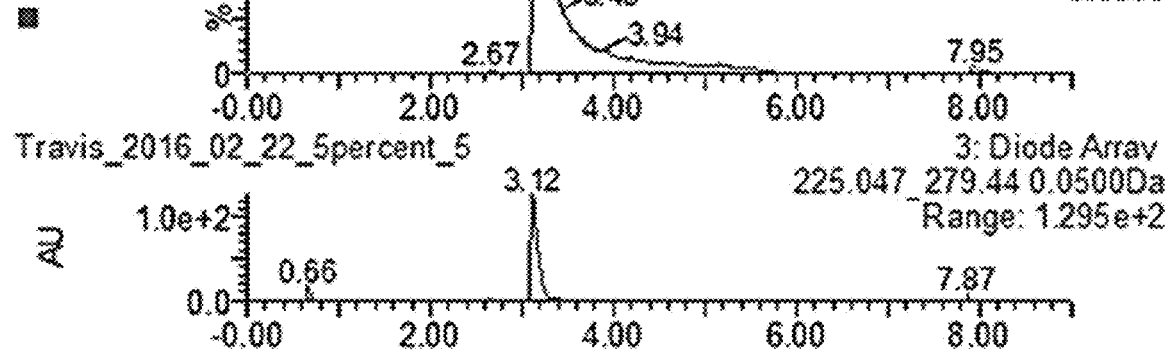
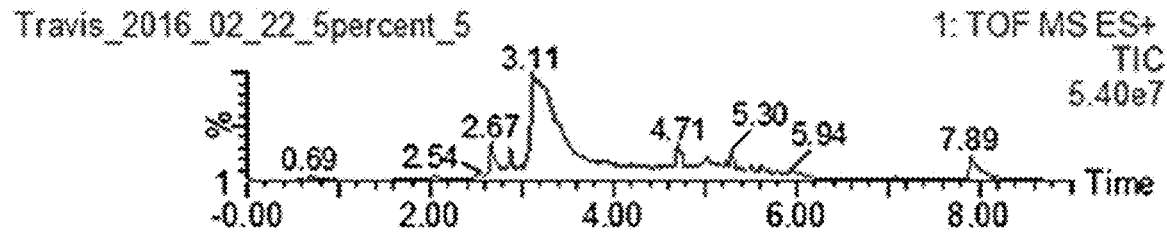
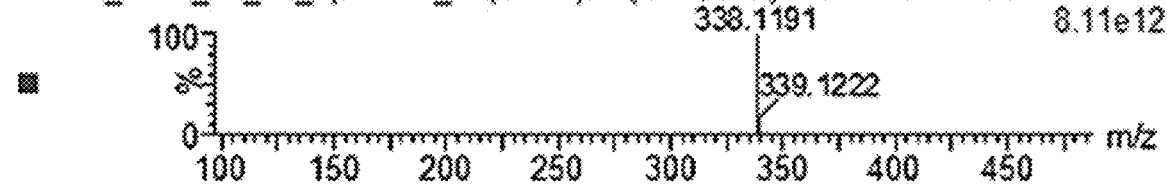
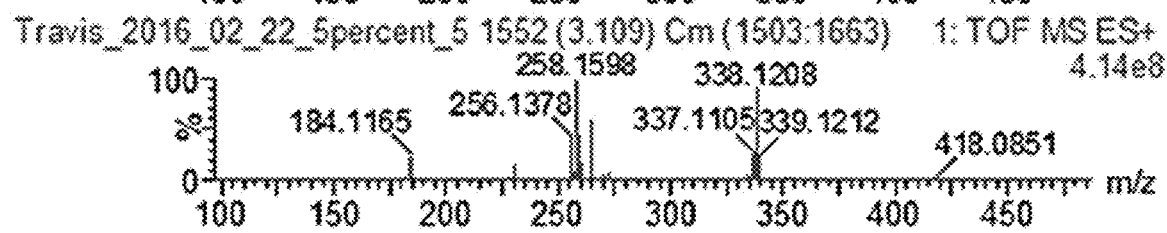
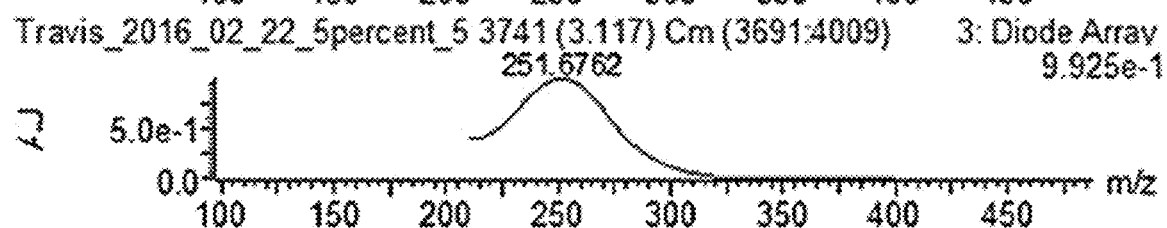
FIG. 20

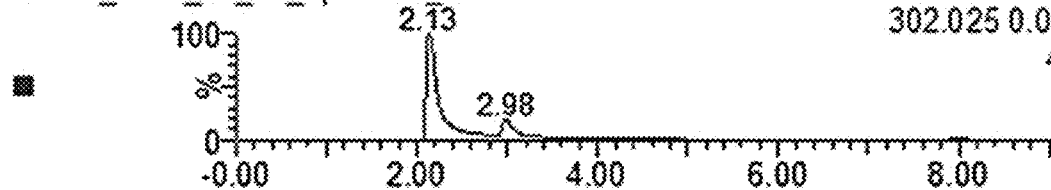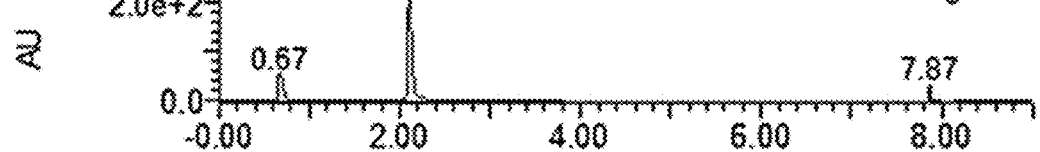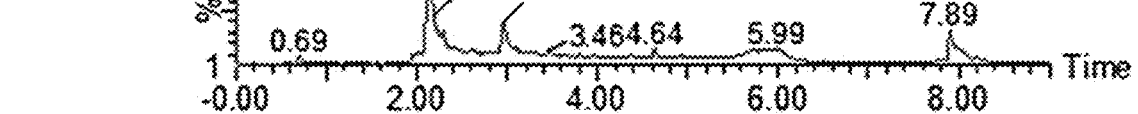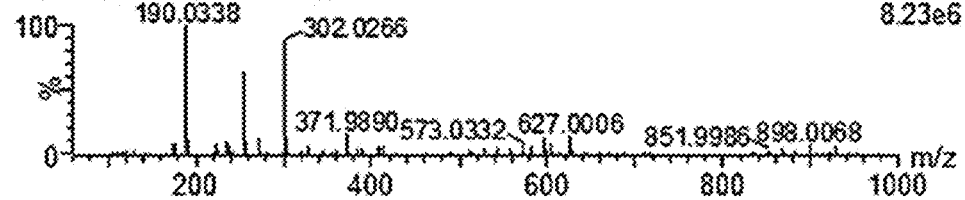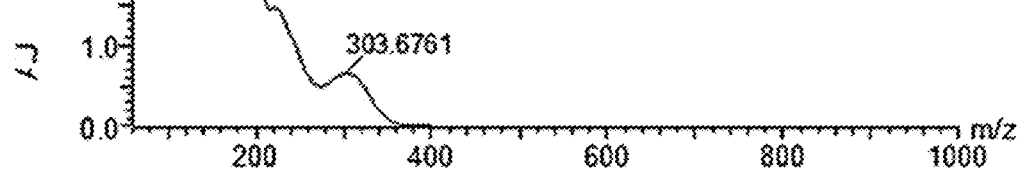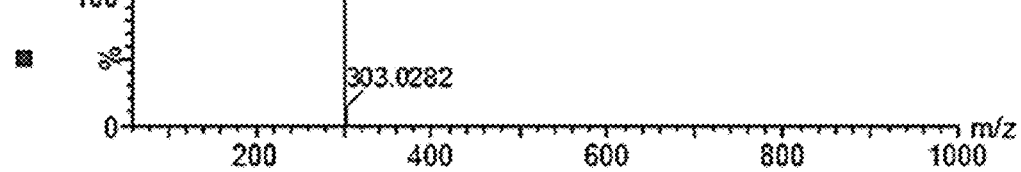
FIG. 24

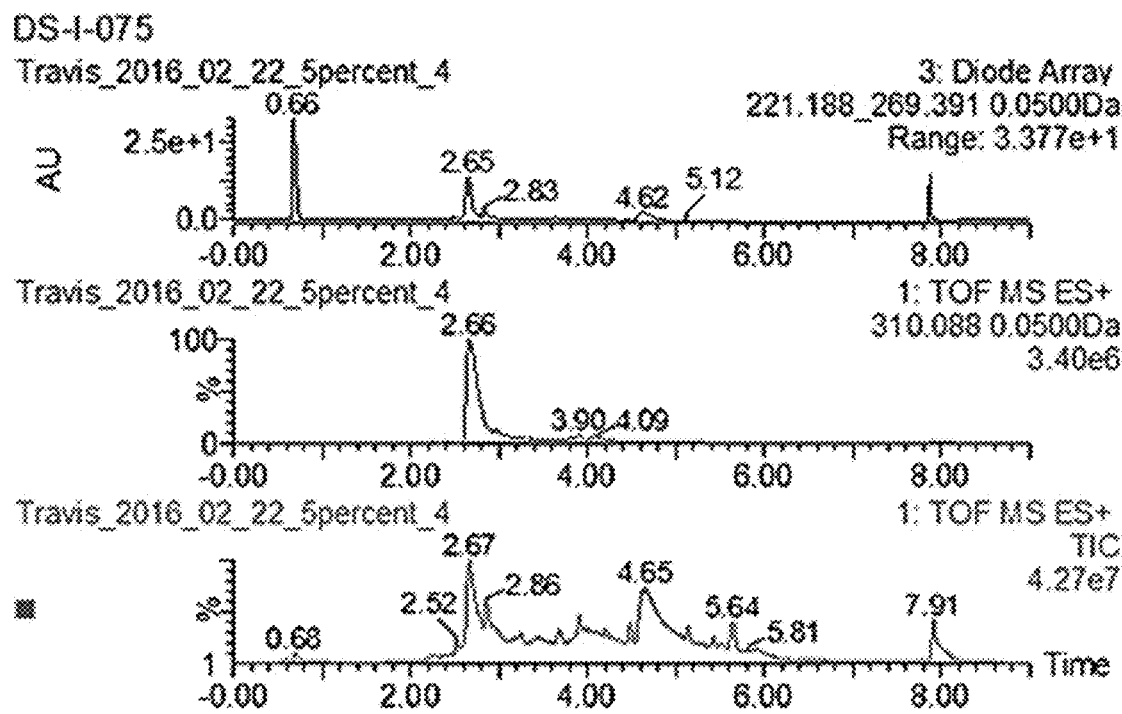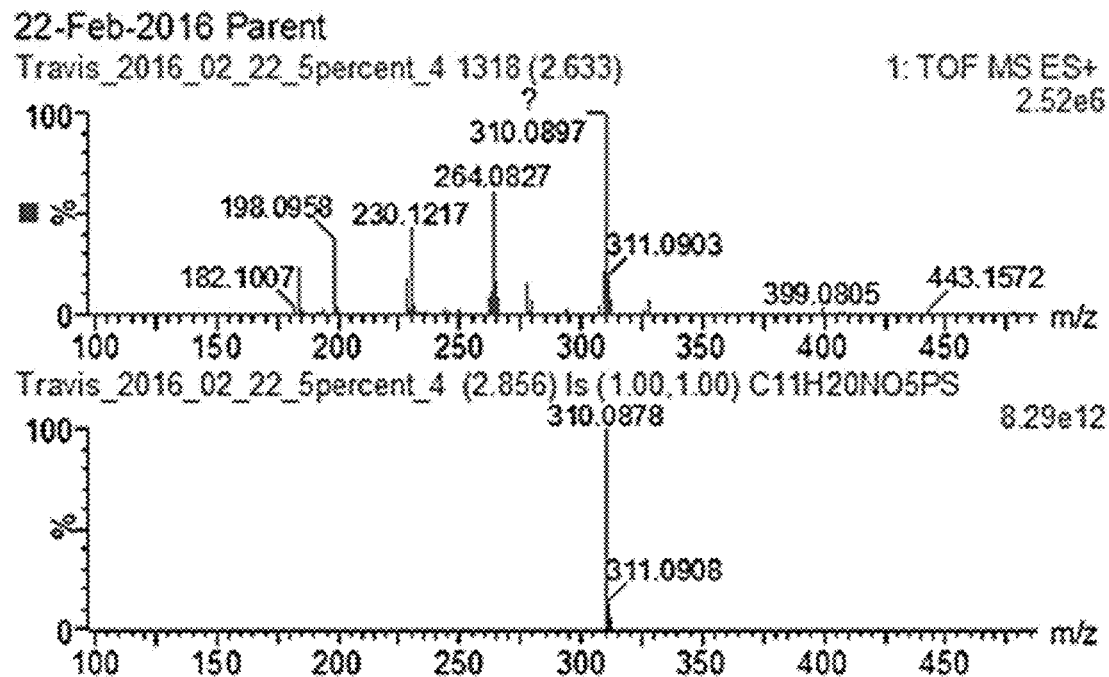
FIG. 26

COMPOSITIONS USEFUL IN THERAPY OF AUTOPHAGY-RELATED PATHOLOGIES, AND METHODS OF MAKING AND USING THE SAME

CROSS-REFERENCE TO RELATED APPLICATIONS

This application is a national stage application filed under 35 U.S.C. § 371 of international application PCT/US2018/018488, filed under the authority of the Patent Cooperation Treaty on Feb. 16, 2018, which claims priority to U.S. Provisional Application No. 62/462,660 filed under 35 U.S.C. § 111(b) on Feb. 23, 2017, the entire disclosure of which is expressly incorporated herein by reference for all purposes.

STATEMENT REGARDING FEDERALLY SPONSORED RESEARCH

This invention was made with no government support. The government has no rights in this invention.

BACKGROUND OF THE INVENTION

Autophagy is a sophisticated set of catabolic programs for selectively recycling macromolecules, protein complexes, and whole organelles. Macro-autophagy (hereafter referred to as "autophagy") involves envelopment and recycling of autophagic substrates in double-lumen vesicles and delivery to the lysosome for digestion. Autophagy occurs at low levels in most cells but is greatly accelerated when nutrients are scarce or cells need to undertake structural remodeling, in instances such as ridding themselves of protein aggregates or during developmental transitions. As such, autophagy counter-balances anabolic processes of biosynthesis and replication. Autophagy helps defend against metabolic stress, maintain homeostasis, arbitrate cell fate decisions, and safeguard genomic stability. Hence, deficient autophagy has been associated with over 100 diseases, and experimental enhancement of autophagy (mostly through molecular strategies that are not yet clinically translatable) often mitigates disease severity in nonhuman models, ranging from cancers to muscular dystrophies to amyotrophic lateral sclerosis (ALS). Autophagy dysfunction is a common underlying cellular pathology amongst many neurodegenerative conditions. In fact, autophagy has been invoked to explain why caloric restriction is the only reliable means of extending lifespan in every species yet investigated. Despite autophagy's fundamental importance in biology, there remains a lack of small molecule therapeutics targeting this fundamental cellular process.

Autophagy is a highly complex, subtly regulated phenomenon in which over 60 proteins have been implicated as regulatory or structural players. This inherent system complexity has raised major barriers to understanding how autophagy works and, in particular, how this complicated system might be therapeutically manipulated. Autophagy is still poorly understood. Currently, the main ways to promote autophagy, short of genetic manipulation, are by starvation or with rapamycin derivatives (rapalogs). These approaches have empowered scientific discoveries but they are not practical means to treat chronic disease. Although rapalogs have proven invaluable in managing transplant rejection, hyperplastic diseases, and cancers, they carry substantial chronic toxicity and have low brain penetrance.

As reported in U.S. Pat. No. 7,683,055, the sulfur amino acid metabolite lanthionine ketimine (LK) and its brain penetrable ethyl ester, LKE (PRIOR ART FIG. 1), represent a way to activate autophagy. LKE shows superb activity in pre-clinical rodent studies of human diseases including: ALS-LKE increases lifespan and slows decline of motor function in the SOD1$^{G93A}$ mouse model of ALS; Alzheimer's disease (AD) LKE decreases amyloid burden inside neurons and in plaques, decreases phospho-tau accumulation, decreases microglial activation, and slows cognitive decline in the 3xTg-AD mouse model of (AD); stroke LKE decreases infarct volume and improves functional recovery after permanent middle cerebral artery occlusion (pMCAO); and glioma—LKE slows growth of C6 glioma tumor after xenograft into rat cortices. LKE has been shown, in cell systems and *C. elegans*, to act as: an anti-neuroinflammatory agent by decreasing microglial response to inflammatory cytokines; an amyloid reducing agent, by decreasing production of native Aβ(1-40) in SHSYSY neurons; a classical antioxidant, by protecting cells against $H_2O_2$ or t-butyl hydroperoxide; an anti-excitotoxin, by protecting neurons from glutamate toxicity; an activator of neurotrophic activity, by potentiating growth factor-dependent neurite growth in a CRMP2-dependent fashion; and as an axonal transport enhancer, by potentiating anterograde trafficking and delivery of synaptic proteins to the distal axon. LKE has been documented to reduce symptoms of neuropathology in a variety of preclinical models of diseases ranging from ALS to (AD), traumatic brain injury, stroke, multiple sclerosis, and glioma. The effects of LK largely result from the compound's ability to engage collapsing response mediator protein-2 (CRMP2; DPYSL2) pathways to alter localization of the protein mTOR (mammalian target of rapamycin) and thus promote beneficial autophagy.

U.S. Pat. No. 7,683,055 describes potent neuroprotective properties inherent in certain synthetic derivatives of the natural mammalian brain sulfur amino acid metabolite lanthionine ketimine. The compounds disclosed in U.S. Pat. No. 7,683,055 are cyclic compounds comprising a thioether component and an enamine component, with carboxylic acid side groups (or esters or amides, thereof) located adjacent to (vicinal to) the amine.

It would be advantageous to discover compounds having functionality similar to, or better than, that of the compounds disclosed in U.S. Pat. No. 7,683,055.

SUMMARY OF THE INVENTION

Provided is a compound comprising Formula F:

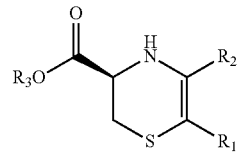

Formula F wherein $R_1$ is hydrogen or substituted or unsubstituted alkyl, aryl, alkoxy, ester, alkenylamino, alkynylamino, aryloxy, aralkoxy, acyloxy, alkylamino, arylamino, aralkylamino, or amido; $R_2$ is selected from the group consisting of COOH, COOR$_4$, PO(OH)$_2$, PO(OR$_4$)$_2$, POOR$_4$OR$_5$, and POOR$_4$OX, wherein $R_4$ and $R_5$ are each independently alkyl groups, and X is hydrogen, a group I metal, a halide, or substituted or unsubstituted alkyl, alkoxy, ester, alkenylamino, alkynylamino, aryloxy, aralkoxy, acyloxy, alkylamino, arylamino, aralkylamino, or amido; and $R_3$ is hydrogen or substituted or unsubstituted alkyl, aryl, alkoxy, ester, alkenylamino, alkynylamino, aryloxy, aralkoxy, acyloxy, alkylamino, arylamino, aralkylamino, or amido; provided, however, that when $R_1$ is hydrogen and $R_2$ is COOH, $R_3$ is not ethyl or hydrogen. Also provided are salts, stereoisomers, racemates, hydrates, solvates, polymorphs, and alkene reduction products of Formula F. In certain embodiments, $R_2$ is COOH or $COOR_4$, and $R_3$ is hydrogen. In certain embodiments, $R_2$ is COOH or $COOR_4$, and $R_3$ is alkyl. In certain embodiments, $R_1$ is alkyl.

In certain embodiments, the compound comprises a substituent to facilitate transport of the compound through the blood brain barrier.

Provided is a compound comprising Formula D:

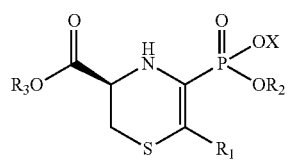

Formula D wherein $R_1$ is hydrogen or substituted or unsubstituted alkyl, aryl, alkoxy, ester, alkenylamino, alkynylamino, aryloxy, aralkoxy, acyloxy, alkylamino, arylamino, aralkylamino, or amido; $R_2$ is hydrogen or substituted or unsubstituted alkyl, alkoxy, ester, alkenylamino, alkynylamino, aryloxy, aralkoxy, acyloxy, alkylamino, arylamino, aralkylamino, or amido; $R_3$ is hydrogen or substituted or unsubstituted alkyl, aryl, alkoxy, ester, alkenylamino, alkynylamino, aryloxy, aralkoxy, acyloxy, alkylamino, arylamino, aralkylamino, or amido; and X is is hydrogen, a group I metal, a halide, or substituted or unsubstituted alkyl, alkoxy, ester, alkenylamino, alkynylamino, aryloxy, aralkoxy, acyloxy, alkylamino, arylamino, aralkylamino, or amido. Also provided are salts, stereoisomers, racemates, solvates, hydrates, polymorphs, and alkene reduction products of Formula D.

In certain embodiments, each of $R_2$ and $R_3$ is independently selected from the group consisting of hydrogen, or heteroatom substituted or unsubstituted versions of $C_1$-$C_{15}$-alkoxy, $C_2$-$C_{15}$-alkenylamino, $C_2$-$C_{15}$-alkynylamino, $C_1$-$C_{15}$-aryloxy, $C_2$-$C_{15}$-aralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_1$-$C_{15}$-aralkylamino, $C_2$-$C_{15}$-aralkylamino, or $C_1$-$C_{15}$-amido. In certain embodiments, $R_3$ is selected from the group consisting of hydrogen, ethyl, phenyl, and isopropyl ester. In certain embodiments, X is selected from the group consisting of hydrogen and substituted or unsubstituted alkyl, alkoxy, ester, alkenylamino, alkynylamino, aryloxy, aralkoxy, acyloxy, alkylamino, arylamino, aralkylamino, or amido. In certain embodiments, $R_2$ is selected from the group consisting of hydrogen and an ester. In certain embodiments, both X and $R_2$ are alkoxy.

In certain embodiments, the compound comprises Formula B:

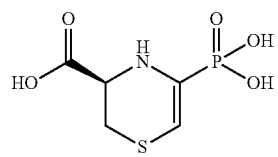

Formula B

In certain embodiments, the compound comprises Formula IX:

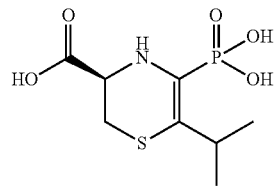

Formula IX

In certain embodiments, the compound comprises Formula X:

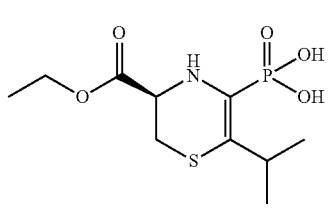

Formula X

In certain embodiments, the compound comprises Formula XIII:

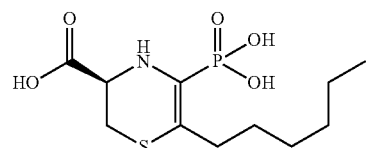

Formula XIII

In certain embodiments, the compound comprises Formula XIV:

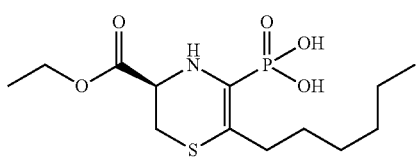

Formula XIV

In certain embodiments, the compound comprises Formula XV:

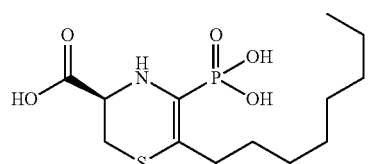

Formula XV

In certain embodiments, the compound comprises Formula XVI:

Formula XVI

In certain embodiments, the compound comprises Formula XI:

Formula XI

In certain embodiments, the compound comprises Formula XVIII:

Formula XVIII

In certain embodiments, the compound comprises Formula XIX:

Formula XIX

In certain embodiments, the compound comprises Formula XX:

Formula XX

In certain embodiments, the compound comprises Formula XXI:

Formula XXI

In certain embodiments, the compound comprises Formula XXII:

Formula XXII

In certain embodiments, the compound comprises Formula XXIII

Formula XXIII

In certain embodiments, the compound comprises Formula XXIV:

Formula XXIV

In certain embodiments, the compound comprises Formula XXV:

Formula XXV

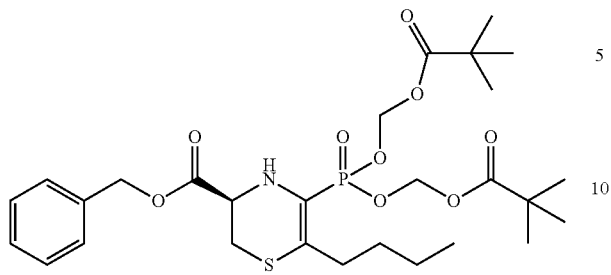

In certain embodiments, the compound comprises Formula XXVI:

Formula XXVI

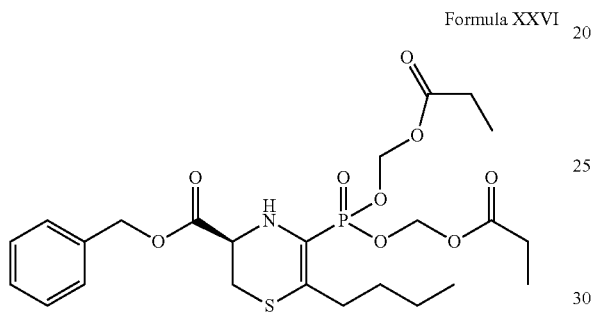

In certain embodiments, the compound comprises an alkene reduction product having Formula XXVII, in either syn or anti configuration:

Formula XXVII-syn

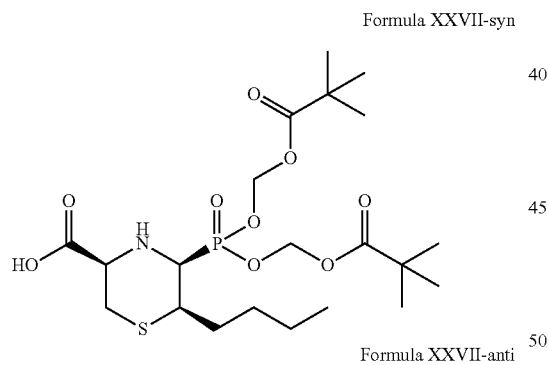

Formula XXVII-anti

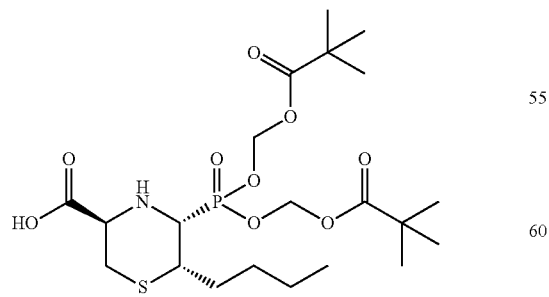

In certain embodiments, the compound comprises an alkene reduction product having Formula XXVIII, in either syn or anti configuration:

Formula XXVIII-syn

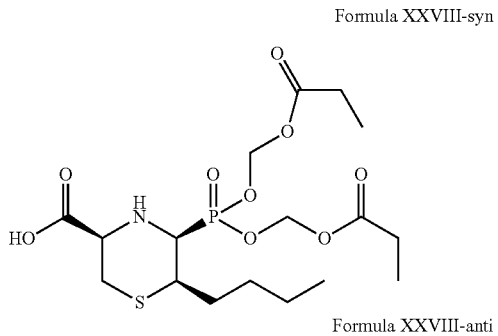

Formula XXVIII-anti

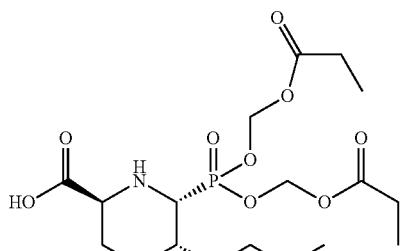

In certain embodiments, the compound comprises Formula XXIX:

Formula XXIX

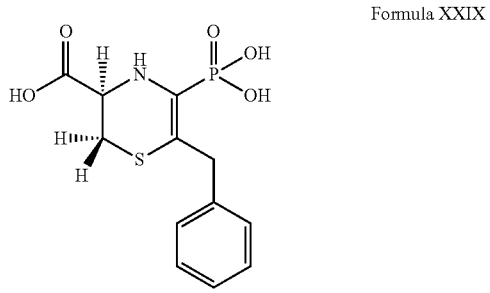

In certain embodiments, the compound comprises Formula XXX:

Formula XXX

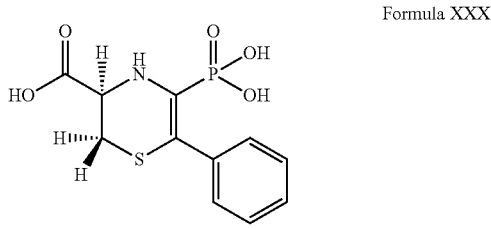

Also provided are compounds comprising Formula E:

Formula E

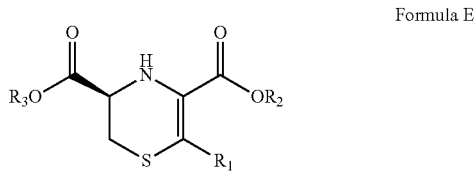

where $R_1$ is alkyl or aryl; $R_2$ is hydrogen or substituted or unsubstituted alkyl, alkoxy, ester, alkenylamino, alkynylamino, aryloxy, aralkoxy, acyloxy, alkylamino, arylamino, aralkylamino, or amido; and $R_3$ is a substituted or unsubstituted alkyl, alkoxy, ester, alkenylamino, alkynylamino, aryloxy, aralkoxy, acyloxy, alkylamino, arylamino, aralkylamino, or amido. Also provided are salts, stereoisomers, racemates, hydrates, solvates, polymorphs, and alkene reduction products of Formula E.

In certain embodiments, $R_1$ comprises methyl, ethyl, propyl, butyl, benzyl, or phenyl. In certain embodiments, $R_2$ is hydrogen. In particular embodiments, $R_3$ is hydrogen. In certain embodiments, $R_2$ is selected from the group consisting of hydrogen, or heteroatom substituted or unsubstituted versions of $C_1$-$C_{15}$-alkoxy, $C_2$-$C_{15}$-alkenylamino, $C_2$-$C_{15}$-alkynylamino, $C_1$-$C_{15}$-aryloxy, $C_2$-$C_{15}$-aralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_1$-$C_{15}$-arylamino, $C_2$-$C_{15}$-aralkylamino, or $C_1$-$C_{15}$-amido; and $R_3$ is selected from the group consisting of heteroatom substituted or unsubstituted versions of $C_1$-$C_{15}$-alkoxy, $C_2$-$C_{15}$-alkenylamino, $C_2$-$C_{15}$-alkynylamino, $C_1$-$C_{15}$-aryloxy, $C_2$-$C_{15}$-aralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_1$-$C_{15}$-arylamino, $C_2$-$C_{15}$-aralkylamino, or $C_1$-$C_{15}$-amido. In certain embodiments, $R_3$ is selected from the group consisting of methyl, ethyl, phenyl, and isopropyl. In certain embodiments, $R_2$ is selected from the group consisting of hydrogen and an alkyl group. In certain embodiments, $R_1$ is methyl, ethyl, or isopropyl, $R_2$ is hydrogen, and $R_3$ is alkyl. In particular embodiments, $R_3$ is methyl or ethyl.

In certain embodiments, the compound consists essentially of 2-methyl-LKE:

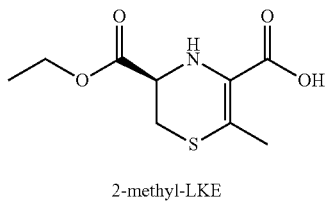

2-methyl-LKE

In certain embodiments, the compound consists essentially of 2-ethyl-LKE:

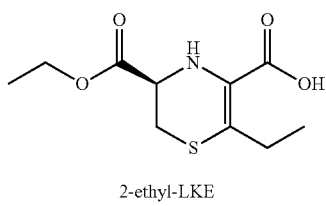 [SMILES: CCOC(=O)[C@@H]1CSC(CC)=C(C(=O)O)N1]

2-ethyl-LKE

Also provided is a compound referred to as 2-isopropyl-AECK-P:

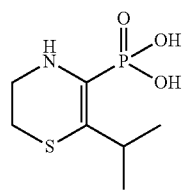

2-isopropyl-AECK-P

Also provided are salts, stereoisomers, racemates, hydrates, prodrugs, polymorphs, and alkene reduction products of 2-isopropyl-AECK-P.

Further provided is a pharmaceutical composition comprising an effective amount of a compound herein, and a pharmaceutically acceptable carrier, diluent, or adjuvant.

Further provided is a method of treating an autophagy-related disease, the method comprising administering an effective amount of a compound described herein to a subject in need thereof and treating an autophagy-related disease. In certain embodiments, the autophagy-related disease is selected from the group consisting of: ALS, AD, Huntington's disease, Parkinson's disease, stroke, multiple sclerosis, macular degeneration, atherosclerosis, rheumatoid arthritis, inflammatory bowel disease, attention deficit disorder, depression, or generalized anxiety disorder. In certain embodiments, the subject is a human subject.

Further provided is a method reducing damage to a cell resulting from oxidative stress, excitotoxicity, free radical toxicity, or excitatory amino acid toxicity, the method comprising contacting a cell with a compound described herein and reducing damage to the cell, wherein the cell is a neuron, macrophage, or glial cell. In certain embodiments, the cell is selected from the group consisting of astrocytes, microglia, oligodendrocytes, and ependyma. In certain embodiments, the cell is present in a human subject.

Further provided is a method of treating a patient having an inflammatory disease, the method comprising administering a therapeutically effective amount of a compound described herein to a patient having an inflammatory disease to treat the patient. In certain embodiments, the inflammatory disease is rheumatoid arthritis or inflammatory bowel disease.

Further provided is a method of treating a patient having a neurodegenerative disease, the method comprising administering a therapeutically effective amount of a compound described herein to a patient having a neurodegenerative disease to treat the patient. In certain embodiments, the neurodegenerative disease is AD, Huntington's disease, Parkinson's disease, multiple clerosis, or ALS.

Further provided is a method of treating a patient having a pathogenesis involving the excessive production of nitric oxide or prostaglandins, the method comprising administering a therapeutically effective amount of a compound described herein to a patient having a pathogenesis involving the excessive production of nitric oxide or prostaglandins and treating the patient.

Further provided is a method of treating a patient having a disorder characterized by the overexpression of the iNOS or COX-2 gene, the method comprising administering a therapeutically effective amount of a compound described herein to a patient having a disorder characterized by the overexpression of the iNOS or COX-2 gene, and treating the patient.

Further provided is a method of modulating transcription of translation of iNOS or COX-2 genes in a patient, the method comprising administering a therapeutically effective amount of a compound described herein to a patient and modulating transcription of translation of the iNOS or COX-2 gene in the patient.

Further provided is a method of modulating excessive nitric oxide or prostaglandin formation in a patient, the method comprising administering a therapeutically effective amount of a compound described herein to a patient and modulating excessive nitric oxide or prostaglandin formation in the patient.

Further provided is a method of treating a subject for, or being at risk for having, a stroke, the method comprising administering a pharmacologically effective amount of a compound described herein to a subject having, or being at risk for having, a stroke.

Further provided is a method of treating a patient having cancer, the method comprising administering a therapeutically effective amount of a compound described herein to a patient having cancer to treat the patient. In certain embodiments, the cancer is brain, lung, liver, spleen, kidney, lymph node, small intestine, pancreas, blood cell, bone, colon, stomach, endometrium, prostate, testicle, ovary, central nervous system, skin, head and neck, esophagus, or bone marrow.

Further provided is a method for treating neurodegenerative diseases wherein protein delivery to lysosomes is compromised, the method comprising administering an effective amount of a compound described herein to a patient in need thereof and treating a neurodegenerative disease wherein protein delivery to lysosomes is compromised. In certain embodiments, the neurodegenerative disease wherein protein delivery to lysosomes is compromised is selected from the group consisting of Batten disease (neuronal ceroid lipofuscinosis), Niemann-Pick disease, Machado-Joseph disease, spinocerebellar ataxia, Fabry disease, and mucopolysaccharoidosis.

Further provided is a method of determining coverage of health insurance reimbursement or payments, the method comprising denying coverage or reimbursement for a treatment, wherein the treatment comprises a compound described herein.

Further provided is a method of making a compound described herein, the method comprising reacting a phosphonate analogue of 3-halogenated, 3-substituted pyruvate with a cysteine derivative to produce an LK-P, LK-PE, or LKE-P compound. Also provided is the product of the method.

Further provided is a method of making a compound described herein, the method comprising reacting an enolate of a carboxylic acid ester with a dialkyl oxalate to produce a 2-substituted-3-oxosuccinate diester; hydrolyzing and decarboxylating the 2-substituted-3-oxosuccinate diester to produce an α-ketocarboxylic acid; and either (i) directly brominating the α-ketocarboxylic acid followed by reacting with a cysteine derivative to produce a 2-substituted lanthionine ketimine compound, or (ii) esterifying the α-ketocarboxylic acid to produce an α-ketoacid ester, and brominating the α-ketoacid ester followed by reacting with a cysteine derivative to produce a 2-substituted lanthionine ketimine compound. Also provided is the product of the method.

Further provided is a kit for making an autophagy stimulator compound, the kit comprising a first container housing one or more of an α-keto-β-bromophosphonate, an α-keto-β-bromocarboxylic acid, an α-keto-β-bromocarboxylic acid ester, an α-ketocarboxylic acid, or an α-ketoacid ester, and a second container housing a cysteine derivative. In certain embodiments, the kits further includes a pharmaceutically acceptable carrier, diluent, or adjuvant.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

PRIOR ART FIG. 1: Structures of LK and LKE.

FIG. 2A: General synthetic procedure (Scheme 1A) for the preparation for 2-substituted LKE-Ps.

FIG. 2B: Non-limiting example scheme (Scheme 1B) showing the synthetic route of 2-isopropyl lanthionine ketimine phosphonate (2-isopropyl-LK-P).

FIG. 3A: General synthetic procedure (Scheme 2A) for the preparation for 2-substituted LK(E)-PEs.

FIG. 3B: Non-limiting example scheme (Scheme 2B) showing the synthetic route of 2-isopropyl lanthionine ketimine phosphonate ethyl ester (2-isopropyl-LK-PEE).

FIG. 4: Non-limiting example scheme (Scheme 3) showing the synthetic route of 2-isopropyl lanthionine ketimine ethyl ester phosphonate (2-isopropyl-LKE-P).

FIG. 5: Non-limiting example scheme (Scheme 4) showing the synthetic route of 2-isopropyl lanthionine ketimine ethyl ester phosphonate ethyl ester (2-isopropyl-LKE-PEE).

FIG. 6: Scheme 5, showing the synthesis of 2-isopropyl LK(E)-P (top panel), and the partial mechanism of the formation of 2-isopropyl LK(E)-P (bottom panel). Without wishing to be bound by theory, it is believed that the phosphonic acid at position 3 of the 4-aza-1-thia-2-cyclohexene is the bioisosteric replacement for the carboxylate in LK(E) and the isopropyl group at position 2 of the 4-aza-1-thia-2-cyclohexene is providing lipophilicity, in addition to the ester moieties at the 5-position, to increase transport across the blood brain barrier.

FIG. 12: Scheme 6, depicting the preparation of ethyl sodium α-ketophosphonates (XXIX) and monoethyl α-ketophosphonates (XXX).

FIG. 20: UPLC chromatograms, HRMS and UV-Vis spectra of 2-n-hexyl-LKE-P (XIV).

FIG. 24: UPLC chromatograms, HRMS and UV-Vis spectra of 2-phenyl-LK-P (XXX).

FIG. 26: UPLC chromatograms and HRMS spectra of 2-n-hexyl-LK-P (XIII).

FIG. 30A shows the scheme with compound classes numbered, and FIG. 30B shows the scheme with the final products labeled.

FIG. 31 shows a densitometric quantitation of the western blots in FIG. 8 showing the ratio of LC3-II/actin, referenced to control samples without compound or bafilomycin. The test agent 2-isopropyl-LK-P was synthesized as described in the example describing the alternate synthesis of 2-isopropyl-LK-P. These compounds have a tendency to display biphasic efficacy with a relative loss of efficacy at higher concentrations.

FIG. 32A shows Western blots showing the LC3AI→LC3AII conversion with increasing drug concentrations, and a similar pattern of changes to LC3B. FIG. 32B shows a graph illustrating the changing ratio of LC3A-II to actin as a function of drug concentration.

DETAILED DESCRIPTION OF THE INVENTION

Figure 7:
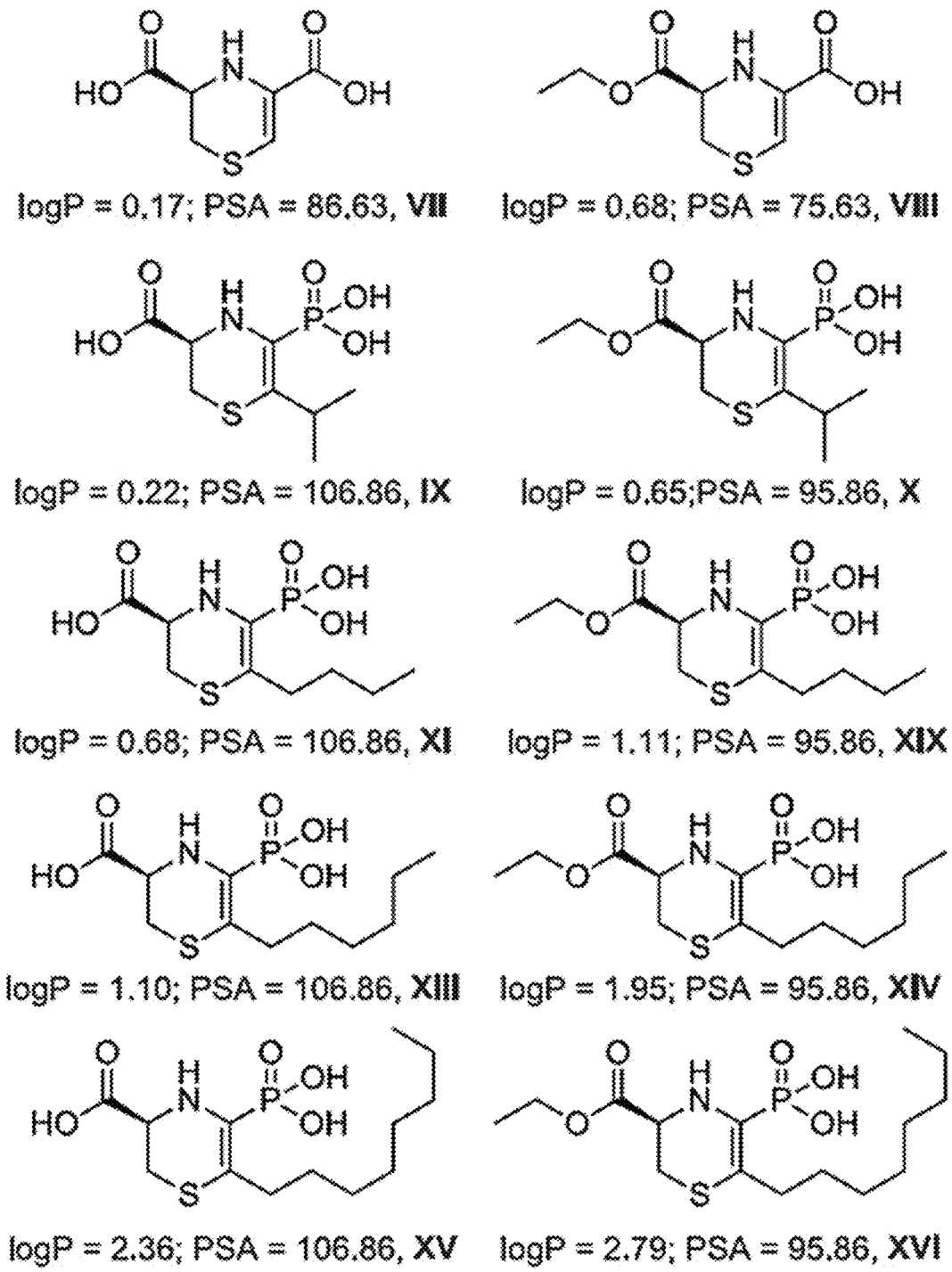
FIG. 7: Structures of select 2-substituted LK(E)-Ps. These compounds are substituted at the 2-position with lipophilic groups. The structures of LK and LKE are also shown, at the top.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Definitions

For convenience, various terms are defined prior to further description of the various embodiments of the present disclosure.

The term "LK-P" refers to lanthionine ketimine phosphonate. The term "LKE-P" refers to lanthionine ketimine ester phosphonate. The term "LK-PE" refers to lanthionine ketimine phosphonate ester. The term "LKE-PE" refers to lanthionine ketimine ester phosphonate ester. The terms "LK(E)-P" and "LKE-P" are used interchangeable herein. Reference to "LK-P compounds" includes both lanthionine ketimine phosphonate (LK-P) and LK-P derivatives or analogues, including LK-PE. Reference to "LKE-P compounds" includes both lanthionine ketimine ester phosphonate (LKE-P) and LKE-P derivatives or analogues, including LKE-PE. Therefore, reference to "LK-P and LKE-P compounds" (or "LK-P or LKE-P compounds") refers to LK-PE, LKE-P, LKE-PE, LK-P, and analogs or derivatives of the same.

For clarity, whenever a specific "LKE" compound is described without further specifying the identity of the ester at the 5-position, the ester is an ethyl ester.

The term "amino" means —NH$_2$. The term "nitro" means —NO$_2$. The term "halo" designates —F, —Cl, —Br, or —I. The term "mercapto" means —SH. The term "cyano" means —CN. The term "silyl" means —SiH$_3$. The term "trimethylsilyl" means —Si(CH$_3$)$_3$. The term "hydroxyl" means —OH.

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

The term "heteroatom-substituted" when used to modify a class of organic radicals (e.g., alkyl, aryl, acyl, etc.), means that one, or more than one, hydrogen atom of that radical has been replaced by a heteroatom, or a heteroatom-containing group. Examples of heteroatoms and heteroatom-containing groups include: hydroxyl, cyano, alkoxy, =O, =S, —NO$_2$, —N(CH$_3$)$_2$, amino, or —SH. Specific heteroatom-substituted organic radicals are defined more fully below.

The term "heteroatom-unsubstituted," when used to modify a class of organic radicals (e.g. alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group heteroatom-substituted. For example, the group —C$_6$H$_4$C≡CH is an example of a heteroatom-unsubstituted aryl group, while —C$_6$H$_4$F is an example of a heteroatom-substituted aryl group. Specific heteroatom-unsubstituted organic radicals are defined more fully below.

The term "heteroatom-unsubstituted $C_n$-alkyl" refers to a radical, having a linear or branched, cyclic or acyclic structure, further having no carbon-carbon double CM triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The term "alkyl" includes straight-chain alkyl groups, branched-chain alkyl groups, cycloalkyl (alicyclic) groups, alkyl heteroatom-substituted cycloalkyl groups, and cycloalkyl heteroatom-substituted alkyl groups. The groups, —$CH_3$, —$CH_2CH_3$, —$CH_2CH_2CH_3$, —$CH(CH_3)_2$, —$CH(CH_2)_2$, —$CH_2CH_2CH_2CH_3$, —$CH(CH_3)CH_2CH_3$, —$CH_2CH(CH_3)_2$, —$C(CH_3)_3$, —$CH_2C(CH_3)_3$, cyclopentyl, and cyclohexyl, are all examples of heteroatom-unsubstituted alkyl groups.

The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CH_3$, —$CH_2OCH_2CH_2CH_3$, —$CH_2OCH(CH_3)_2$, —$CH_2OCH(CH_2)_2$, —$CH_2OCH_2CF_3$, —$CH_2OCOCH_3$, —$CH_2NH_2$, —$CH_2NHCH_3$, —$CH_2N(CH_3)_2$, —$CH_2NHCH_2CH_3$, —$CH_2N(CH_3)CH_2CH_3$, —$CH_2NHCH_2CH_2CH_3$, —$CH_2NHCH(CH_3)_2$, —$CH_2NHCH(CH_2)_2$, —$CH_2N(CH_2CH_3)_2$, —$CH_2CH_2F$, —$CH_2CH_2Cl$, —$CH_2CH_2Br$, —$CH_2CH_2O$, —$CH_2CH_2OH$, $CH_2CH_2OCOCH_3$, —$CH_2CH_2NH_2$, —$CH_2CH_2N(CH_3)_2$, —$CH_2CH_2NHCH_2CH_3$, —$CH_2CH_2N(CH_3)CH_2CH_3$, —$CH_2CH_2NHCH_2CH_2CH_3$, —$CH_2CH_2NHCH(CH_3)_2$, —$CH_2CH_2NHCH(CH_2)_2$, —$CH_2CH_2N(CH_2CH_3)_2$, —$CH_2CH_2NHCO_2C(CH_3)_3$, and —$CH_2Si(CH_3)_3$.

The term "heteroatom-unsubstituted $C_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —$CH=CH_2$, —$CH=CHCH_3$, —$CH=CHCH_2CH_3$, —$CH=CHCH_2CH_2CH_3$, —$CH=CHCH(CH_3)_2$, —$CH=CHCH(CH_2)_2$, —$CH_2CH=CH_2$, —$CH_2CH=CHCH_3$, —$CH_2CH=CHCH_2CH_3$, —$CH_2CH=CHCH_2CH_2CH_3$, —$CH_2CH=CHCH(CH_3)_2$, —$CH_2CH=CHCH(CH_2)_2$, and —$CH=CH-C_6H_5$.

The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —$CH=CHF$, —$CH=CHCl$ and —$CH=CHBr$, are examples of heteroatom-substituted alkenyl groups.

The term "heteroatom-unsubstituted $C_n$-alkynyl" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted $C_2$-$C_{10}$-alkynyl has 2 to 10 carbon atoms. The groups, —OCH, —C≡CCH_3, and —C≡CC_6H_5 are examples of heteroatom-unsubstituted alkynyl groups.

The term "heteroatom-substituted $C_n$-alkynyl" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkynyl has 2 to 10 carbon atoms. The group, —O=CSi(CH_3)_3, is an example of a heteroatom-substituted alkynyl group.

The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Examples of heteroatom-unsubstituted aryl groups include phenyl, methylphenyl, (dimethyl)phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C≡CH$, —$C_6H_4C≡CCH_3$, naphthyl, quinolyl, indolyl, and the radical derived from biphenyl. The term "heteroatom-unsubstituted aryl" includes carbocyclic aryl groups, biaryl groups, and radicals derived from polycyclic fused hydrocarbons.

The term "heteroatom-substituted $C_n$-aryl" refers to a radical, refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. The term "heteroatom-substituted aryl" includes heteroaryl and heterocyclic aryl groups. It also includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like. Further examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OCOCH_3$, —$C_6H_4OC_6H_5$, —$C_6H_4NH_2$, —$C_6H_4NHCH_3$, —$C_6H_4NHCH_2CH_3$, —$C_6H_4CH_2Cl$, —$C_6H_4CH_2Br$, —$C_6H_4CH_2CH_2OH$, —$C_6H_4CH_2CH_2OCOCH_3$, —$C_6H_4CH_2NH_2$, —$C_6H_4N(CH_3)_2$, —$C_6H_4CH_2CH_2Cl$, —$C_6H_4CH_2CH_2OH$, —$C_6H_4CH_2CH_2OCOCH_3$, —$C_6H_4CH_2CH_2NH_2$, —$C_6H_4CH_2CH=CH_2$, —$C_6H_4CF_3$, —$C_6H_4CN$, —$C_6H_4C≡CSi(CH_3)_3$, —$C_6H_4COH$, $C_6H_4COCH_3$, —$C_6H_4COCH_2CH_3$, —$C_6H_4COCH_2CF_3$, —$C_6H_4COC_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, and imidazoyl.

The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. An "aralkyl" includes an alkyl heteroatom-substituted with an aryl group. Examples of heteroatom-unsubstituted aralkyls include phenylmethyl (benzyl) and phenylethyl.

The term "heteroatom-substituted $C_n$-aralkyl" refers to a radical, having a single saturated carbon atom as the point of attachment, further having a total of n carbon atoms, 0, 1, or more than one hydrogen atom, and al least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —COH, —COCH$_3$, —COCH$_2$CH$_3$, —COCH$_2$CH$_2$CH$_3$, —COCH(CH$_3$)$_2$, —COCH(CH$_2$)$_2$, —COC$_6$H$_5$, —COC$_6$H$_4$CH$_3$, —COC$_6$H$_4$CH$_2$CH$_3$, —COC$_6$H$_4$CH$_2$CH$_2$CH$_3$, —COC$_6$H$_4$CH(CH$_3$)$_2$, —COC$_6$H$_4$CH(CH$_2$)$_2$, and —COC$_6$H$_3$(CH$_3$)$_2$, are examples of heteroatom-unsubstituted acyl groups.

The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, OF, Cl, Br, I, Si, P, and S. For example, a heteroatom-substituted $C_1$-$C_{10}$-acyl has 1 to 10 carbon atoms. The term heteroatom-substituted acyl includes carbamoyl, thiocarboxylate, and thiocarboxylic acid groups. The groups, —COCH$_2$CF$_3$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —CONH$_2$, —CONHCH$_3$, —CONHCH$_2$CH$_3$, —CONHCH$_2$CH$_2$CH$_3$, —CONHCH(CH$_3$)$_2$, —CONHCH(CH$_2$)$_2$, —CON(CH$_3$)$_2$, —CON(CH$_2$CH$_3$)CH$_3$, —CON(CH$_2$CH$_3$)$_2$, and —CONHCH$_2$CF$_3$, are examples heteroatom-substituted acyl groups.

The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$.

The term "heteroatom-substituted $C_n$-alkoxy" refers to a group, having the structure —OR, in which R is a heteroatom-substituted $C_n$-alkyl, as that term is defined above. For example, —OCH$_2$CF$_3$ is a heteroatom-substituted alkoxy group.

The term "heteroatom-unsubstituted $C_n$-alkenyloxy" refers to a group, having the structure —OR, in which R is a heteroatom-unsubstituted $C_n$-alkenyl, as that term is defined above. The term "heteroatom-substituted $C_n$-alkenyloxy" refers to a group, having the structure —OR, in which R is a heteroatom-substituted $C_n$-alkenyl, as that term is defined above. The term "heteroatom-unsubstituted $C_n$-alkynyloxy" refers to a group, having the structure —OR, in which R is a heteroatom-unsubstituted $C_n$-alkynyl, as that term is defined above. The term "heteroatom-substituted $C_n$-alkynyloxy" refers to a group, having the structure —OR, in which R is a heteroatom-substituted $C_n$-alkynyl, as that term is defined above. The term "heteroatom-unsubstituted $C_n$-aryloxy" refers to a group, having the structure —OAr, in which Ar is a heteroatom-unsubstituted $C_n$-aryl, as that term is defined above. An example of a heteroatom-unsubstituted aryloxy group is —OC$_6$H$_5$. The term "heteroatom-substituted $C_n$-aryloxy" refers to a group, having the structure —OAr, in which Ar is a heteroatom-substituted $C_n$-aryl, as that term is defined above. The term "heteroatom-unsubstituted $C_n$-aralkyloxy" refers to a group, having the structure —OAr, in which Ar is a heteroatom-unsubstituted $C_n$-aralkyl, as that term is defined above.

The term "heteroatom-substituted $C_n$-aralkyloxy" refers to a group, having the structure —OAr, in which Ar is a heteroatom-substituted $C_n$-aralkyl, as that term is defined above. The term "heteroatom-unsubstituted $C_n$-acyloxy" refers to a group, having the structure —OAc, in which Ac is a heteroatom-unsubstituted $C_n$-acyl, as that term is defined above. A heteroatom-unsubstituted acyloxy group includes alkylcarbonyloxy and arylcarbonyloxy groups. For example, —OCOCH$_3$ is an example of a heteroatom-unsubstituted acyloxy group. The term "heteroatom-substituted $C_n$-acyloxy" refers to a group, having the structure —OAc, in which Ac is a heteroatom-substituted $C_n$-acyl, as that term is defined above. A heteroatom-substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NMR, in which R is a heteroatom-unsubstituted $C_n$-alkyl, as that term is defined above. A heteroatom-unsubstituted alkylamino group would include —NHCH$_3$, —NHCH$_2$CH$_3$, —NHCH$_2$CH$_2$CH, —NHCH (CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC (CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl.

The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. Examples of heteroatom-unsubstituted $C_n$-alkenylamino groups also include dialkenylamino and alkyl(alkenyl)amino groups.

The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atom, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. An alkynylamino group includes dialkynylamino and alkyl(alkynyl) amino groups.

The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms.

The term "heteroatom-unsubstituted $C_n$-arylamino" includes groups, having the structure —NHR, in which R is a heteroatom-unsubstituted $C_n$-aryl, as that term is defined above. A heteroatom-unsubstituted arylamino group includes diarylamino and alkyl(aryl)amino groups.

The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above. A heteroatom-substituted arylamino group includes heteroarylamino groups.

The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. An aralkylamino group includes diaralkylamino groups.

The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atoms is incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above. The term "heteroatom-substituted aralkylamino" includes the term "heteroaralkylamino."

The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The term amido includes N-alkyl-amido, N-aryl-amido, N-aralkyl-amido, acylamino, alkylcarbonylamino, arylcarbonylamino, and ureido groups. The group, —NHCOCH$_3$, is an example of a heteroatom-unsubstituted amido group.

The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is an example of a heteroatom-substituted amido group.

The term "pharmaceutically acceptable salts," as used herein, refers to salts of compounds of the present disclosure that are substantially non-toxic to living organisms. Typical pharmaceutically acceptable salts include those salts prepared by reaction of a compound of the present disclosure with an inorganic or organic acid, or an organic base, depending on the substituents present on the compounds.

Examples of inorganic acids which may be used to prepare pharmaceutically acceptable salts include: hydrochloric acid, phosphoric acid, sulfuric acid, hydrobromic acid, hydroiodic acid, phosphorous acid, and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids, and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the compounds of the present disclosure with an organic base such as methylamine, ethylamine, ethanolamine, lysine, omithine, and the like. Other suitable salts are known to one of ordinary skill in the art.

It should be recognized that the particular anion or cation forming a part of any salt is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use—A Handbook, by C. G. Wermuth and P. H. Stahl, Verlag Helvetica Chimica Acta, 2002, which is incorporated herein by reference.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A patient can be a human suffering from a neurodegenerative disease, such as Alzheimer's disease, or Parkinson's disease.

As used herein, the term "water soluble" means that the compound dissolves in water at least to the extent of 0.010 mole/liter or is classified as soluble according to literature precedence.

It will be appreciated by one of ordinary skill in the art that asymmetric centers may exist in any of the compounds disclosed herein. Thus, the compounds and pharmaceutical compositions thereof may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E). In any event, as used herein, "predominantly one enantiomer" means that the compound contains at least 95% of one enantiomer, or more preferably at least 98% of one enantiomer, or most preferably at least 99% of one enantiomer. Similarly, the phrase "substantially free from other optical isomers" means that the composition contains at most 5% of another enantiomer or diastereomer, more preferably 2% of another enantiomer CM diastereomer, and most preferably 1% of another enantiomer or diastereomer.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

The term "alkene reduction product" refers to a product obtained from subjecting an alkene to a reduction reaction. A reduction reaction is one in which the alkene gains electrons. Common reduction reactions include catalytic hydrogenation reactions, but other reduction reactions are possible. A double bond in the starting alkene compound is reduced to a single bond in the alkene reduction product.

The term "stable" as used herein refers to compounds which possess stability sufficient to allow manufacture and which maintain the integrity of the compound for a sufficient period of time to be detected and preferably for a sufficient period of time to be useful for the purposes detailed herein.

Other abbreviations used herein are as follows: DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFN-γ, interferon-γ; LPS, bacterial endotoxic lipopolysaccharide;

TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid; HO-1, inducible heme oxygenase.

The terms "inhibiting," "reducing," and "preventing," or any variation of these terms, when used herein include any measurable decrease or complete inhibition to achieve a desired result.

The term "effective" means adequate to accomplish a desired, expected, or intended result.

For clarity, a compound having a particular structural formula denoted with a letter or numeral can be referred to as a compound of that letter or numeral. For example, the compound having the structural formula of Formula IX can be referred to as compound IX.

General Description

In a first aspect, provided are lanthionine ketimine derivatives where the carboxylic acid group at the 3-position of the ring, as numbered in Formula A, has been replaced with a phosphonate group or a phosphonate ester group to increase negative charge density on this moiety. Surprisingly, the compounds referred to herein as LK-P (for lanthionine ketimine phosphonate) compounds or LKE-P (for lanthionine ketimine ester phosphonate) compounds, are capable of entering into cells despite the increased negative charge density resulting from the phosphonate or phosphonate ester group. The LK-P, and LKE-P compounds of the present disclosure have similar therapeutic properties of LK derivatives without the phosphonate. For example, the compounds have neuroprotective activity and have the ability to pass through, and/or be transported through, cellular membranes, such as the blood-brain barrier. Furthermore, without wishing to be bound by theory, it is believed that the increased charge density on the C3 by replacement with a phosphonate increases potency and simultaneously improves stability of the product by reducing oxidative decarboxylation. In a second aspect, provided are lanthionine ketimine derivatives where the carboxylic acid group at the 3-position of the ring has been retained, but the 2-position has been modified. These compounds, referred to herein as LKE compounds, also possess neuroprotective activity and have the ability to pass through and/or be transported through cellular membranes such as the blood-brain barrier. Thus, the present disclosure allows for a previously underdescribed pathway to be attacked with a class of chemical compounds for the clinical management of poorly-met medical conditions.

As shown in PRIOR ART FIG. 1, the basic lanthionine ketimine (LK) structure is as follows, with the atoms of the central ring structure numbered according to the generally accepted nomenclature:

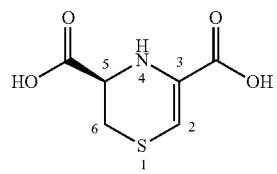

Formula A

LK is also known as (5R)-3,5,-dicarboxy-1-thia-4-aza-2-cyclohexene.

The compounds described herein have the general formula of Formula F:

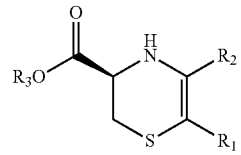

Formula F where $R_1$ is hydrogen or substituted or unsubstituted alkyl, aryl, alkoxy, ester, alkenylamino, alkynylamino, aryloxy, aralkoxy, acyloxy, alkylamino, arylamino, aralkylamino, or amido; $R_2$ is selected from the group consisting of COOH, COOR$_4$, PO(OH)$_2$, PO(OR$_4$)$_2$, POOR$_4$OR$_5$, and POOR$_4$OX, where $R_4$ and $R_5$ are each independently alkyl groups, and X is hydrogen, a group I metal, a halide, or substituted or unsubstituted alkyl, alkoxy, ester, alkenylamino, alkynylamino, aryloxy, aralkoxy, acyloxy, alkylamino, arylamino, aralkylamino, or amido; and $R_3$ is a substituted or unsubstituted alkyl, alkylamino, alkoxy, or ester; provided, however, that when $R_1$ is hydrogen and $R_2$ is COOH, $R_3$ is not ethyl.

In accordance with the present disclosure, increasing charge density by replacing the carboxylate at C3 of LK or LKE with a phosphonate increases potency and, by combining this with alkyl substitution on C2, can increase activity by increasing blood brain barrier (βββ) permeability. The phosphonate analogues provided herein mimic LKE's activity but afford superior autophagy enhancing properties and bioavailability. Hydrophobic substituents are the C2 center can improve potency by increasing Van der Waals interactions with biological binding partnes and/or improving penetration across lipid bilayers.

One class of phosphonate compounds disclosed herein is analogues of lanthionine ketimine phosphonate (LK-P). LK-P has the following structural formula, with the ring structure atoms numbered:

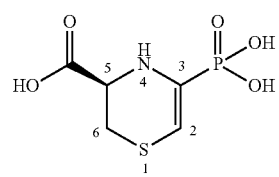

Formula B

LK-P is also known as (5R)-5-carboxy-3-phosphono-1-thia-4-aza-2-cyclohexene.

Another class of phosphonate compounds disclosed herein is analogues of lanthionine ketimine ester phosphonate (LKE-P). LKE-P has the following structural formula, with the ring structure atoms numbered:

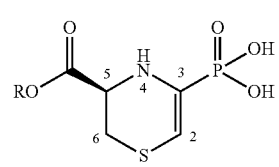

Formula C where R is an alkyl group, such as, but not limited to, methyl, ethyl, propyl, butyl, benzyl, or phenyl.

Given the above root structures and nomenclature, provided herein are LK-P analogues and LKE-P(E) analogues having the following general Formula D:

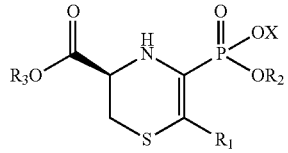

Figure 11:
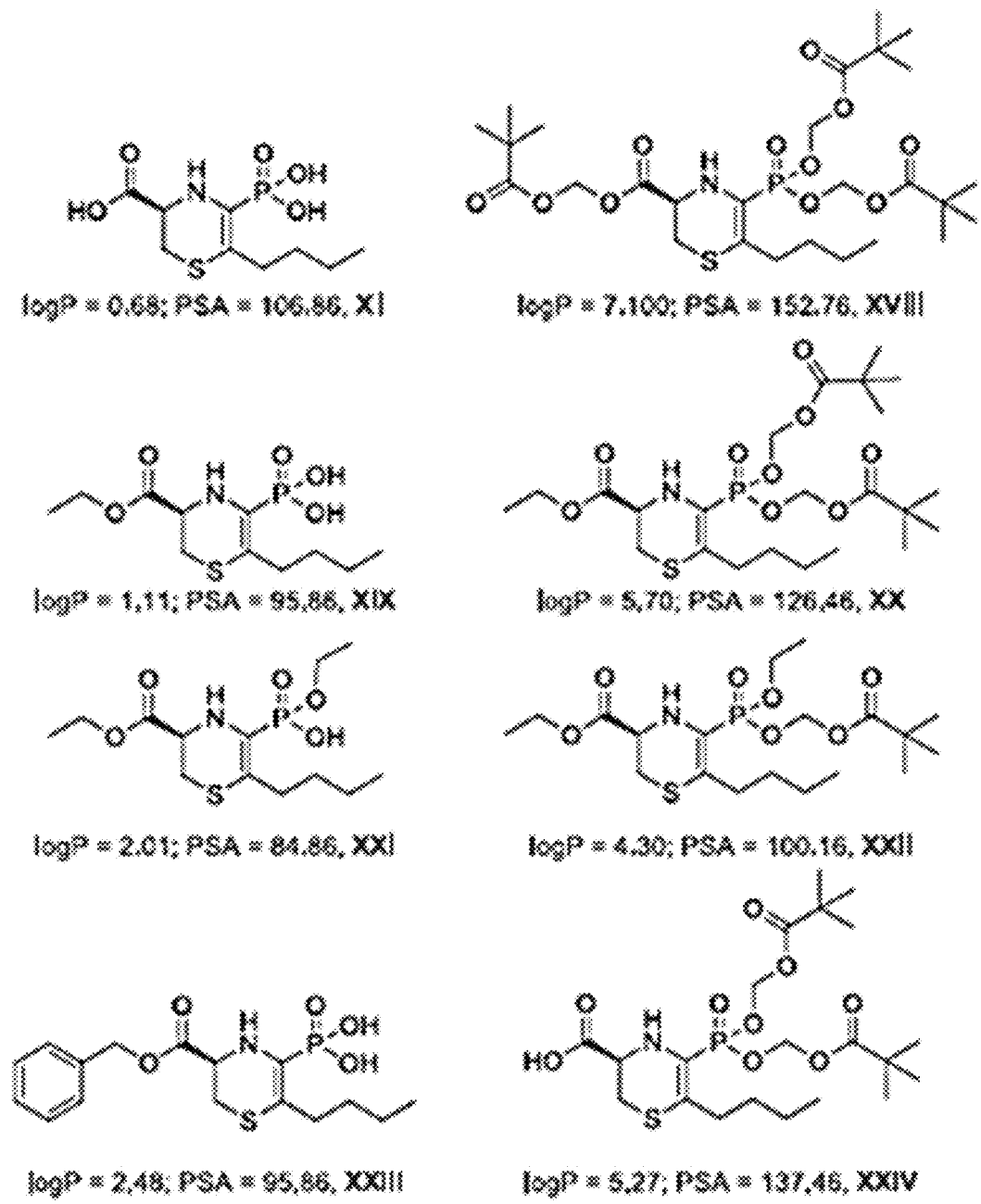
FIG. 11: Structures of non-limiting examples of LK(E)-P(E)s and their log P and PSA values.

Formula D where $R_1$ is hydrogen or substituted or unsubstituted alkyl, aryl, alkoxy, ester, alkenylamino, alkynylamino, aryloxy, aralkoxy, acyloxy, alkylamino, arylamino, aralkylamino, or amido; $R_2$ is hydrogen or substituted or unsubstituted alkyl, alkoxy, or ester; $R_3$ is hydrogen, or substituted or unsubstituted alkyl, aryl, alkoxy, ester, alkenylamino, alkynylamino, aryloxy, aralkoxy, acyloxy, alkylamino, arylamino, aralkylamino, or amido; and X is hydrogen, a group I metal, or substituted or unsubstituted alkyl, alkoxy, ester, alkenylamino, alkynylamino, aryloxy, aralkoxy, acyloxy, alkylamino, arylamino, aralkylamino, or amido. When $R_3$ is hydrogen, the compound is a lanthionine ketimine phosphonate (LK-P) derivative. When $R_3$ is an ester, the compound is a lanthionine ketimine ester phosphonate (LKE-P) derivative. When the C3 carbon includes a phosphonate or phosphonate ester, the C2 carbon can be substituted at will (i.e., $R_1$ can represent a wide variety of possible substituents given that a phosphonate or phosphonate ester is present at the C3 position). For example, in some embodiments, the 2-position is substituted with a phenyl group, a benzyl group, or an alkyl chain ranging from 1 to 10 carbons. Hydrophobic substituents at the C2 center, where the C3 carbon includes a phosphonate or phosphonate ester, improve potency by increasing Van der Waals interactions with biological binding partners and/or improving penetration across lipid bilayers. As shown in FIG. 7 and FIG. 11, many LK-P derivatives and LKE-P derivatives are possible and encompassed within the scope of the present disclosure.

In some embodiments, each of $R_2$ and $R_3$ of Formula D is independently selected from the group consisting of hydrogen, or heteroatom substituted or unsubstituted versions of $C_1$-$C_{15}$-alkoxy, $C_2$-$C_{15}$-alkenylamino, $C_2$-$C_{15}$-alkynylamino, $C_1$-$C_{15}$-aryloxy, $C_2$-$C_{15}$-aralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_1$-$C_{15}$-arylamino, $C_2$-$C_{15}$-aralkylamino, or $C_1$-$C_{15}$-amido.

Included in Formula D are various LK-PE compounds, where $R_3$ is hydrogen, and either (i) $R_2$ is a substituted or unsubstituted ester; or (ii) X is substituted or unsubstituted ester.

Also included in Formula D are various LKE-PE compounds, where $R_3$ is a substituted or unsubstituted ester; and either (i) $R_2$ is a substituted or unsubstituted ester, or (ii) X is a substituted or unsubstituted ester.

In another aspect of the present disclosure, a carboxylate is retained, rather than replaced with a phosphonate, at position 3. These compounds, referred to as lanthionine ketimine derivatives, have the following general Formula E:

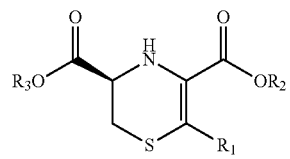

Formula E where $R_1$ is an alkyl or aryl group, such as, but not limited to, methyl, ethyl, propyl, butyl, benzyl, or phenyl; $R_2$ is hydrogen or substituted or unsubstituted alkyl, alkoxy, ester, alkenylamino, alkynylamino, aryloxy, aralkoxy, acyloxy, alkylamino, arylamino, aralkylamino, or amido; and $R_3$ is a substituted or unsubstituted alkyl, alkoxy, ester, alkenylamino, alkynylamino, aryloxy, aralkoxy, acyloxy, alkylamino, arylamino, aralkylamino, or amido. For purposes of clarity, compounds of Formula E where $R_2$ is hydrogen can be referred to as LK-5-E compounds, and compounds of Formula E where $R_2$ is not hydrogen can be referred to as LK-E-5-E compounds (to reflect the presence of an additional ester), though both groups of compounds are genetically referred to herein as LKE compounds. Further, when a compound is referred to as an LKE compound, without specifically identifying the ester, the ester is an ethyl ester. Thus, for example, the name "2-phenyl-LKE" refers to a compound of Formula E where $R_1$ is phenyl, $R_2$ is hydrogen, and $R_3$ is ethyl. However, the name 2-phenyl-5-methyl-LKE refers to a compound of Formula E where $R_1$ is phenyl, $R_2$ is hydrogen, and $R_3$ is methyl.

In general, $R_2$ of Formula E can be any of hydrogen or heteroatom-substituted or unsubstituted versions of $C_1$-$C_{15}$-alkoxy, $C_2$-$C_{15}$-alkenylamino, $C_2$-$C_{15}$-alkynylamino, $C_1$-$C_{15}$-aryloxy, $C_2$-$C_{15}$-aralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_1$-$C_{15}$-arylamino, $C_2$-$C_{15}$-aralkylamino, or $C_1$-$C_{15}$-amido. $R_3$ of Formula E can be any heteroatom-substituted or unsubstituted versions of $C_1$-$C_{15}$-alkoxy, $C_2$-$C_{15}$-alkenylamino, $C_2$-$C_{15}$-alkynylamino, $C_1$-$C_{15}$-aryloxy, $C_2$-$C_{15}$-aralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_1$-$C_{15}$-arylamino, $C_2$-$C_{15}$-aralkylamino, or $C_1$-$C_{15}$-amido.

Non-limiting examples of specific compounds of Formula E are 2-ethyl-LKE and 2-methyl-LKE. In these compounds, $R_1$ is either ethyl or methyl (respectively), $R_2$ is hydrogen, and $R_3$ is ethyl. 2-methyl-LKE has the following structure:

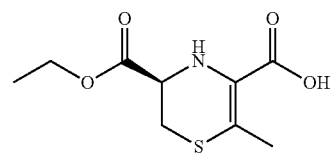

2-ethyl-LKE has the following structure:

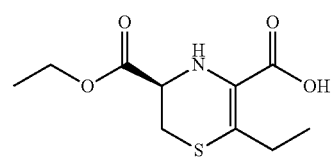 [SMILES: CCOC(=O)[C@@H]1CSC(CC)=C(C(=O)O)N1]

Figure 32A:
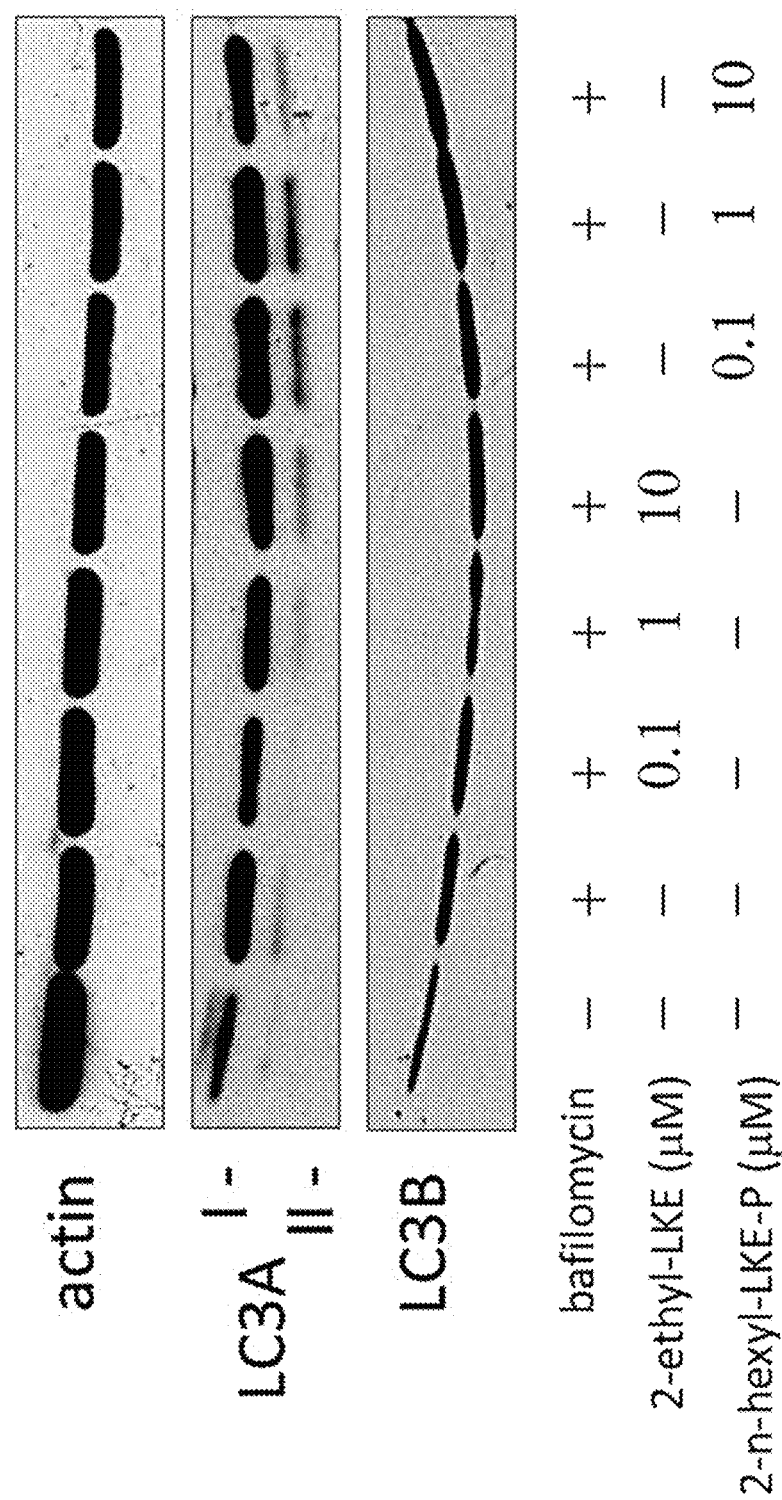
FIGS. 32A-32B: RG2 glioma cells were treated without drug (first column of FIG. 32A), or 4 h with 50 nm bafilomycin-A1 (BAF), or with BAF and increasing concentrations of 2-ethyl-LKE or the 2-n-hexyl-phosphonate analog of LKE (2-n-hexyl-LKE-P).
Figure 32B:
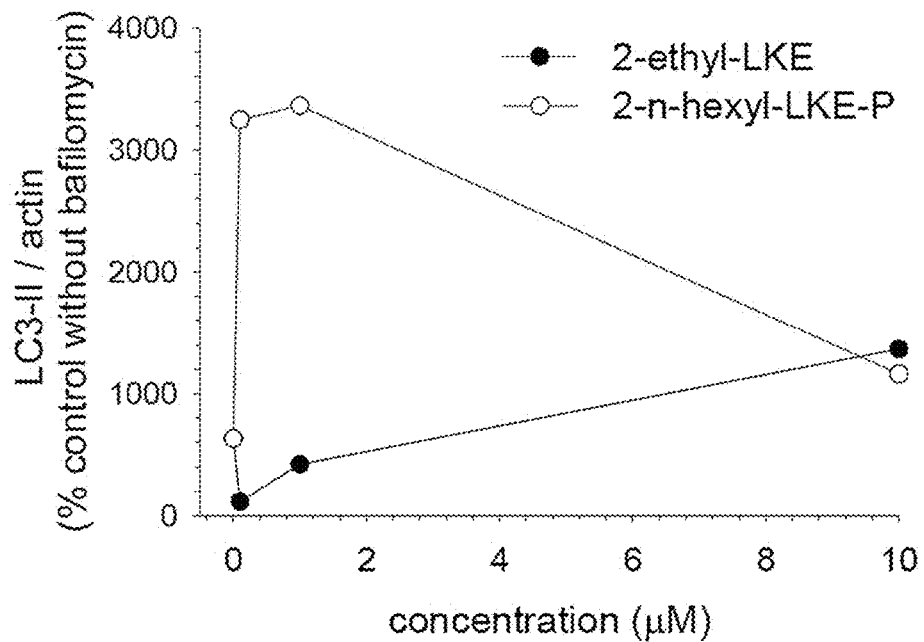

The biological activity of 2-ethyl-LKE is shown in FIGS. 32A-32B.

Figure 8:
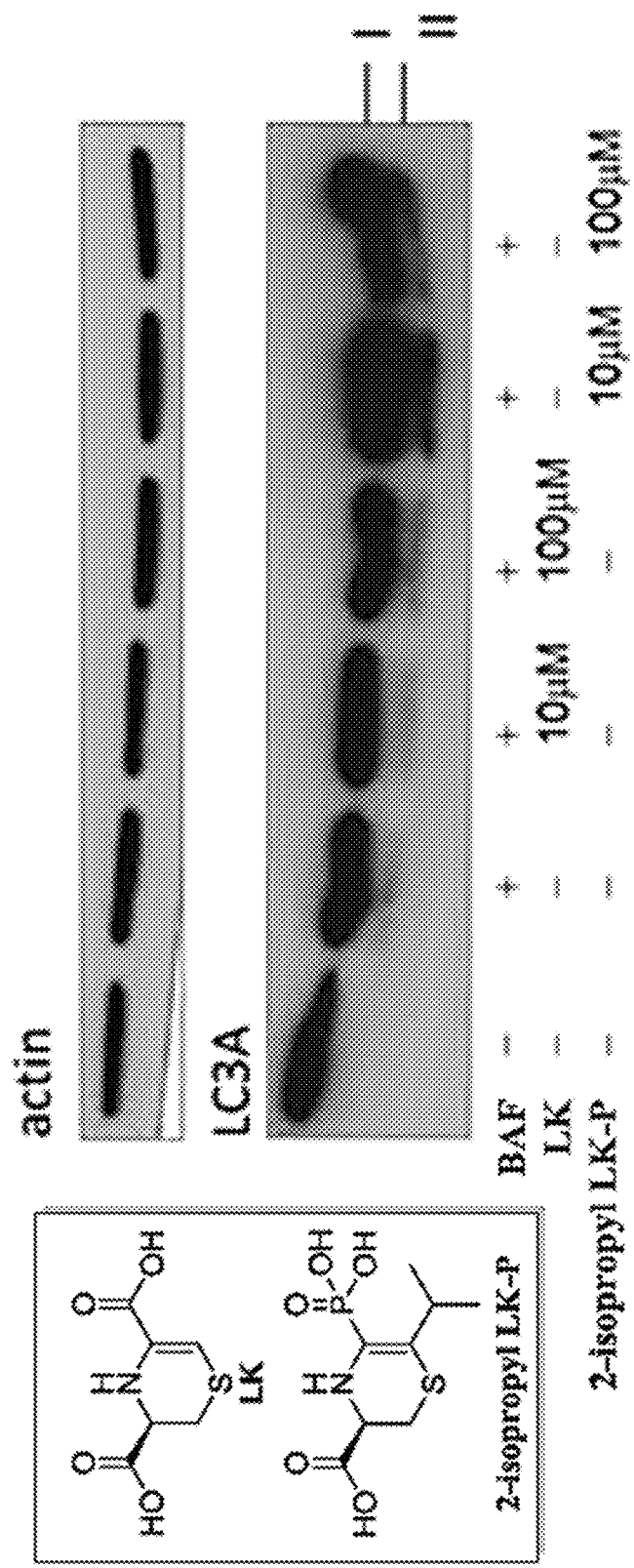
FIG. 8: C2-alkyl derivatives of LK-phosphonates activate cellular autophagy. RG2 glioma cells were treated without drug (first column) or 4 h with 50 nM bafilomycin-A1 (BAF), the indicated concentration of LK or the phosphonate analog 2-isopropyl lanthionine-ketimine-phosphonate (2-isopropyl LK-P). The lower band corresponds to LC3-II. An increase in the intensity of this band, in the presence of bafilomycin-A1, indicates increased autophagic flux. With respect to this parameter, 2-isopropyl lanthionine-ketimine-phosphonate clearly was more potent at 10 mM than was LK.

The LK-P and LKE-P compounds can be made according to the synthetic schemes depicted in FIGS. 2-5. FIG. 2A depicts a general synthetic procedure for the preparation for 2-substituted LKE-Ps. FIG. 3A depicts a general synthetic procedure for the preparation for 2-substituted LKE-PEs. As seen in these schemes, in one embodiment of a method of making a compound herein, an acid chloride is converted into the dialkyl α-ketophosphonate (compound class 10) by the Michaelis-Arbuzov reaction. The dialkyl phosphonate is either partially deprotected with a Group I metal iodide in refluxing acetone or acetontrile (FIG. 3A), or fully deprotected by reaction with bromotrimethylsilane under microwave irradiation (FIG. 2A). The diacid (compound class 20) or monoacid (compound class 50) is treated with bromophosphonate (compound class 30 or 60) which is treated with a derivative of cysteine in water to afford the lanthionine ketimine phosphonate derivative (compound class 40 or 70) after purification. Alternatively, the monoester or diacid can be treated with bromine in refluxing dichloromethane in a modified Hell-Volhard-Zelinsky reaction to afford the α-keto-β-bromophosphonate, which is treated with a derivative of cysteine in water to afford the 2-substituted lanthionine ketimine phosphonate derivative after purification. This method can be used to make, for example, 2-isopropyl LK-P, 2-n-butyl-LK-P, 2-n-butyl-LKE-P, 2-n-hexyl-LK-P and 2-nhexyl-LKE-P, 2-phenyl-LK-P, 2-benzyl-LK-P, and the like. (The activity for LK and 2-isopropyl LK-P is shown in FIG. 8, and activity for 2-n-hexyl-LKE-P is shown in FIG. 32A.) As seen from these schemes, as well as Scheme 5 shown in FIG. 6, phosphonate analogues of 3-halogenated, 3-substituted pyruvate can be reacted with cysteine derivatives, such as L-cysteine or L-cysteine ethyl ester, to produce LK-P or LKE-P compounds. Any number of cysteine diesters can be made, and then the disulfide of the cysteine diesters can be reduced to afford any particular ester at the X or $R_2$ position of Formula D. Furthermore, alkene reduction products of the lanthionine ketimine phosphonate derivatives can be prepared by a suitable alkene reduction reaction, such as a catalytic hydrogenation reaction or a hydride reduction. If the alkene reduction product is prepared via the use of a hydride reducing agent, trans isomers are obtained. If the alkene reduction product is prepare via catalytic hydrogenation, cis isomers are obtained.

FIG. 2B depicts an example scheme showing the synthesis of 2-isopropyl lanthionine ketimine phosphonate (2-isopropyl-LK-P) from 3-methylbutanoyl chloride. FIG. 3B depicts an example scheme showing the synthesis of 2-isopropyl lanthionine ketimine phosphonate ethyl ester (2-isopropyl-LK-PEE) from 3-methylbutanoyl chloride. FIG. 4 depicts an example scheme showing the synthesis of 2-isopropyl lanthionine ketimine ethyl ester phosphonate (2-isopropyl-LKE-P) from 3-methylbutanoyl chloride. FIG. 5 depicts an example scheme showing the synthesis of 2-isopropyl lanthionine ketimine ethyl ester phosphonate ethyl ester (2-isopropyl-LKE-PEE) from 3-methylbutanoyl chloride.

In one embodiment, an acid chloride is converted into the dialkyl α-ketophosphonate by the Michaelis-Arbuzov reaction. The dialkyl phosphonate is either partially deprotected with a Group I metal halide in refluxing acetone or acetonitrile, or fully deprotected by reaction with bromotrimethylsilane under microwave irradiation. The monoester or diacid is treated with bromine in refluxing dichloromethane in a modified Hell-Volhard-Zelinsky reaction to afford the α-keto-β-bromophosphonate, which is treated with a derivative of cysteine in water to afford the lanthionine ketimine phosphonate derivative after purification. It is understood, however, that this is merely one example, and other methods of making the lanthionine ketimine phosphonate derivatives are possible and entirely encompassed within the scope of the present disclosure.

Figure 30A:
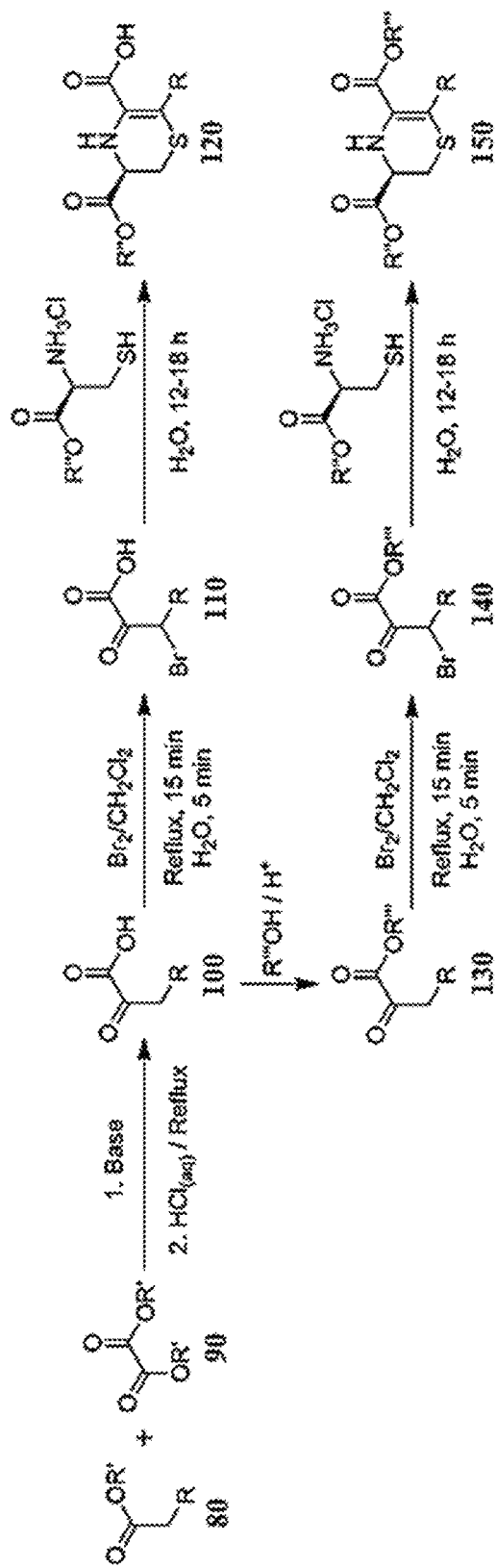
FIGS. 30A-30B: Scheme depicting a general synthetic procedure for the preparation of 2-substituted lanthionine ketimine-5-esters (2-substituted LK-5-(E)s) and 2-substituted lanthionine ketimine 3,5-diesters (2-substituted LK-3, 5-di(E)s).
Figure 30B:
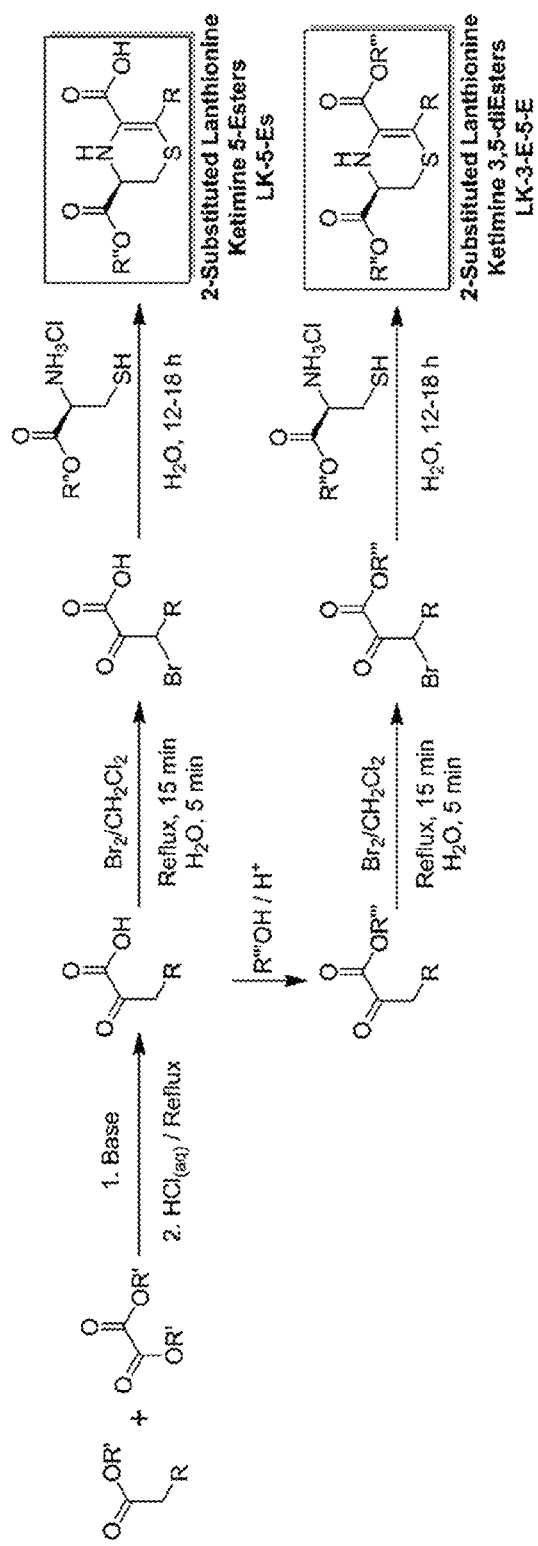

For making the compounds of the present disclosure having a carboxylate rather than a phosphonate at the 3-position, reactions similar to the preparation of the 2-substituted and unsubstituted lanthionine ketimine phosphonates shown in FIGS. 2A, 3A can be employed. Using direct bromonation of an α-keto carboxylic acid (compound class 100, which is either commercially available or prepared from the reaction of the enolate of a carboxylic acid ester (compound class 80) with a dialkyl oxalate (compound class 90)) followed by acid hydrolysis and decarboxylation of the intermediate diester afford new α-ketocarboxylic acids (compound class 100), as shown in the scheme depicted in FIGS. 30A-30B. The α-ketoacids of class 100 can either be brominated directly and subsequently reacted with a cysteine derivative to afford the 2-substituted lanthionine ketimines of compound class 120, or esterified under standard conditions to afford α-ketoacid esters of compound class 130. These esters can be treated analogously to compound class 100 to afford 2-substituted lanthionine ketimine 3,4-diesters of compound class 150. The examples herein describe the use of this method to make 2-methyl LKE and 2-ethyl-LKE, the activity data for which is shown in FIGS. 32A-32B. It is understood, however, that this is merely one example of a method of making a lanthionine ketimine derivative, and other methods of making the lanthionine ketimine derivatives are possible and entirely encompassed within the scope of the present disclosure. Furthermore, alkene reduction products of the lanthionine ketimine derivatives having a 3-carboxylate can be prepared by a suitable alkene reduction reaction, such as a catalytic hydrogenation reaction or a hydride reduction. If the alkene reduction product is prepared via the use of a hydride reducing agent, trans isomers are obtained. If the alkene reduction product is prepare via catalytic hydrogenation, cis isomers are obtained.

In general, lanthionine ketimine derivates are neuroprotective compounds that act through a mechanism of action which relies upon their ability to initiate autophagy, which is a cellular process for selective recycling of macromolecules and organelles. An assay to measure for this ability to stimulate cell autophagy has been developed for lanthionine ketimine derivatives. As described in the Examples herein, the lanthionine ketimine phosphonate derivatives show efficacy in this assay, indicating they act like other lanthionine ketimine derivatives and are also neuroprotective.

In the assay, cells are treated with subtoxic concentrations of bafilomycin-A, which blocks lysosomal acidification. This prevents autophagosome fusion with lysosomes at a specific point. For example, RG2 glioma cells (or other cell types) are "clamped" by addition of 10-50 nM bafilomycin-A1 to block autophagosome fusion with lysosomes and eliminate autophagy clearance. Then, autophagy flux is measured by the conjugation of phosphatidylethanolamine to LC3-I, yielding an electrophoretically separable LC3-II by western blot. LC3-II acts as a link between nascent autophagosomes and cargo being directed into these structures. An autophagy enhancer will increase LC3-II in the presence of bafilomycin, whereas a compound that inhibits autophagy completion will not do so. Thus, the LC3A-I to LC3A-II conversion in the presence of bafilomycin-A1 constitutes a valid measure of autophagy.

In FIG. 8, it is shown that 2-isopropyl lanthionine ketimine phosphonate (2-isopropyl-LK-P) stimulates autophagy in RG2 cells at low micromolar concentrations, similar to what has been previously observed for LK and LKE. In FIG. 32A, it is shown that 2-ethyl-LKE and 2-n-hexyl-LKE-P both stimulate autophagy in RG2 cells, and that the latter compound is potent at 0.1 μM, with approximately 10-fold greater potency than known results for LKE. Thus, the lanthionine ketimine phosphonate derivatives, and lanthionine ketimine derivatives which retain a carboxylate at the 3-position, are potent autophagy stimulators.

In comparison to the known LK and LKE, the phosphonate derivatives of the present disclosure have various advantages. These advantages include (1) a greater stability relative to the carboxylates due to the phosphonates not being subject to oxidative decarboxylation and resulting dimerization, which is a major route to decomposition of lanthionine ketimintes in concentrated solution; (2) better bioavailability; and (3) better potency due to increased charge density of the phosphonate versus the carboxylate. The greater charge density of the phosphonate may also impede passage across cell membranes, and hence, the addition of a hydrophobic group (such as an isopropyl group or a 2-n-hexyl group) to the C2 corner compensates for the decreased lipid solubility imparted by the phosphonate. The data shown in FIGS. 8-9 clearly shows that the phosphonate analogues of lanthionie ketimine derivatives retain potency as autophagy-promoting agents.

It is further contemplated that the R groups of the LK, LKE, LKE-P, LK-P, LK-PE, and LKE-PE compounds (all collectively encompassed by the phrase "LKE, LK-P, LKE-P, or LKE-PE compounds") of the present disclosure can be substituted with one or more functional groups that will facilitate the transport of the resulting molecule through the blood brain barrier. In some of these embodiments, the functional group interacts with blood brain barrier-specific transport mechanisms. As one non-limiting example, an ascorbyl derivative of LKE, LK-P, or LKE-P should take advantage of blood brain barrier ascorbyl transporters. Also, certain amino acid esters or amide derivatives of LKE, LK-P, or LKE-P compounds should be readily transported across the blood brain barrier by means of blood brain barrier transport enzymes. In certain embodiments, $R_1$ and/or $R_2$ is a serinyl group. Methods of making ascorbyl, dehydroascorbyl, and amino acid esters of drugs are known in the art. Conjugation of ascorbyl, dehydroascorbyl, serinyl, or glycinyl to the LKE, LK-P, or LKE-P compounds may be performed using techniques known in the art. See, for example, Manfredini et al., 2001 and Huang et al., 2001, both of which are incorporated herein by reference.

The LKE, LK-P, and LKE-P compounds described herein are useful for the treatment and/or prevention of autophagic-related diseases, including diseases affecting the central nervous system. The disease may be sepsis and/or an inflammatory disease. The inflammatory disease may be ALS, a degenerative motor neuron disease, AD, Parkinson's disease, Huntington's disease, multiple sclerosis, macular degeneration, a cardiovascular disease, atherosclerosis, rheumatoid arthritis, or inflammatory bowel disease (IBD). The disease may be characterized by deficient kynurenine transaminase (KAT)/glutamine transaminase-K (GTK)/cysteine conjugate β-lyase (CCβL) activity in the subject. The disease may be hypertension, Huntington's disease, attention deficit disorder, depression, or generalized anxiety disorder. In certain embodiments, the disease is characterized by excessive nitric oxide production, excessive glutamate excitotoxicity, or excessive prostaglandin E2 (PGE2) in the subject. The disease may be characterized by activated macrophage cells and/or activated microglia cells in the subject. In general, it is believed that the phosphonate derivatives herein have similar activity to LK and LKE, such as reducing pathology in ALS, stroke, Huntington's disease, and AD.

The treatment may further comprise administering a second anti-inflammatory compound to the subject, such as a Krebs cycle α-keto acid. The Krebs cycle α-keto acid may be pyruvate or a α-ketoglutarate. In certain embodiments where the LKE, LK-P, or LKE-P compound is administered to the subject, the method may further comprise administering pyruvate (e.g., from about 25 to about 75 mg/day) and/or α-ketoglutarate to the subject.

In certain embodiments, the disclosure provides a method of reducing damage to a cell resulting from oxidative stress, excitotoxicity, free radical toxicity, or excitatory amino acid toxicity, wherein the compound is contacted with the cell, and the cell is a neuron, macrophage, or glial cell (so long as the glial cell is not a glioma cell). The glial cell may be an astroglia cell or a microglial cell. The neuron may be a motoneuron. The oxidative stress may or may not involve free radicals. For example, both hypochlorite and hydrogen peroxide can oxidize substrates through non-radical mechanisms. Free radical toxicity may result from nitric acid. In certain embodiments, the excitatory amino acid toxicity is glutamate-induced excitotoxicity. The cell may be present in a subject, such as a human patient.

The present disclosure provides a method of treating a patient having an inflammatory disease, comprising administering a therapeutically effective amount of an LKE, LK-P, or LKE-P compound to the patient. In some embodiments, the inflammatory disease is rheumatoid arthritis, or inflammatory bowel disease. In some embodiments, the LKE, LK-P, or LKE-P compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution or an organic diluent. In some embodiments, the therapeutically effective amount is 0.1-1000 mg/kg. In further embodiments, an additional agent is administered to the patient.

The present disclosure also provides a method of treating a patient having a neurodegenerative disease, comprising administering a therapeutically effective amount of an LKE, LK-P, LKE-P, or LKE-PE compound to the patient. In some embodiments, the neurodegenerative disease is AD, Parkinson's disease, Huntington's disease, multiple sclerosis, or ALS. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution or an organic diluent. In some embodiments, the therapeutically effective amount is 0.1-1000 mg/kg. In further embodiments, an additional agent is administered to the patient.

The present disclosure also provides a method of treating a patient having a pathogenesis involving the excessive production of nitric oxide or prostaglandins, comprising administering a therapeutically effective amount of an LKE, LK-P, LKE-P, or LKE-PE compound to the patient. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution or an organic diluent. In some embodiments, the therapeutically effective amount is 0.1-1000 mg/kg. In further embodiments, an additional agent is administered to the patient. In certain embodiments, the prostaglandins are inflammatory prostaglandins.

The present disclosure also provides a method of treating a patient having a disorder characterized by the overexpression of iNOS or COX-2 gene, comprising administering a therapeutically effective amount of an LKE, LK-P, LKE-P, or LKE-PE compound to the patient. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution or an organic diluent. In some embodiments, the therapeutically effective amount is 0.1-1000 mg/kg. In further embodiments, an additional agent is administered to the patient.

The present disclosure also provides a method of modulating transcription or translation of iNOS or COX-2 genes in a patient, comprising administering a therapeutically effective amount of an LKE, LK-P, LKE-P, or LKE-PE compound to the patient. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution or an organic diluent. In some embodiments, the therapeutically effective amount is 0.1-1000 mg/kg. In further embodiments, an additional agent is administered to the patient.

The present disclosure also provides a method of modulating excessive nitric oxide or prostaglandin formation in a patient, comprising administering a therapeutically effective amount of an LKE, LK-P, LKE-P, or LKE-PE compound to the patient. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution or an organic diluent. In some embodiments, the therapeutically effective amount is 0.1-1000 mg/kg. In further embodiments, an additional agent is administered to the patient. In certain embodiments, the formation of inflammatory prostaglandins may be modulated.

The present disclosure also provides a method of treating a subject at risk for having a stroke, comprising administering to the subject a pharmacologically effective amount of an LKE, LK-P, LKE-P, LKE-PE compound to the subject. In certain embodiments, the subject is a human patient.

The present disclosure also provides a method of treating a subject for a stroke, comprising administering to the subject a pharmacologically effective amount of an LKE, LK-P, LKE-P, or LKE-PE compound to the subject. In certain embodiments, the subject is a human patient. In certain embodiments, the treatments for stroke or stroke-related complications are administered after the event of stroke or other stoppage of blood flow to the brain (e.g., in case of heart failure).

The present disclosure also provides a method of treating a patient having cancer, comprising administering a therapeutically effective amount of an LKE, LK-P, LKE-P, or LKE-PE compound to the patient. In certain embodiments, the cancer is brain, lung, liver, spleen, kidney, lymph node, small intestine, pancreas, blood cell, bone, colon, stomach, endometrium, prostate, testicle, ovary, central nervous system, skin, head and neck, esophagus, or bone marrow.

The present disclosure also provides a method for treating neurodegenerative diseases wherein protein delivery to lysosomes is compromised, comprising administering a therapeutically effective amount of an LKE, LK-P, LKE-P, or LKE-PE compound to a patient in need thereof and treating a neurodegenerative disease wherein protein delivery to lysosomes is compromised. In certain embodiments, the neurodegenerative disease wherein protein delivery to lysosomes is compromised is selected from the group consisting of Batten disease (neuronal ceroid lipofuscinosis, Niemann-Pick disease, Machado-Joseph disease, spinocerebellar ataxia, Fabry disease, and mucopolysaccharoidosis.

Pharmaceutical compositions of the present disclosure comprise an effective amount of an LKE, LK-P, LKE-P, or LKE-PE compound (an "active" compound), and/or additional agents, dissolved or dispersed in a pharmaceutically acceptable carrier. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515, and 5,399,363 are each specifically incorporated herein by reference in their entirety).

Solutions of the compositions disclosed herein as free bases or pharmacologically acceptable salts may be prepared in water suitably mixed with a surfactant or organic diluent, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and laurocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compounds and compositions described herein are useful for treating various autophagy-related diseases and disorders such as, but not limited to: ALS, AD, stroke, Huntington's disease, and Parkinson's disease. Furthermore, the compounds and compositions herein can be used in combination therapies. That is, the compounds and compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

It is further envisioned that the compounds and methods described herein can be embodied in the form of a kit or kits. A non-limiting example of such a kit is a kit for making an LKE, LK-P, LKE-P, or LKE-PE compound, the kit comprising (i) at least one of an α-keto-β-bromophosphonate, an α-keto-β-bromocarboxylic acid, an α-keto-β-bromoacid ester, an α-ketocarboxylic acid, or an α-ketoacid ester and (ii) a cysteine derivative in separate containers, where the containers may or may not be present in a combined configuration. Many other kits are possible, such as kits further comprising a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Embodiments of the present disclosure further include methods of determining coverage or denial of health insurance reimbursement and/or payment for treatments of disease comprising the compounds or compositions described herein. In certain embodiments, the treatment comprises an LKE, LK-P, LKE-P, or LKE-PE compound, or a pharmaceutical composition containing an LKE, LK-P, LKE-P, or LKE-PE compound, and a provider of health insurance denies coverage or reimbursement for the treatment.

EXAMPLES

In these examples, a series of 3-substituted phosphonic acid analogs of LK and LKE (LK-Ps or LKE-Ps, respectively) were synthesized in order to increase the charge density and/or hydrogen-bonding capability available at the 3-position of the 1-thia-4-aza-2-cyclohexene ring system. In order to compensate for the increased polarity at the 3-position, alkyl substituents were also prepared at the 2-position. Thus, compounds were prepared with C-2-alkyl side groups, with 3-phosphonate substitution for the LK (or LKE) carboxylate group, or with both modification. These compounds were tested for ability to induce autophagy and were found to retain activity at or above that of lanthionine ketimine and its 5-ethyl ester. Without wishing to be bound by theory, it is believed that the compounds have improved pharmacokinetic and stability characteristics owing to the reduced likelihood of oxidative decarboxylation at the C3 position. 2-substituted analogs of LKE which retain the carboxylate at the 3-position were also synthesized, tested for ability to induce autophagy, and found to retain activity above that of LKE.

Phosphonate Analogues and Phosphonate Ester Analogues

Phosphonate analogues of LK(E), namely LK(E)-Ps, also exhibit autophagy enhancement and are amenable to structural modification and functional optimization.

Furthermore, since the compounds should cross the βββ, a synthetic strategy was developed to selectively incorporate lipophilic groups to the core of the molecules (FIG. 6, Scheme 5) to enhance delivery of the small molecules to their targets within the brain. This synthesis is also amenable to manipulation of the carboxylic acid ester group. A multiple step, "one-pot" procedure was designed to produce the target LK(E)-Ps bearing lipophilic groups at the two position of the 4-aza-1-thia-2-cyclohexene (FIG. 6, Scheme 5). Without wishing to be bound by theory, it is believed that the potent biological activities of LK derivatives somewhat depend on the unique arrangement of dicarboxylic acids around the 1-thia-4-aza-2-cylcohexene core.

A number of α-ketophosphonate diesters have been prepared utilizing the Michaelis-Arbuzov reaction (Synthesis of compound I, Scheme 5). Compound I was used as the starting material for the sequence for a number of reasons, first, the bromination of compounds II (carbon 3 on compound n, for this example, was substituted with isopropyl) is complicated by steric hindrance around carbon 3 (Scheme 5), the site of bromination, alpha to the ketone. By strategically placing a sterically hindered (but not the most sterically hindered) isopropyl group on carbon 3, a positive reaction outcome shows that the reaction is feasible with a wide variety of substituents in this position (i.e., if a "difficult" bromination is efficacious, less sterically hindered substrates should be equally or more reactive in this sequence). The bromination was successful, as was the subsequent substitution reaction with cysteine hydrochloride in water, the cyclization and dehydration reactions (imine formation), and the tautomerization reaction (enamine formation, Scheme 5, lower panel) as determined by HRMS and NMR analysis. The product of the specific reaction delineated in Scheme 5,2-isopropyl-LK-P, was isolated from the reaction mixture as a solid, a fortuitous result. This sequence was also performed to synthesize 2-n-butyl-LK-P (XI, UPLC-MS and NMR confirmed, FIG. 9).

Figure 9:
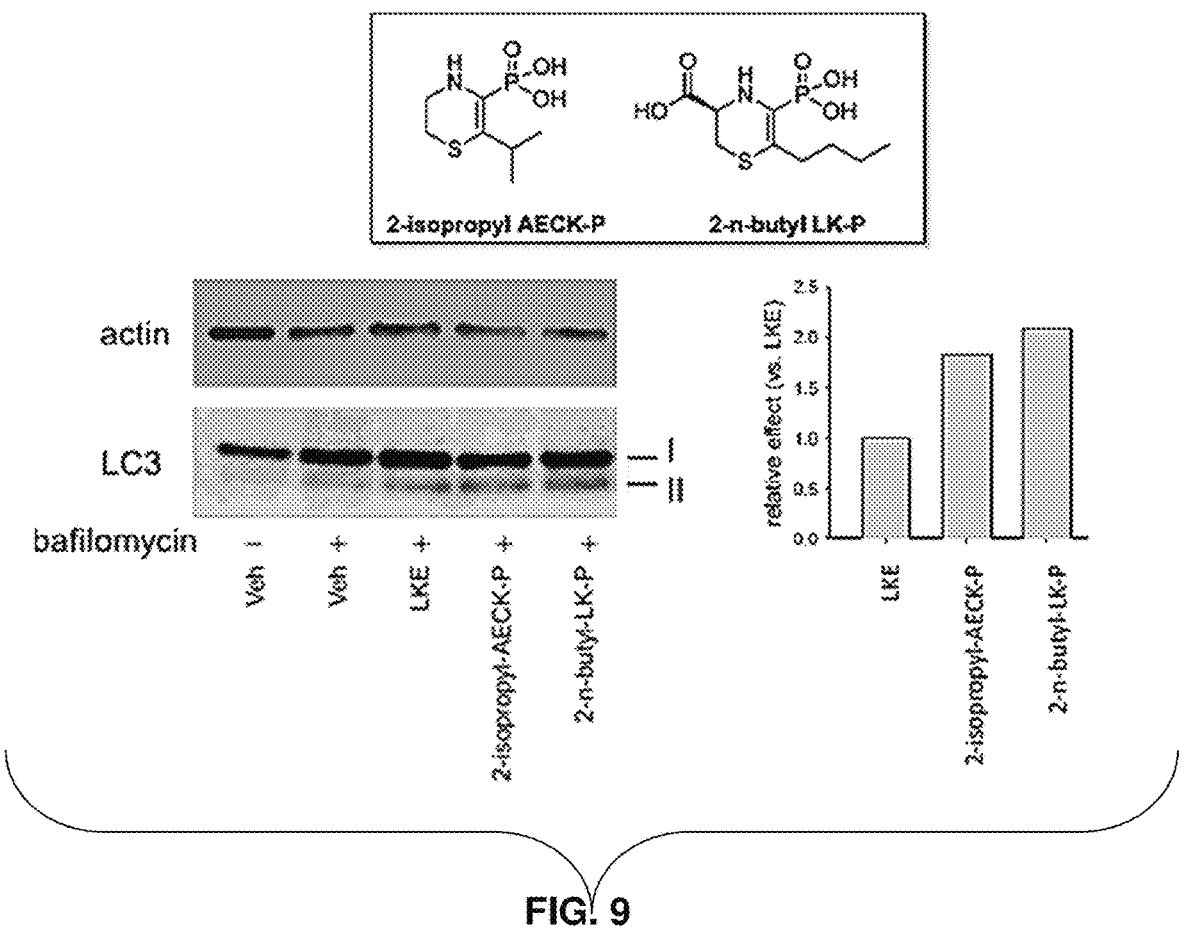
FIG. 9: Quantitation of autophagy stimulation by LKE and analogues. Cells were treated as in FIG. 8, and the ratio of LC3-II band densities for the analogue-treated cells, relative to the LKE-treated cells, was used to determine the potency of autophagy stimulation afforded by the analogues. The graph on the right shows that 2-isopropyl-AECK-P and 2-n-butyl-LK-P each demonstrated a greater autophagy activation effect than LKE.

In a separate experiment, cysteine-HCl was replaced with cysteamine-HCl to afford the compound shown in FIG. 9, AECK-P (AminoEthyl Cysteine Ketimine-Phosphonate). The success of the synthetic strategy, to afford a range of new compounds, with varying molecular architecture, validates this pathway and indicates that the preparation of a library of compounds can be synthesized employing this strategy.

Figure 10:
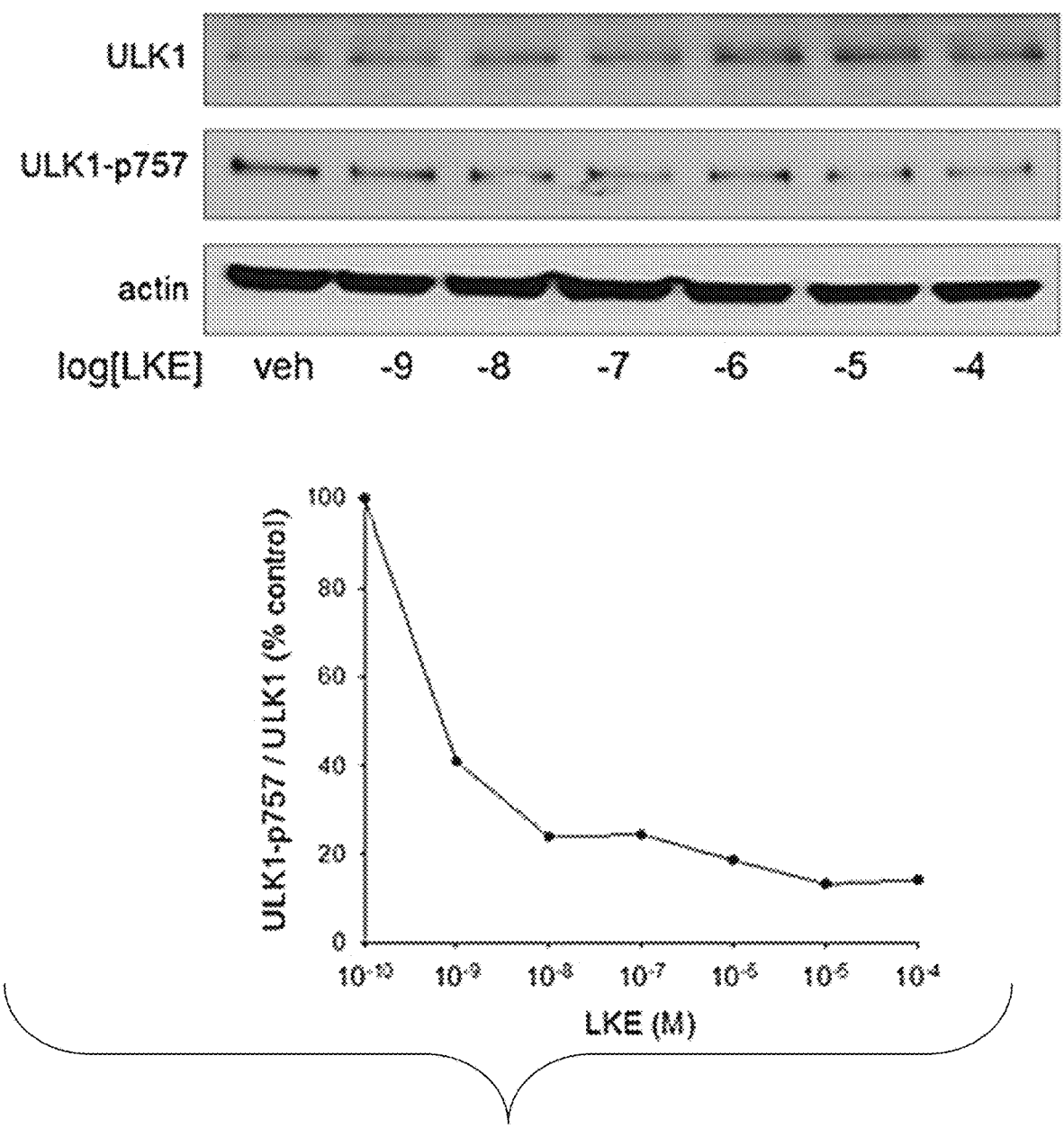
FIG. 10: LKE effect on ULK1 is a sensitive indicator of autophagy activation. Top: RG2 glioma cells were treated 24 h with the indicated concentration of LKE, lysed, and probed for total ULK1 or ULK1 phosphorylated on the mTOR target residue 757. Bottom: the ratio of ULK1/ULK1 (p757) band densities was plotted as a function of LKE concentration.

To gauge the relative potency of the synthesized compounds versus LKE in a defined autophagy assay, the synthesized compounds were tested using two individual, sensitive, autophagy assays, in multiple cell lines. For example, in RG2 glioma cells (FIGS. 8-9, detailed methods provided below), upon visual inspection, 2-isopropyl-LK-P was a much more potent stimulator of autophagy than LK. To obtain a comparable value of effectiveness of the compounds, relative to LKE, quantitative western blot densitometry was employed (FIG. 9). This technique has been documented in the literature for use in the comparison of the potency of individual compounds, relative to a recognized standard, and this technique has become a standard method of autophagy analysis. In addition to quantitating the stimulation of autophagy for the compounds, relative to LKE, because it is cell based, this assay also provides evidence that the compounds can permeate cell membranes. This affords valuable information for the comparison of individual compounds to stimulate autophagy, and will allow them to be ranked for use in the determination of a structure activity relationship (SAR). FIG. 9 displays the comparison of AECK-P and 2-n-butyl-LK-P in stimulating autophagy in RG2 glioma cells. As is indicated, all compounds tested stimulated autophagy more potently than did LKE. This not only indicates activity, but confirms that the compounds (even the most unlikely cell permeating analogue, 2-isopropyl-AECK-P) can enter cells to elicit a response. For validation purposes, a second, quantitative autophagy stimulation assay was utilized. FIG. 10 demonstrates the ability of this assay to determine a sensitive estimation of LKE potency upon the mTOR pathway (i.e., stimulation of autophagy) by monitoring the simultaneous change in ULK1 increase and ULK1(p757) decrease. At 24 h in RG2 cells, LKE affected the ULK1 system with an $EC_{50}$ of approximately 50 nM. This second assay provides validation for the LC3 assay.

The assay results obtained for the LK(E)-Ps are extremely positive. These results show that the developed synthetic strategy is successful, and that phosphonate analogues of LK, with a bulky lipophilic group on the 2 position of the ring, with or without the carboxylic acid moiety, or a straight chain lipophilic moiety at the 2-position, are as active in stimulating autophagy as LK (the natural neuroprotectant) or LKE (the more brain-penetrant ethyl ester of LK).

Theoretically, the structures of both LKE and LK(E)-Ps make them unlikely candidates for crossing the blood brain barrier. The data indicates good βββ penetrability of LKE (both directly by measurement of brain LKE levels and the positive results in animal studies). Surprisingly, the comparable activity of 2-isopropyl-LK-P, 2-isopropyl AECK-P, and 2-n-butyl-LK-P to LKE, in cell based assays, shows a high probability of this compound class (LKE-Ps) to be effective in treating disorders of the CNS.

FIG. 11 shows a panel of compounds, and their physiochemical parameters, indicating the large variety of medicinal chemical modifications encompassed within the present disclosure. Using LK and LKE (FIG. 7) and 2-n-butyl-LK-P (FIG. 11) as standards, and the calculated properties log P and PSA (calculated with MarvinSketch 15.6.1.0) as a guide, a systematic approach can be taken to identify compounds retaining the polar functional groups required for biological activity while, at the same time, choosing the correct chemical groups to "mask" these polar groups to afford a "prodrug" capable of diffusing into and through the βββ, while not being too large as to bind to plasma proteins or simply not be able to "squeeze" between the tight cellular junctions of the βββ. First, a systematic approach of synthesizing LK-Ps (carboxylic acid moiety) and LK(E)-Ps (carboxylic acid ethyl ester moieties), varying the 2-position tail length from butyl to octyl (FIG. 7) can be employed. As is noted in FIG. 7, when increasing the lipophilic tail at the 2 position, the log P value continues to rise from 0.22 to 2.36, while the PSA reaches a plateau at 106.86. This indicates the limitations on some computational methods. The algorithm used to calculate the PSA places such a large emphasis on the phosphonate moiety that the increase in hydrophobic character of the group at the 2-position is overshadowed by this factor. This plateau is also observed when using the Molinspiration property engine, v2014.11, and is, therefore, not software driven. This is why it is important to know the limitations of the calculations used. The calculations are performed as a preliminary guide, but it is always more reliable to obtain actual biological data for chemical compounds to make decisions on future directions.

As the data shows, LKE (log P=0.68, PSA=75.63), 2-isopropyl-LK-P (log P=0.22, PSA=106.86), and 2-n-butyl-LK-P (log P=0.68, PSA=106.86) all enter into cells and stimulate autophagy to varying degrees. Although the PSA values plateau at 106.86 with the LK-Ps and 95.86 with the LK(E)-Ps, the log P values continue to rise.

2-n-butyl-LK-P (XI), being used as a starting point, can be modified using a "pro-drug" strategy on the phosphonate moiety, in conjunction with the selective esterification of the carboxylic acid group. By esterifying, for example, XI with chloromethyl pivalate under basic conditions, compound XVIII is formed (FIG. 11). This affords the triester compound with a log P value of 7.100, which is too high to be used as a CNS penetrating drug. To tune the log P, compound XIX can be esterified under the same conditions to afford compound XX with a log P of 5.70 and a PSA of 126.46. This log P is at the very top of the scale, and the PSA value falls within the acceptable range, making this compound useful. Without wishing to be bound by theory, it is believed that once this triester enters the cell, cellular esterases will cleave the pivalate groups, revealing a 2-hydroxymethyl ester group that spontaneously eliminates formaldehyde to afford the active diphosphonic acid functional group. Also, again without wishing to be bound by theory, it is believed that the carboxyethyl ester will be cleaved by non-specific cellular esterases to make, ultimately, 2-n-butyl-LK-P available within the cell (inside the brain parenchymal compartment).

The variation of groups is highlighted in FIG. 11. Compound XXI can be esterified to afford a triester (XXII, log P=4.30, PSA=100.16) that should transverse the βββ and, upon the action of esterases, produce the monoethyl phosphonate (cellular esterases are not known to remove phosphonate monoesters). This activity should be comparable to compound XXI. This compound may be recognized by a βββ transport protein as it will be in the zwitterionic form at physiological pH, resembling amino acids that are substrates of, for example, the large neutral amino acid transporter (LAT1), the second most likely βββ transport mechanism following passive diffusion. Without wishing to be bound by theory, it is believed that the route through which these compounds enter the cells is passive transport.

Additionally, the benzyl ester (XXIII) can be prepared. Benzyl cysteine can be prepared from cysteine and substituted for ethyl cysteine in the synthesis, en route to compound XXIV, which has acceptable βββ properties, via XXV, which falls out of the acceptable βββ properties range. Without wishing to be bound by theory, it is believed that the double bond of the compound is reduced when deprotecting the benzyl ester of XXV or XXVI to afford XXVII and XXVIII, respectively. These compounds are more stable; the enamine functionality has the ability to hydrolyze when in the system, and the reduction to amines removes this possibility. Although these compounds have a seemingly unstable functional group, similar biological molecules have the same functional group, and, therefore, even though there is an equilibrium between the enamine, imine, and open chain forms of the compound, the presence of this functionality may lend itself to the biochemical action of the compound.

Starting with 5-cysteine retains the stereochemistry at this position, providing a stereochemically pure compound. Upon hydrogenation of the double bond, the relative stereochemistry around the 2-3 bond is cis (either on the same side, syn, or opposite side, anti, of the carboxylate group).

The phosphonate groups should be suitably protected before a reduction, such as with sodium cyanoborohydride. Many suitable phosphonate protecting groups are possible for this purpose.

The products of the ester hydrolysis (pivalic acid and formaldehyde) are toxic to cells and, as seen in XXVI, smaller ester moieties can bring the βββ properties into the acceptable range and the by-product (propanoic acid, at least) is less cytotoxic. Therefore, the propanoic esters (as in XXVI) can be synthesized to aid the biological activity.

For the lipophilic compounds (for example, XXV, XXII, or even XXI), purification by silica gel column chromatography is feasible. Otherwise, the products of the reaction are, in essence, α-amino acids (LK-Ps, LKE-Ps, LK-PE, or LKE-PEs). α-Amino carboxylic acids, although they form the basis of all proteins and play a major role in many different aspects of human biology, are not a trivial class of compounds to isolate and purify. The fact that the compounds of the present disclosure are α-amino phosphonic acids complicates their isolation and purification. These compounds (LK-Ps) are difficult, if not impossible, to purify by flash chromatography, and are not routinely extractable into organic solvents. This class of compounds is sometimes easy to purify by either anion or cation exchange chromatography, but this is not always the case. Other possible methods for isolating and purifying the compounds include, but are not limited to: 1) precipitation of the zwitterionic form of the compound out of aqueous solution; 2) cation exchange chromatography; 3) anion exchange chromatography; and 4) reverse phase flash chromatography.

As an alternative approach, cation chromatography procedures can be utilized. When attempting cation exchange chromatography, the aqueous reaction mixture is directly applied to a column of Dowex 50WX8 cation exchange resin. This strongly acidic cation exchange resin either protonates the amino functionality of the compound to be purified or exchanges the proton for the previously charged amino functionality. The column is washed with water and eluted with increasing concentrations of aqueous ammonium hydroxide. The fractions are analyzed for product, by submitting the fractions to the mass spectrometry core. If the direct addition of the reaction mixture is problematic, the pH of aqueous reaction mixture can be purposely be made basic (ca. pH 12 by the addition of aqueous sodium hydroxide; this deprotonates both the phosphonic acid and the amino group) and then the pH is readjusted by the addition of washed Dowex 50WX8 cation exchange resin. This procedure assures that all of the basic groups (phosphonates and free amino groups) were protonated by the resin and the cations formed should be retained on the column. This column is also eluted with increasing concentrations of aqueous ammonium hydroxide to displace the purified compound. Once the factions containing the product are identified, the solvent is removed by rotary evaporation or lyophilization. These solvent removal procedures may cause problems with the small molecules being produced. The removal of water, even if it is done via lyophilization, is relatively harsh and many molecules tend to decompose under these conditions. Therefore, care should be taken to avoid this possibility in every step of the reaction sequence, including removal of the solvent after purification of the new compounds. If decomposition occurs, an alternative solvent can be used. The aqueous ammonium hydroxide can be replaced with increasing concentrations of ammonia in methanol. This allows for a much gentler removal of the solvent and can prevent product decomposition.

Anion exchange is tricky with phosphonates. Since the acid is so strong, problems sometimes arise when trying to elute the compound from the column. Phosphonates are stronger acids than formic or acetic acids and, since removal of the compounds from the resin requires, in part, protonation of the phosphonate to decrease its affinity for the resin, it is sometimes difficult to remove a phosphonate using weaker carboxylic acids in the mobile phase. Protonation of the ion coordinated to the resin is not the only factor involved in ion exchange chromatography. It is often thought that bulk flow (or concentration dependence) is the driving force involved in the ion exchange process. This means that the use of an acid, even if this acid has a higher pKa value than the compound of interest coordinated to the column, can force the compound off the column if there is a high enough concentration of acid in the mobile phase. This is synonymous with removing a protein from an ion exchange column with high salt concentrations. Unfortunately, with small molecules, increasing a salt gradient is not an option because, once off the column, the small molecule must be removed from the salt for quantification purposes. With proteins, the removal of salt is less complicated due to the ability to use the process of dialysis. With this process, the salt will simply diffuse from the protein, through dialysis tubing leaving a salt free protein (in the case of peptides where secondary, tertiary and quaternary structure are inconsequential, as in proteomics) or, the elution salt can be exchanged for any choice of buffer salts and the protein can subsequently be assayed for concentration using a spectrophotometric method. This is not the case for small molecules, and one must be sure that the residue left in a flask is free of any impurities before it is to be weighed on an analytical balance for quantification. If the flask contains sodium chloride, for example, one may weigh the sample, dissolving it in $D_2O$ and recording an NMR could result in the sample looking perfectly pure. Since the salt is invisible in the NMR, the chemist can be "tricked" into thinking there is more product in the flask than there really is.

Another technique that can be employed for the purification of the α-aminophosphonates is preparative, reverse phase, flash chromatography. For example, a Yamazen "Smart Flash" Chromatography system equipped with an ultraviolet-visible spectrophotometric detector as well as an evaporative light scattering detector can be utilized for this purpose. The second detector allows for detection of compounds that do not contain a chromophoric (aromatic ring) group. This piece of equipment, along with the disposable columns containing reverse phase material, alleviates the necessity of using preparative high-performance liquid chromatography (HPLC). Although preparative HPLC is a widely used technique in the purification of amino acids, carboxylic acids, phosphonic acids and many other compounds that are highly water soluble, it has a number of limitations. Even though the term "preparative" is included in the name, the amounts of compounds that can be purified with this technique is still limited (usually under 50 mg of material) and it requires a very expensive piece of equipment dedicated to high solvent flow. Fortunately, there are many other options available for the preparation of α-aminophosphonate products.

Synthetic Optimization of Monoalkyl Phosphonates and the Synthetic Optimization of LK-P Analogues Bearing Monoalkyl Phosphonates Monoalkyl phosphonates have been synthesized and purified. A monoalkyl phosphonate moiety has been incorporated to create LK(E)-PEs (LK(E)-P mono esters) to increase the hydrophobic character of the compounds for augmented cell permeability. The monoalkyl phosphonates are suitable starting materials for the synthesis of lanthionine ketimine-phosphonate esters (LK(E)-PEs). The increased lipophilicity on the phosphonate moiety provides the compounds the ability to enter the cell more readily to approach the internal biological target. Diethyl phosphonates (compounds I), are monodealkylated with a Group I metal iodide or bromide to afford the monoalkyl phosphonates (compounds XXIX) as Group I metal salts. The first option in this synthetic sequence, as depicted in FIG. 12, Scheme 6, is the use of sodium iodide in acetone. This is a standard procedure that works well on most cases of monodealkylation of diethyl α-ketophosphonates. Typically, the sodium salts of the monoethyl α-ketophosphonates (MEAKPs, compounds XXIX) precipitate directly out of solution and can be isolated by centrifugation. Isolation by vacuum filtration is generally avoided on the first preparation of this class of compound since many of these are exceedingly hygroscopic and turn from a nice white solid in acetone to a sticky mess on filter paper when exposed to atmospheric moisture. In instances where the typical protocol is unsuccessful, the dealkylation reaction can be conducted using alternate conditions that afford this transformation including, but not limited to, lithium or potassium iodide or bromide in refluxing acetone or lithium, or sodium or potassium iodide or bromide in refluxing acetonitrile. If the salts do not precipitate out of solution, the solvent is removed under vacuum and the products are recrystallized. Sodium MEAKPs can be recrystallized from aqueous ethanol or isopropanol. If these options do not meet the standards anticipated, the compounds can be purified utilizing anion exchange chromatography techniques described above.

All of the diethyl α-ketophosphonates (compounds I) have been purified by high vacuum distillation. If the sodium MEAKP is not isolable as a solid, the compound can be protonated (desalted) by treatment with Dowex 50WX8 ion exchange resin. Once in this form, the acid form of MEAKPs (compounds XXIX, FIG. 12, Scheme 6) can be purified by silica gel flash chromatography or distillation. Optimizing purification techniques of the formed MEAKPs affords the compounds in the form necessary to be used in subsequent steps in the overall synthetic strategy (i.e., sodium pyruvate is incapable of being converted to LK utilizing the same reaction conditions where pyruvic acid is converted to LK in a highly reproducible manner). Given this knowledge, the monoalkyl phosphonates are in the acid form (XXX) and not the salt form (XXIX) for the first step of the subsequent reaction (bromination alpha to the ketone in dichloromethane solvent) to succeed. Even if the compounds are isolated as crystalline solid materials, they generally should be protonated prior to the first step towards the preparation of the LK(E)-PEs.

Figure 13:
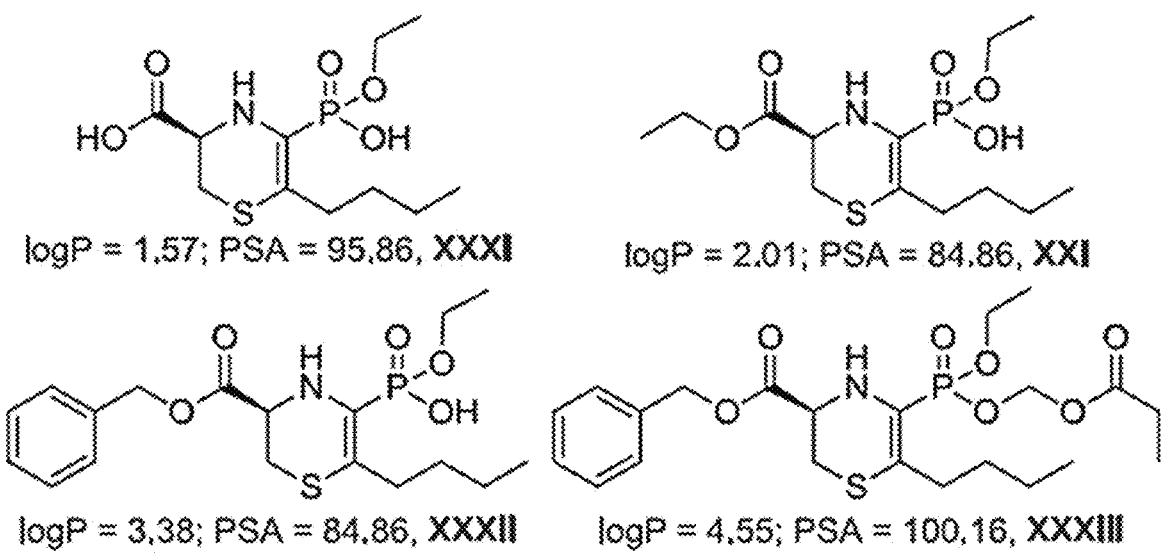
FIG. 13: Structures of non-limiting examples of LK(E)-PEEs prepared from compounds XXX.

Once prepared, the MEAKPs are subjected to the conditions described above (FIG. 6, Scheme 5) to produce LK(E)-PEs (FIG. 13). The reaction progress/completion can be monitored by UPLC-MS. Once the reaction is complete, the isolation and purification of the products can be optimized. Some of these compounds are relatively unstable. Therefore, care should be taken when optimizing procedures. The LK(E)-PEs (confirmed by UPLC-MS) can be isolated by the removal of the solvent (rotary evaporation, water bath less than 40° C. or by lyophilization) and purification by recrystallization, ion exchange chromatography, or reverse phase or normal phase flash chromatography, as described above.

Testing the LK-P and LKE-P Analogues in Quantitative Autophagy Assays

Figure 14:
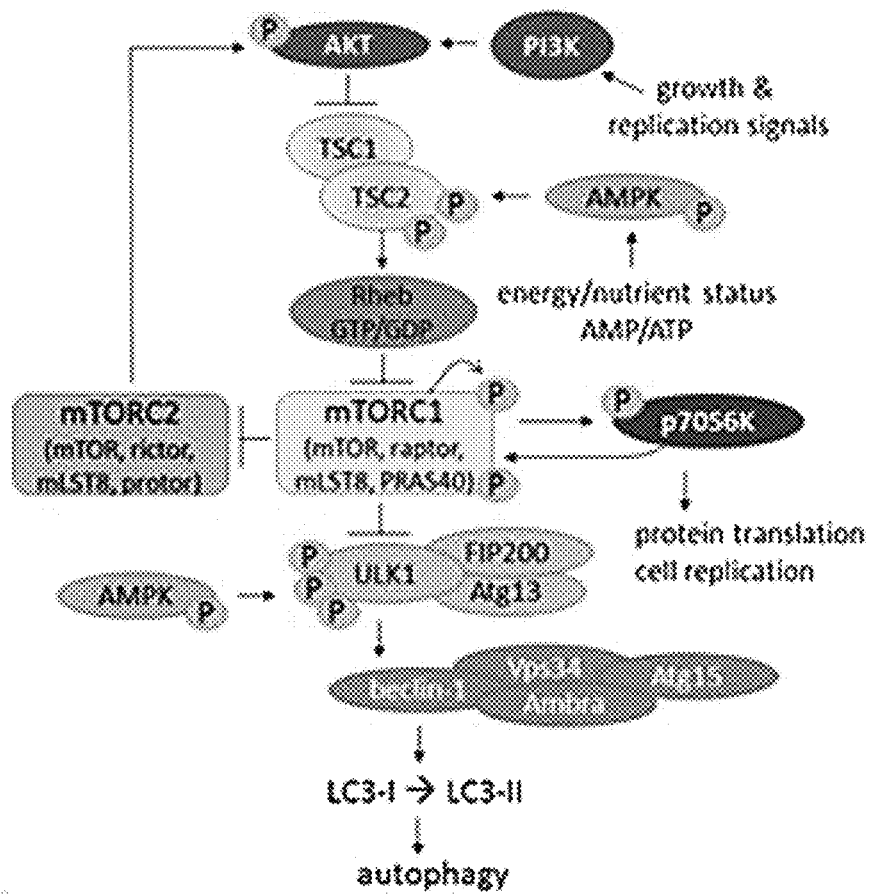
FIG. 14: Autophagy model.

Autophagy is a complex process involving many different protein components, but predominant amongst its regulatory elements are the mammalian target of rapamycin complex-1 (mTORC1) and unc-51-like kinase-1 (ULK1, FIG. 14). mTORC1 is itself a kinase that inhibits ULK1. When nutrients and cell energy are limiting, mTORC1 is suppressed by the coordinated actions of tuberous sclerosis complex (TSC) proteins 1 and 2 (TSC1/2) and Rheb (Ras homolog enriched in the brain). This allows disinhibition of ULK1, which then associates with beclin-1 protein to form pre-autophagosomal structures. Autophagosomes mature in a process marked by phosphatidylethanolamine conjugation to microtubule associated protein 1 light chain 3 (LC3-I→LC3-II conversion). After lysosomal fusion, the autophagy components are turned over and the cycle completes. One of the most reliable ways to determine whether a treatment increases true autophagy flux is to measure LC3-I to LC3-II conversion in the absence and presence of the vacuolar ATPase inhibitor bafilomycin-A1. Bafilomycin neutralizes lysosomal pH, preventing autophagosome-lysosomal fusion, and traps LC3-II at a point prior to its turnover in mature autophagolysosomes. Therefore, a manipulation that increases autophagy flux will increase LC3-II in the presence of a bafilomycin, whereas a treatment that blocks autophagy clearance will have no effect on LC3-II under these conditions. As seen from the data in FIG. 8, LK and 2-isopropyl-LK-P both increase autophagic flux.

Materials and Methods

The compounds were individually packaged in glass vials. An amount of pure compound of known mass above 10 mg (to assure accuracy when using an analytical balance) was diluted in the appropriate solvent (methanol, ethanol, acetone or another volatile solvent) to a known concentration. A known volume of this solution was then partitioned into five individual vials using a Hamilton syringe or a pipetman, and the solvent was removed under a stream of argon gas.

For the assays, rat glioma cells RG2 (ATCC® CRL-2433™; RG2 cells) were cultured. At the time of treatment, the medium in each of the dishes was replaced with medium containing vehicle (saline), LK(E)-P(E)s or LKE (dissolved in saline and neutralized) at the desired final concentrations, and equilibrated for 15 min, followed by treatment with bafilomycin-A1 in medium. The cells were then incubated for an additional 4 h. At termination, the cell culture medium was removed, cells were washed with PBS and lysed on ice in Pierce RIPA buffer containing protease and phosphatase inhibitors.

Western Blotting: The proteins were electrophoresed and wet-blotted to polyvinylidine difluoride membranes, blocked overnight in 4% bovine serum albumin, and developed using antibodies obtained from Cell Signaling Technology (LC3A: cat #. 4599; ULK1: cat #. 8054, ULK1 (p757): cat #. 6880).

Statistics: The data obtained in FIG. 9 is graphically presented as mean±SEM. In the case of single mean comparisons, data was analyzed by two-tailed unpaired t-tests or Mann-Whitney tests appropriate to data distributions. In case of multiple comparisons, data was analyzed by one- or two-way ANOVA with post-hoc Bonferroni multiple comparisons using GraphPad Prism Software (GraphPad).

Autophagic Flux Assay

RG2 glioma cells were treated without drug (first column in FIG. 8A) or 4 h with 50 nM bafilomycin-A1 (BAF), the indicated concentration of LK, or the phosphonate analog 2-isopropyl-LK-3-phosphonate. The western blot results are shown in FIG. 8A, where the lower band corresponds to LC3-II. An increase in the intensity of this band in the presence of bafilomycin-A1 indicates increased autophagic flux. With respect to this paramert, 2-isopropyl-lanthionine-ketimine-3-phosphonate was clearly more potent at 10 μM than LK was. Similar results are shown in FIG. 9 with respect to the LK-P compound 2-butyl-lanthionine-phosphonate (also referred to as 2-n-butyl-lanthionine-phosphonate or 2-n-butyl-LK-P). As seen in FIG. 9, 2-butyl-LK-P was more effective at inducing autophagic flux than, inter alia, LK-E.

Synthesis 2-butyl-LK-P (XI)

Figure 15A:
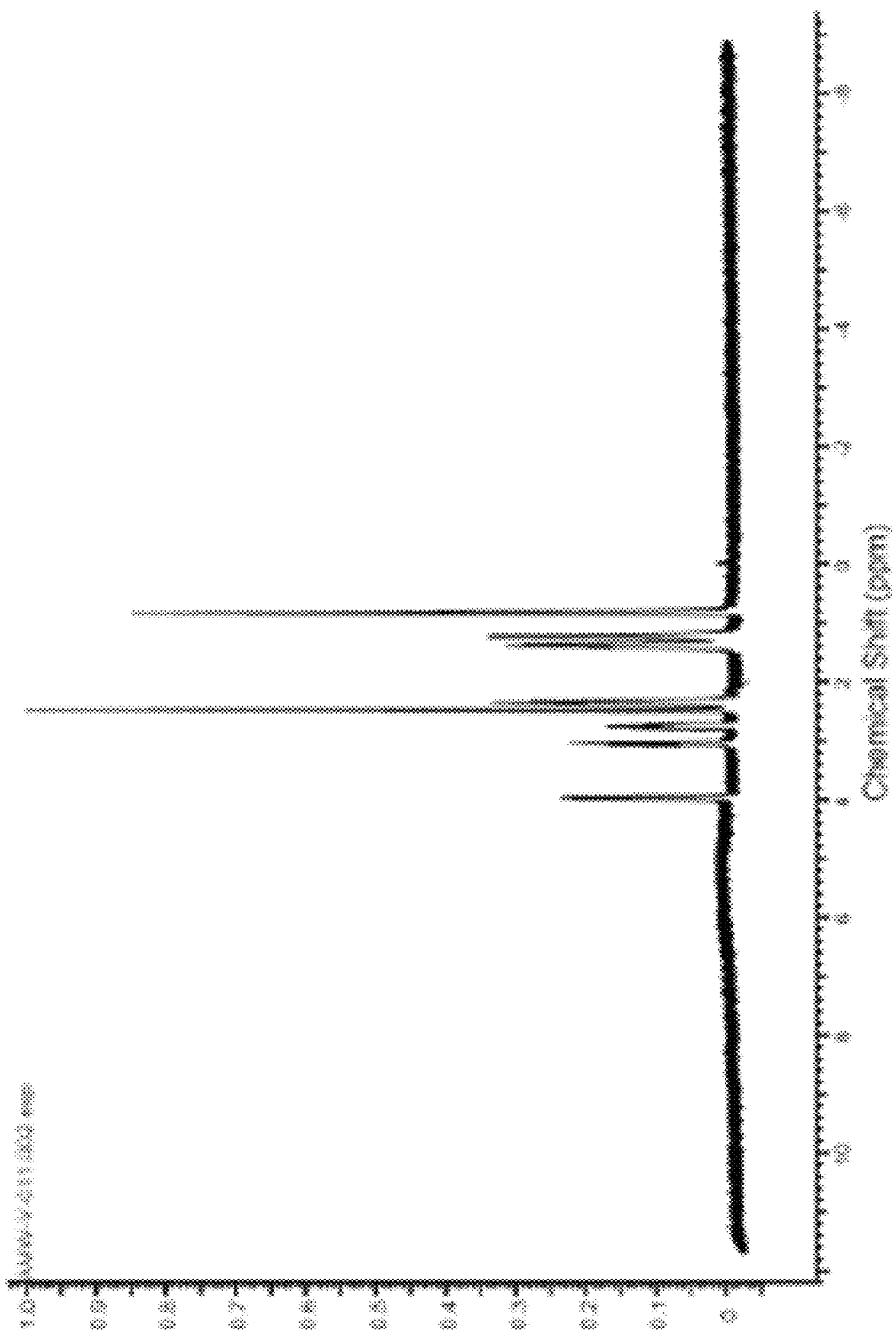
FIGS. 15A-15B: $^1$H NMR spectrum of 2-butyl-LK-P, without (FIG. 15A) and with (FIG. 15B) peak assignments.
Figure 15B:
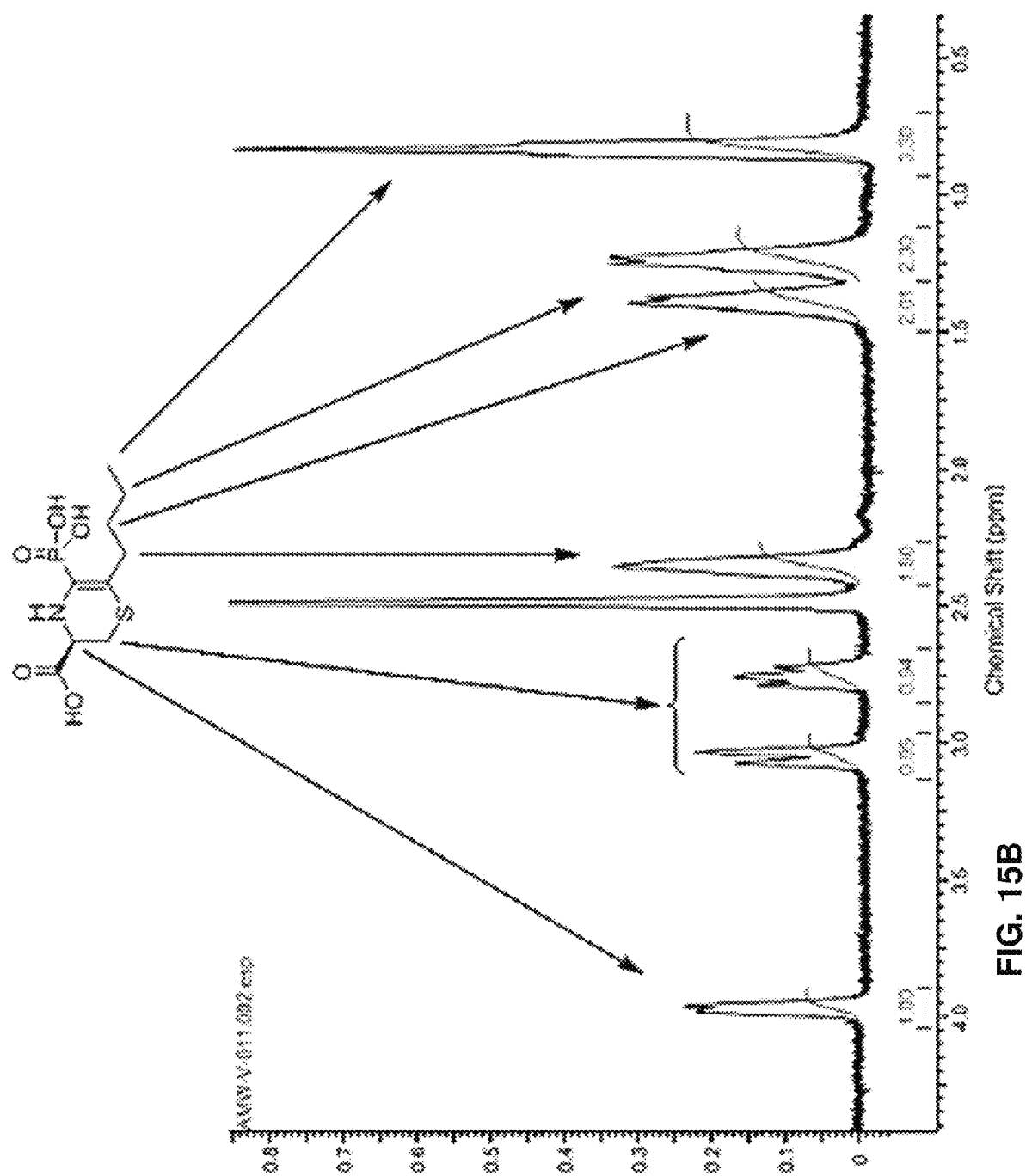
Figure 16A:
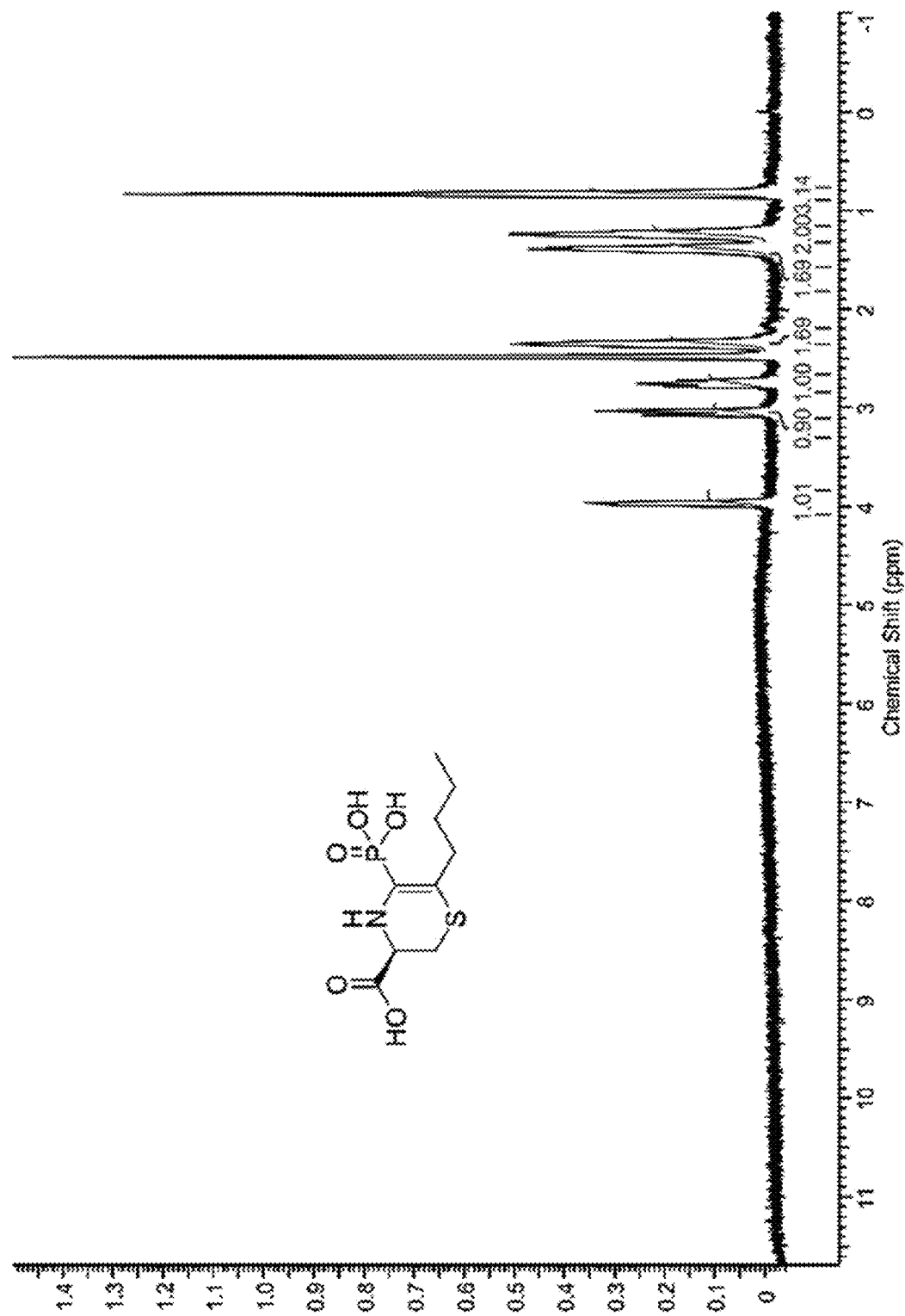
FIGS. 16A-16B: $^1$H NMR spectrum of 2-butyl-LK-P, without peak assignments, with integration values (FIG. 16A), and with peak assignments and with integration values (FIG. 16B).
Figure 16B:
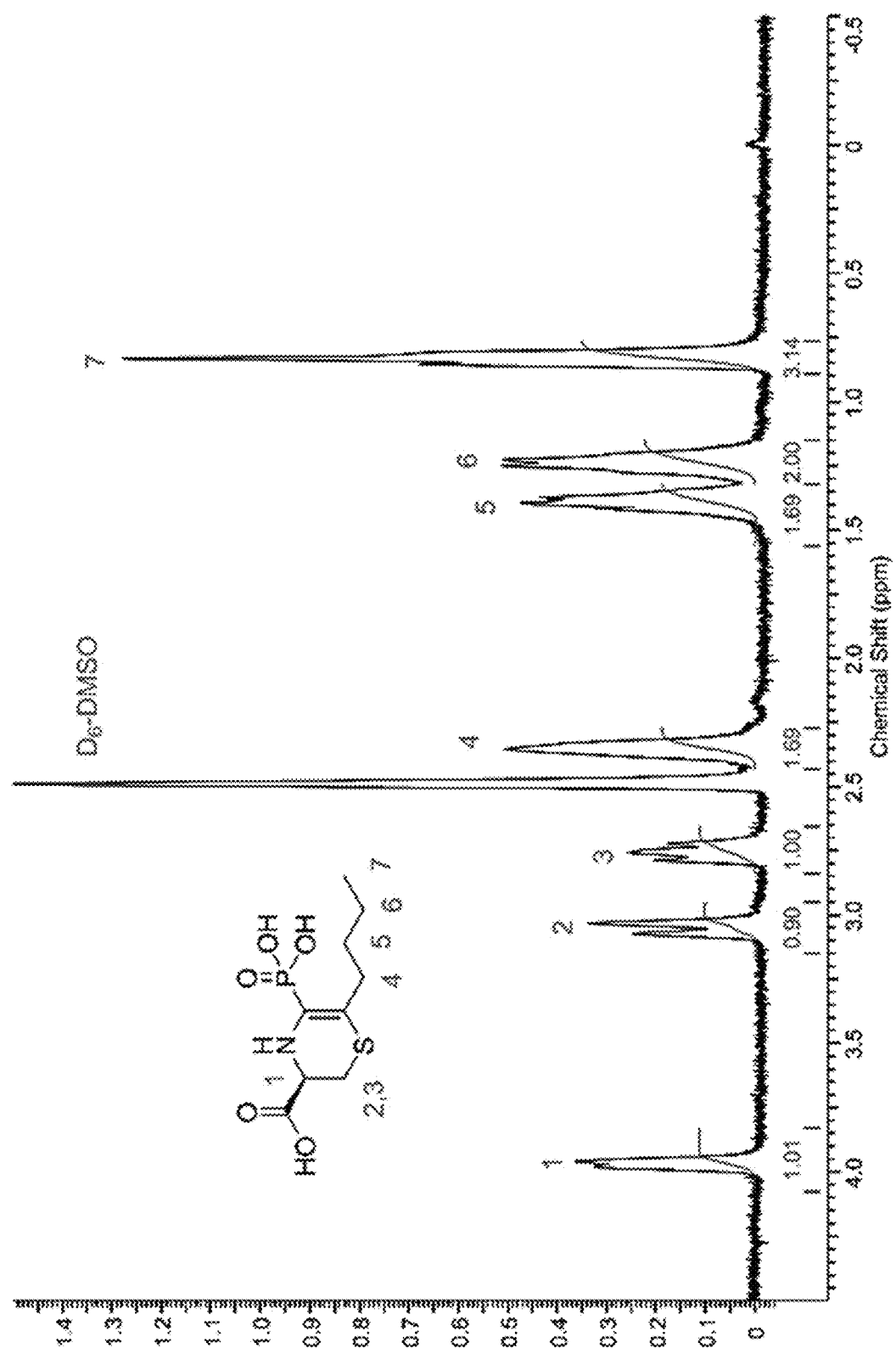
Figure 17:
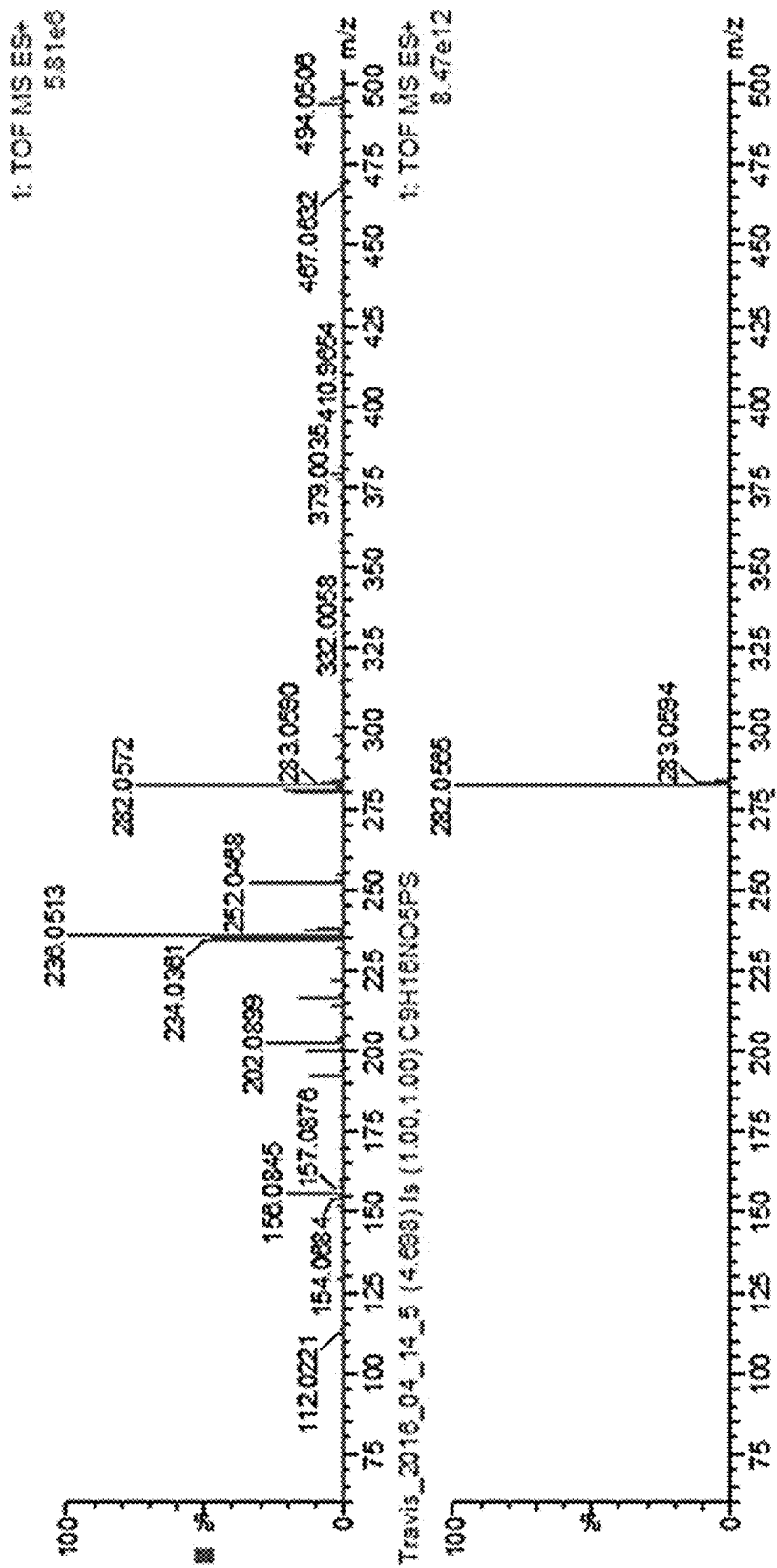
FIG. 17: HRMS spectrum of 2-n-butyl-LK-P (XI).

For exemplary purposes, the NMR and HRMS spectra of 2-butyl-LK-P, synthesized as described above, are shown in FIGS. 15-17. FIGS. 15A-15B show the $^1$H NMR spectrum of 2-butyl-LK-P, with and without peak assignments. FIGS. 16A-16B show the $^1$H NMR spectrum of 2-butyl-LK-P, with and without peak assignments. $^1$H NMR (CDCl$_3$) δ 3.96 (br. s., 1H), 3.05 (d, J=12.4 Hz, 1H), 2.84-2.66 (m, 1H), 2.36 (br. s., 2H), 1.56-1.32 (m, 2H), 1.24 (d, J=6.2 Hz, 2H), 0.89-0.77 (m, 3H); HRMS (ESI) m/z calcd for $C_9H_{17}NO_5PS$ [M+H]$^+$ 282.0565, found 282.0645. FIG. 17 shows the high-resolution mass spectrometry (HRMS) spectra of 2-butyl-LK-P. The product was isolated as a white solid and was stable to high vacuum pressures at least overnight without visual or spectral decomposition.

Synthesis 2-n-hexyl LKE-P (XIV)

Figure 18:
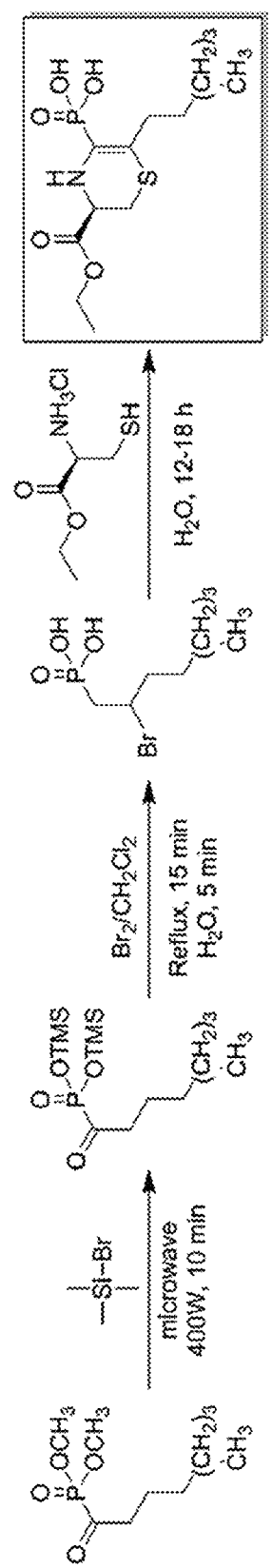
FIG. 18: Scheme showing the synthesis of 2-n-hexyl-LKE-P (XIV).
Figure 19:
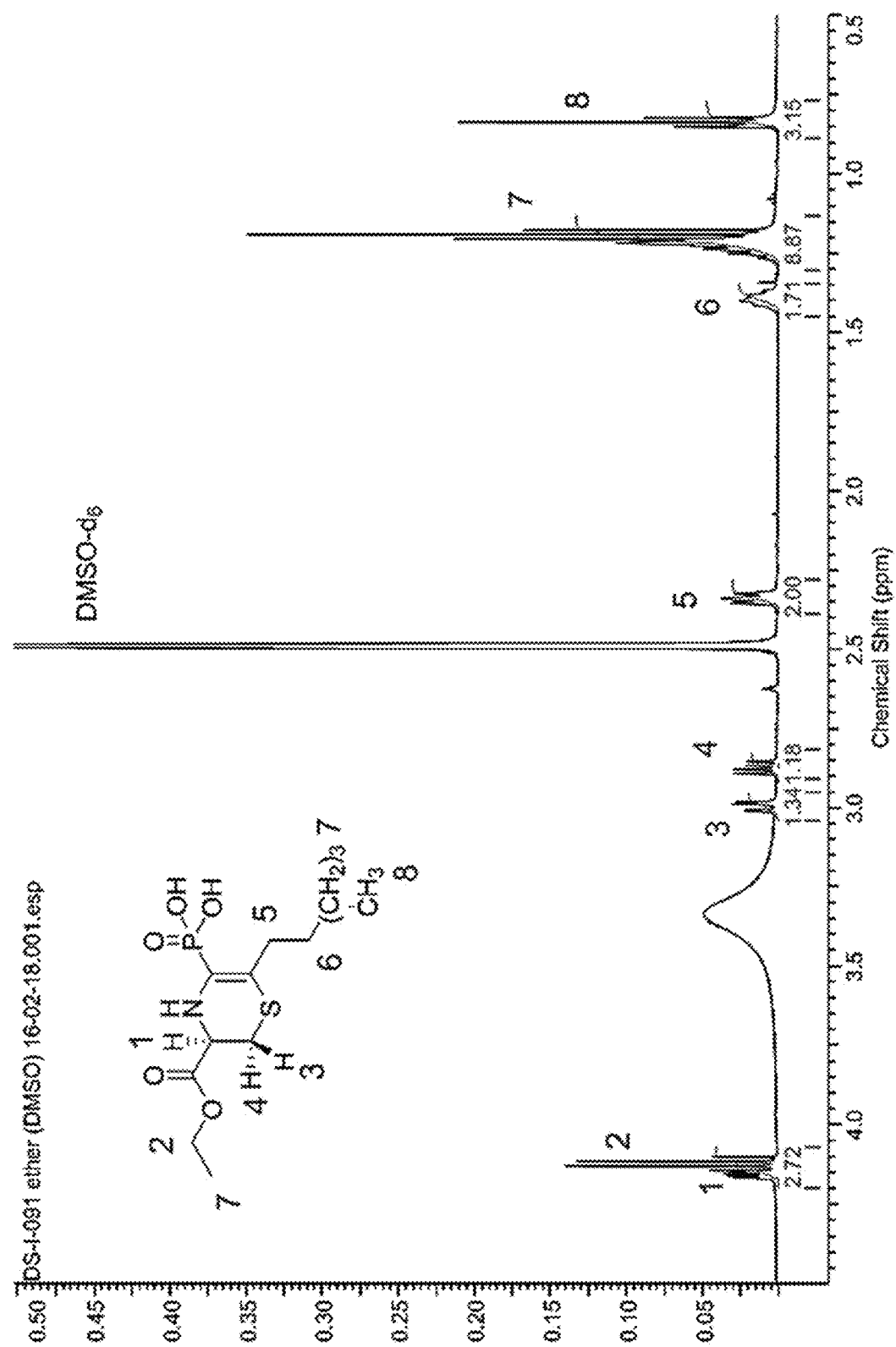
FIG. 19: $^1$H NMR spectrum of 2-n-hexyl-LKE-P (XIV).

FIG. 18 illustrates the synthesis of 2-n-hexyl-LKE-P (XIV). To a solution of DMOP (DS-I-071, 513.5 mg, 2.17 mmol), in a biotage microwave vial, was added bromotrimethylsilane (1.72 mL, 13.04 mmol). The tube was purged with argon, covered, and heated at 400 W for 10 min. The contents of the vial were transferred to a round bottom flask, the vial was washed with dichloromethane (3×3 mL), which was transferred to the flask. The solvent and excess bromotrimethylsilane were removed in vacuo. To the flask was added dichloromethane (10 mL) which was subsequently removed in vacuo to aid in the removal of any residual bromotrimethylsilane. To the flask was added dichloromethane (9 mL) and, to this solution, with stirring, was added a solution of bromine (220 μL, 4.34 mmol) in dichloromethane (3 mL). The flask was thoroughly purged with Ar(g) and the resultant solution was heated to reflux for 20 min, under an argon atmosphere, followed by the removal of the solvent and excess bromine in vacuo. The residue was dissolved in water, stirred for 5 min, followed by the addition of cysteine ethyl ester, hydrochloride (746.4 mg, 4.02 mmol) dissolved in water (3 mL). The flask was thoroughly purged with Ar(g) and the resultant solution was stirred for 12 h under an argon atmosphere. The white solid was isolated by centrifugation, triturated with water, and isolated by centrifugation (ca. 30 mL, 3×), and the residual solvent was removed in vacuo. The dry solid was tritiated with ethyl ether and isolated by centrifugation (ca. 30 mL, 3×), and the residual solvent was removed in vacuo to afford the product (60.4 mg, 8.25% yield) as a white solid: $^1$H NMR (500 MHz, DMSO-d$_6$) δ=4.20-4.05 (m, 3H), 3.00 (dd, J=3.2, 12.3 Hz, 1H), 2.87 (dd, J=6.5, 12.1 Hz, 1H), 2.39-2.28 (m, 2H), 1.46-1.35 (m, 2H), 1.29-1.14 (m, 8H), 0.89-0.77 (m, 3H); $^{13}$C NMR (125 MHz, DMSO-d$_6$) δ 218.1 (d, J$_{C-P}$) 167.1 Hz), 175.6, 62.7, 38.3 (d, J$_{C-P}$) 51.1 Hz), 27.8, 14.0; $^{31}$P NMR (202 MHz, DMSO-d$_6$) δ 3.97; HRMS calcd for $C_{13}H_{25}NO_5PS$ 338.1191, found 338.1208 ([M+H]$^+$). FIG. 19 shows the $^1$H NMR spectrum of 2-n-hexyl-LKE-P. FIG. 20 shows the UPLC chromatograms, and HRMS and UV-Vis spectra of 2-n-hexyl-LKE-P.

The 2-n-hexyl-LKE-P turned into a powdery substance but after a while little balls formed and that was what was collected (may be making liposomes and this may be what is decomposing on the vac pump), when left on the high vacuum pump overnight, turned from a white solid to an off-white/greyish solid and the NMR looks pretty good (AMW-V-015).

Synthesis of 2-benzyl LK-P (XXIX)

Figure 21:
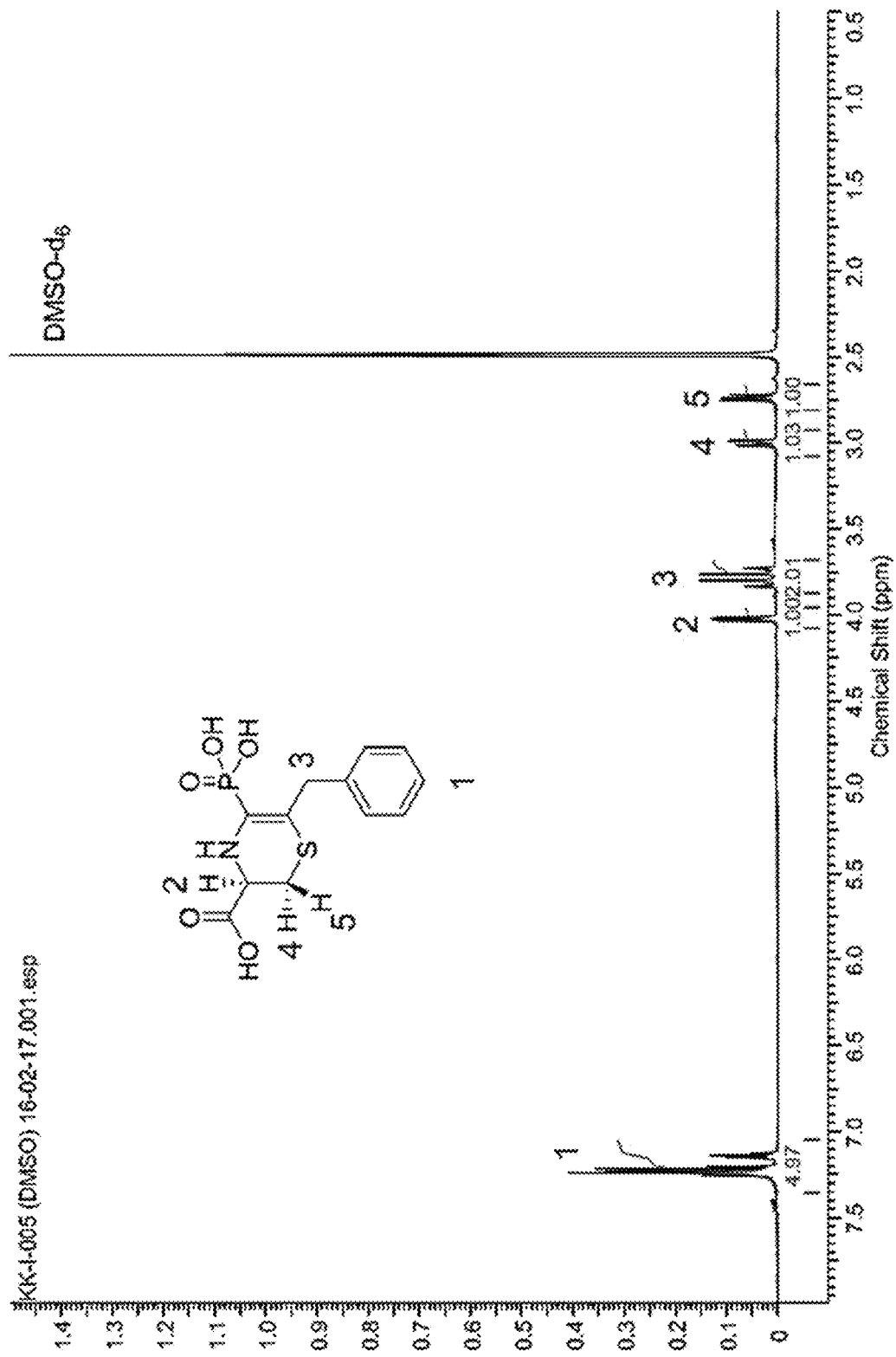
FIG. 21: $^1$H NMR spectrum of 2-benzyl-LK-P (XXIX).
Figure 22:
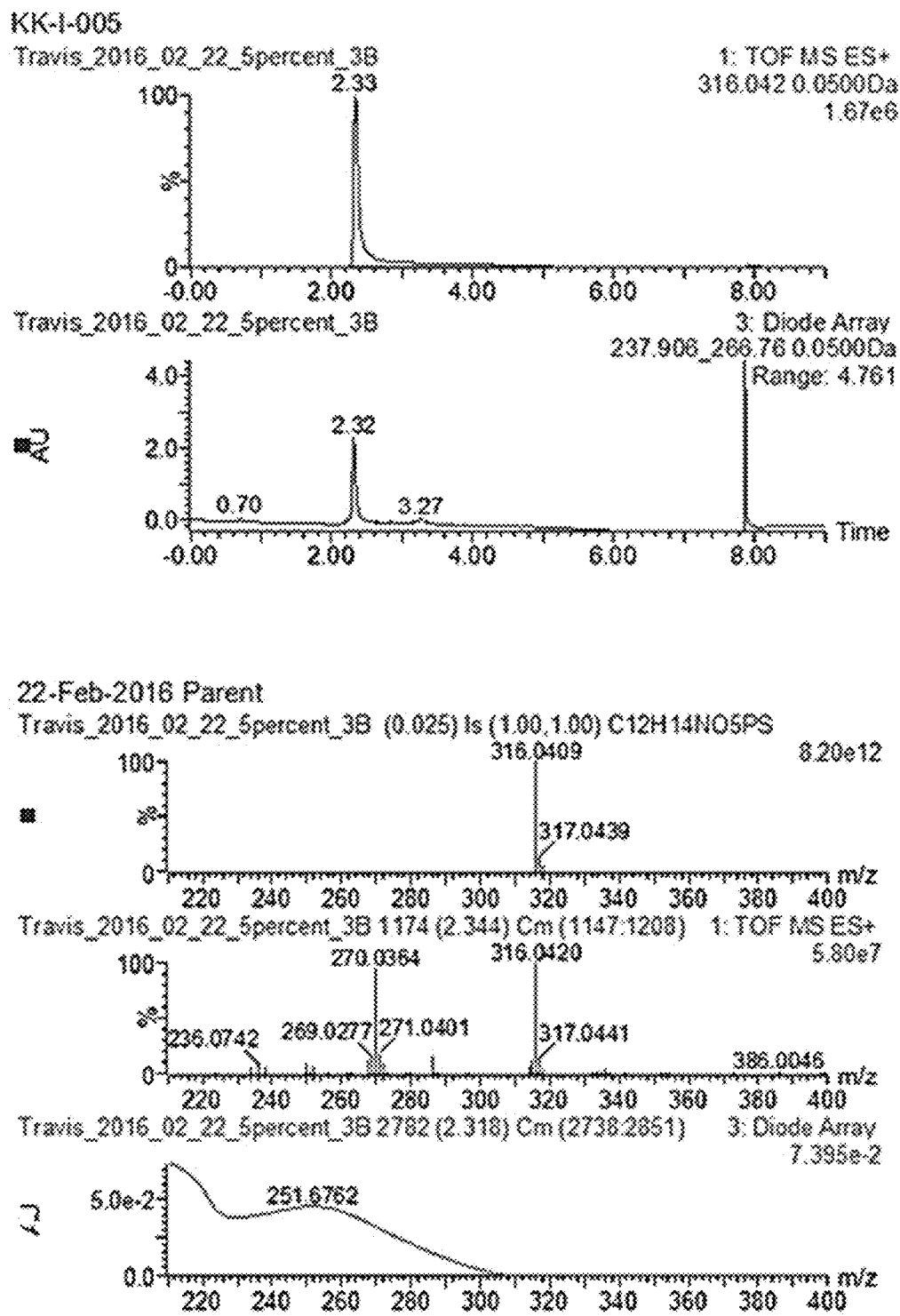
FIG. 22: UPLC chromatograms, HRMS and UV-Vis spectra of 2-benzyl-LK-P (XXIX).

To a solution of DiMethylDiHydroCinnamoylPhosphonate (DMDHCP) (513.5 mg, 2.17 mmol), in a biotage microwave vial, was added bromotrimethylsilane (1.72 mL, 13.04 mmol). The tube was purged with argon, covered and heated at 400 W for 10 min. The contents of the vial were transferred to a round bottom flask, the vial was washed with dichloromethane (3×3 mL) which was transferred to the flask. The solvent and excess bromotrimethylsilane were removed in vacuo. To the flask was added dichloromethane (10 mL) which was subsequently removed in vacuo to aid in the removal of any residual bromotrimethylsilane. To the flask was added dichloromethane (9 mL) and, to this solution, with stirring, was added a solution of bromine (220 μL, 4.34 mmol) in dichloromethane (3 mL). The flask was thoroughly purged with Ar(g) and the resultant solution was heated to reflux for 20 min, under an argon atmosphere, followed by the removal of the solvent and excess bromine in vacuo. The residue was dissolved in water, stirred for 5 min, followed by the addition of cysteine ethyl ester, hydrochloride (746.4 mg, 4.02 mmol) dissolved in water (3 mL). The flask was thoroughly purged with Ar(g) and the resultant solution was stirred for 12 h under an argon atmosphere. The white solid was isolated by centrifugation, triturated with water, and isolated by centrifugation (ca. 30 mL, 3×) and the residual solvent was removed in vacuo. The dry solid was triturated with ethyl ether and isolated by centrifugation (ca. 30 mL, 3×) and the residual solvent was removed in vacuo to afford the product (60.4 mg, 8.25% yield) as a white solid: $^1$H NMR (500 MHz, DMSO-$d_6$) δ=7.32-7.08 (m, 5H), 4.02 (dd, J=3.0, 7.4 Hz, 1H), 3.87-3.68 (m, 2H), 3.00 (dd, J=2.5, 12.3 Hz, 1H), 2.74 (dd, J=7.6, 12.3 Hz, 1H); $^{13}$C NMR (125 MHz, DMSO-$d_6$) δ 218.1 (d, JC-P) 167.1 Hz), 175.6, 62.7, 38.3 (d, $J_{C-P}$) 51.1 Hz), 27.8, 14.0; $^{31}$P NMR (202 MHz, DMSO-$d_6$) δ 3.97; HRMS calcd for $C_{12}H_{15}NO_5PS$ 316.0409, found 316.0420 ([M+H]$^+$). FIG. 21 shows the $^1$H NMR spectrum of 2-benzyl-LK-P. FIG. 22 shows the UPLC chromatograms, and HRMS and UV-Vis spectra of 2-benzyl-LK-P.

Alternate Synthesis of 2-benzyl-LK-P

To a solution of DiMethylDiHydroCinnamoylPhosphonate (DMDHCP) (667.8 mg, 2.76 mmol) in a biotage microwave vial was added bromotrimethylsilane (2.180 mL, 16.54 mmol). The tube was purged with argon, covered, and heated under microwave irradiation at 100° C. for 10 min. The contents of the vial were cooled to rt and transferred to a round bottom flask, and the vial was washed with dichloromethane (3×3 mL) which was subsequently transferred to the flask. The solvent and excess bromotrimethylsilane were removed in vacuo. To the flask was added dichloromethane (10 mL) which was subsequently removed in vacuo to aid in the removal of any residual bromotrimethylsilane followed by the addition of dichloromethane (9 mL) and, to this solution, with stirring, was added a solution of bromine (320. μL, 6.34 mmol) in dichloromethane (3 mL). The flask was thoroughly purged with Ar(g) and the resultant solution was heated to reflux for 20 min, under an argon atmosphere, followed by the removal of the solvent and excess bromine in vacuo. The residue was dissolved in water, stirred for 5 min, followed by the addition of hydrochloride (560.4 mg, 3.17 mmol) dissolved in water (3 mL). The flask was thoroughly purged with Ar(g) and the resultant solution was stirred for 12 h under a blanket of argon(g). The white solid was isolated by centrifugation, the supernatant was discarded, the precipitate was triturated with water and isolated by centrifugation (ca. 30 mL, 3×), and the residual solvent was removed in vacuo. The dry, solid, colored material was triturated with ethyl ether and isolated by centrifugation (ca. 30 mL, 3×), and the residual solvent was removed in vacuo to afford the product (291.2 mg, 29.1% yield) as a brown solid: $^1$H NMR (500 MHz, DMSO-$d_6$) δ=7.32-7.08 (m, 5H), 4.02 (dd, J=3.0, 7.4 Hz, 1H), 3.87-3.68 (m, 2H), 3.00 (dd, J=2.5, 12.3 Hz, 1H), 2.74 (dd, J=7.6, 12.3 Hz, 1H); $^{13}$C NMR (125 MHz, DMSO-$d_6$) δ 218.1 (d, JC-P) 167.1 Hz), 175.6, 62.7, 38.3 (d, $J_{C-P}$) 51.1 Hz), 27.8, 14.0; $^{31}$P NMR (202 MHz, DMSO-$d_6$) δ 3.97; HRMS calcd for $C_{12}H_{15}NO_5PS$ 316.0409, found 316.0420 ([M+H]$^+$).

Synthesis of 2-phenyl-LK-P (XXX)

Figure 23:
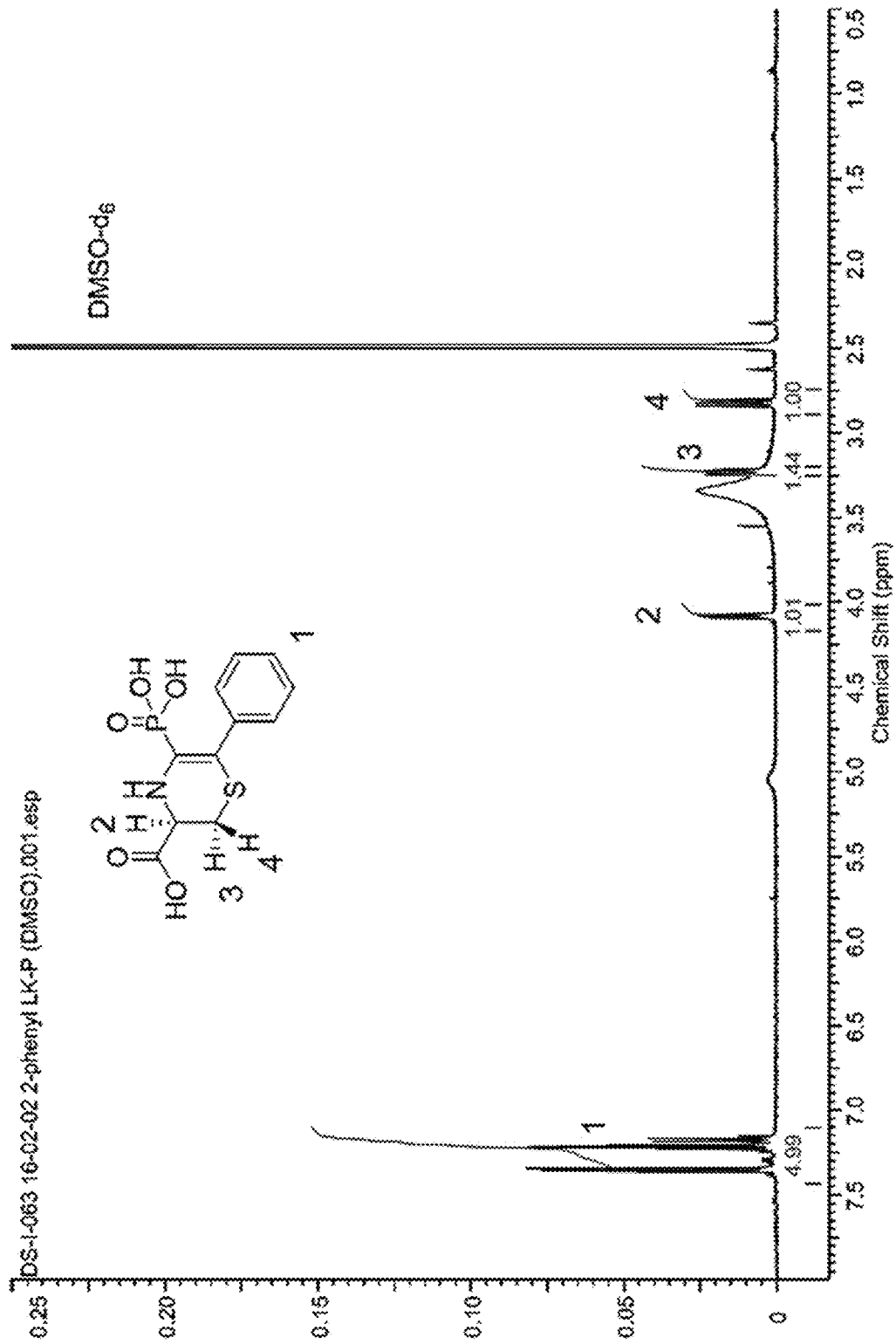
FIG. 23: $^1$H NMR spectrum of 2-phenyl-LK-P (XXX).

To a solution of DiMethylPhenylAcetylphosphonate (DMPAP) (496.4 mg, 1.72 mmol) in a biotage microwave vial, was added bromotrimethylsilane (1.360 mL, 10.32 mmol). The tube was purged with argon, covered, and heated under microwave irradiation at 100° C. for 10 min. The contents of the vial were cooled to rt and transferred to a round bottom flask, and the vial was washed with dichloromethane (3×3 mL) which was subsequently transferred to the flask. The solvent and excess bromotrimethylsilane were removed in vacuo. To the flask was added dichloromethane (10 mL) which was subsequently removed in vacuo to aid in the removal of any residual bromotrimethylsilane followed by the addition of dichloromethane (9 mL) and, to this solution, with stirring, was added a solution of bromine (180. μL, 3.44 mmol) in dichloromethane (3 mL). The flask was thoroughly purged with Ar(g), and the resultant solution was heated to reflux for 20 min, under an argon atmosphere, followed by the removal of the solvent and excess bromine in vacuo. The residue was dissolved in water, stirred for 5 min, followed by the addition of cysteine hydrochloride (302.1 mg, 1.72 mmol) dissolved in water (3 mL). The flask was thoroughly purged with Ar(g) and the resultant solution was stirred for 12 h under a blanket of argon(g). The solid was isolated by centrifugation, the supernatant was discarded, the precipitate was triturated with water and isolated by centrifugation (ca. 30 mL, 3×), and the residual solvent was removed in vacuo. The dry, solid, colored material was triturated with ethyl ether and isolated by centrifugation (ca. 30 mL, 3×), and the residual solvent was removed in vacuo to afford the product (14.7 mg, 2.84% yield) as a light brown solid: $^1$H NMR (500 MHz, DMSO-$d_6$) δ=7.43-7.13 (m, 5H), 4.09 (dd, J=2.8, 7.9 Hz, 1H), 3.26-3.21 (m, 1H), 2.83 (dd, J=8.0, 12.1 Hz, 1H); $^{13}$C NMR (125 MHz, DMSO-$d_6$) δ 218.1 (d, JC-P) 167.1 Hz), 175.6, 62.7, 38.3 (d, $J_{C-P}$) 51.1 Hz), 27.8, 14.0; $^{31}$P NMR (202 MHz, DMSO-$d_6$) δ 3.97; HRMS calcd for $C_{11}H_{13}NO_5PS$ 302.0252, found 302.0266 ([M+H]$^+$). FIG. 23 shows the $^1$H NMR spectrum of the 2-phenyl-LK-P. FIG. 24 shows the UPLC chromatograms, HRMS, and UV-Vis spectra of 2-phenyl-LK-P.

2-hexanyl-LK-P (XIII)

Figure 25:
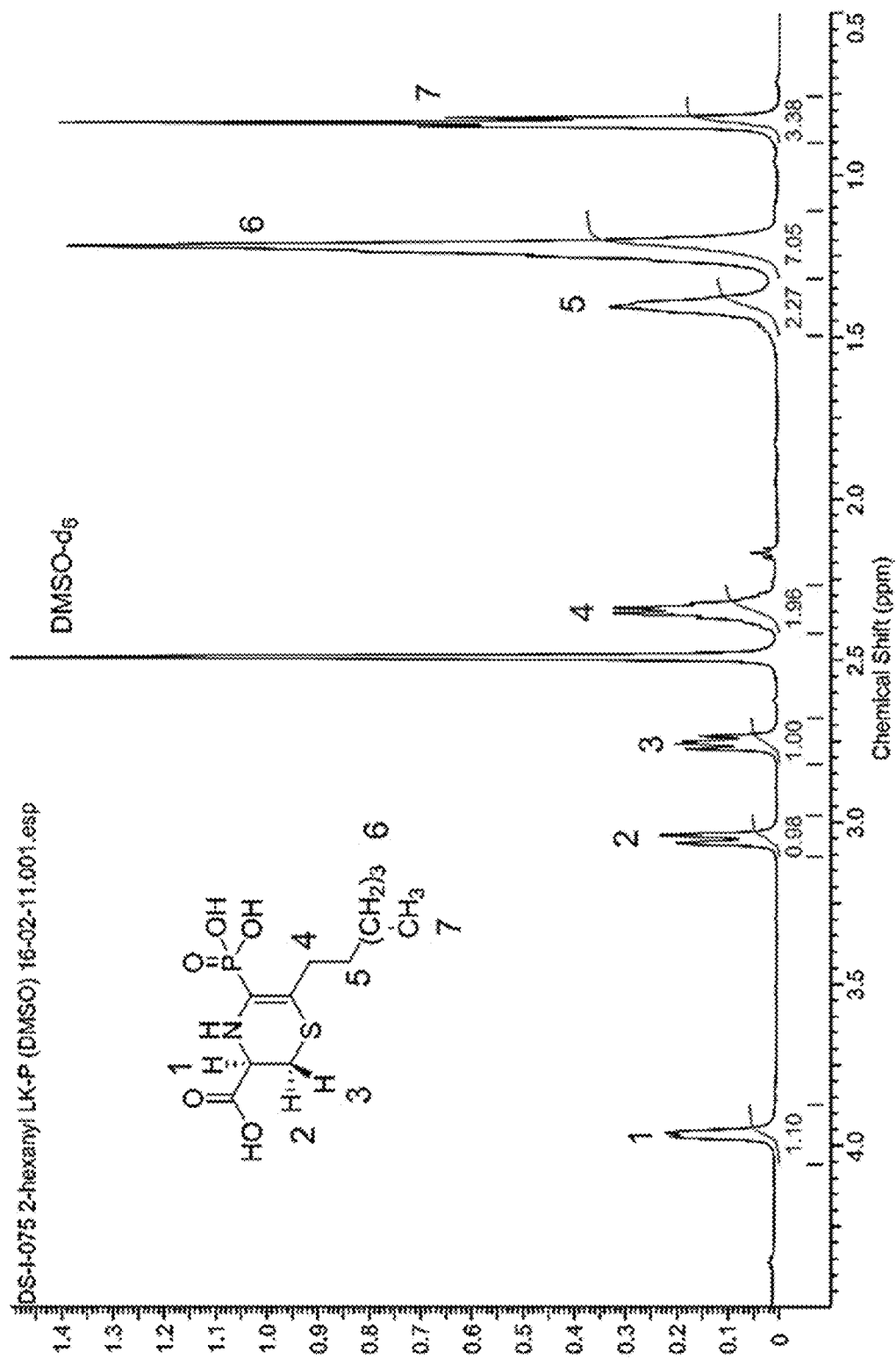
FIG. 25: $^1$H NMR spectrum of 2-n-hexyl-LK-P (XIII).

2-hexanyl-LK-P was synthesized. FIG. 25 shows the $^1$H NMR spectrum of the 2-hexanyl-LK-P. FIG. 26 shows the UPLC chromatograms, and HRMS and UV-Vis spectra of 2-hexanyl-LK-P.

Synthesis of 2-isopropyl-LK-P (IX)

Figure 27:
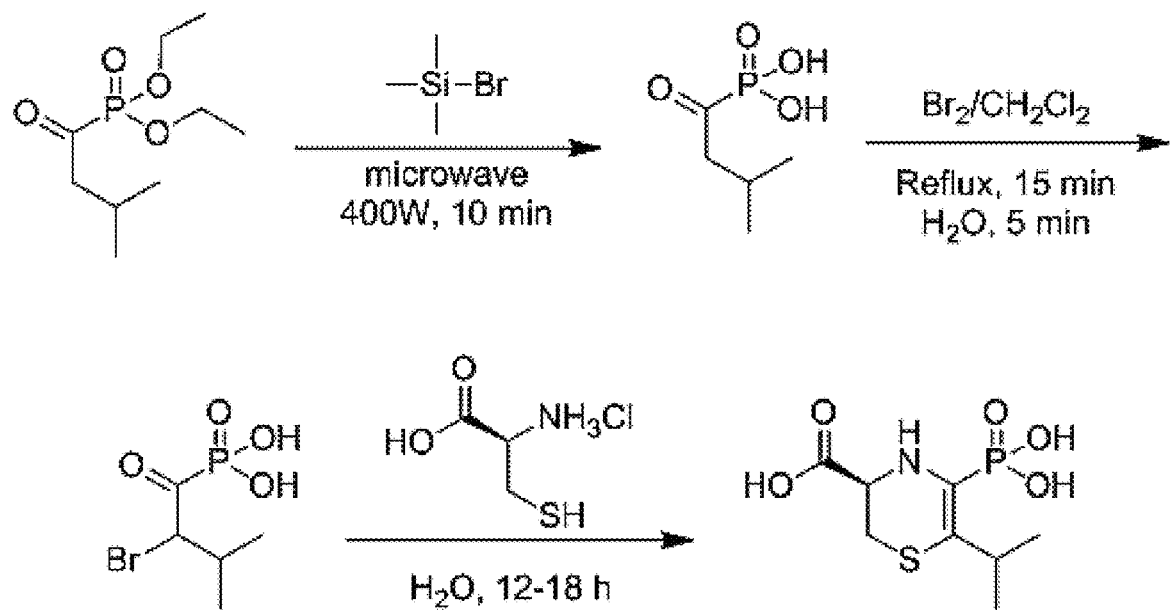
FIG. 27: Scheme showing the synthesis of 2-isopropyl-LK-P (IX).

2-isopropyl-LK-P was synthesized according to the scheme shown in FIG. 27. Briefly, to a solution of DEIVP (500.0 mg, 2.222 mmol), in a biotage microwave vial, was added bromotrimethylsilane (1.333 mL, 2.222 mmol). The tube was purged with argon, covered and heated at 400 W for 10 min. The contents of the vial were transferred to a round bottom flask, the vial was washed with dichloromethane (3×3 mL) which was transferred to the flask. The solvent and excess bromotrimethylsilane were removed in vacuo. To the flask was added dichloromethane (10 mL), which was subsequently removed in vacuo to aid in the removal of any residual bromotrimethylsilane. To the flask was added dichloromethane (9 mL) and, to this solution, with stirring, was added a solution of bromine (333 mL, 2222 mmol) in dichloromethane (3 mL). The resultant solution was heated to reflux for 15 min and the solvent was removed in vacuo. The residue was dissolved in water, stirred for 5 min followed by the addition of cysteine dissolved in water (3 mL), and the resultant solution was stirred O/N (12-18 h). The white solid was isolated by vacuum filtration, washed with water followed by acetone followed by diethyl ether to afford the product as a white solid. The product was stable to high vacuum pressures at least overnight without visual or spectral decomposition.

Synthesis of 2-isopropyl LKE-P (X)

Figure 28:
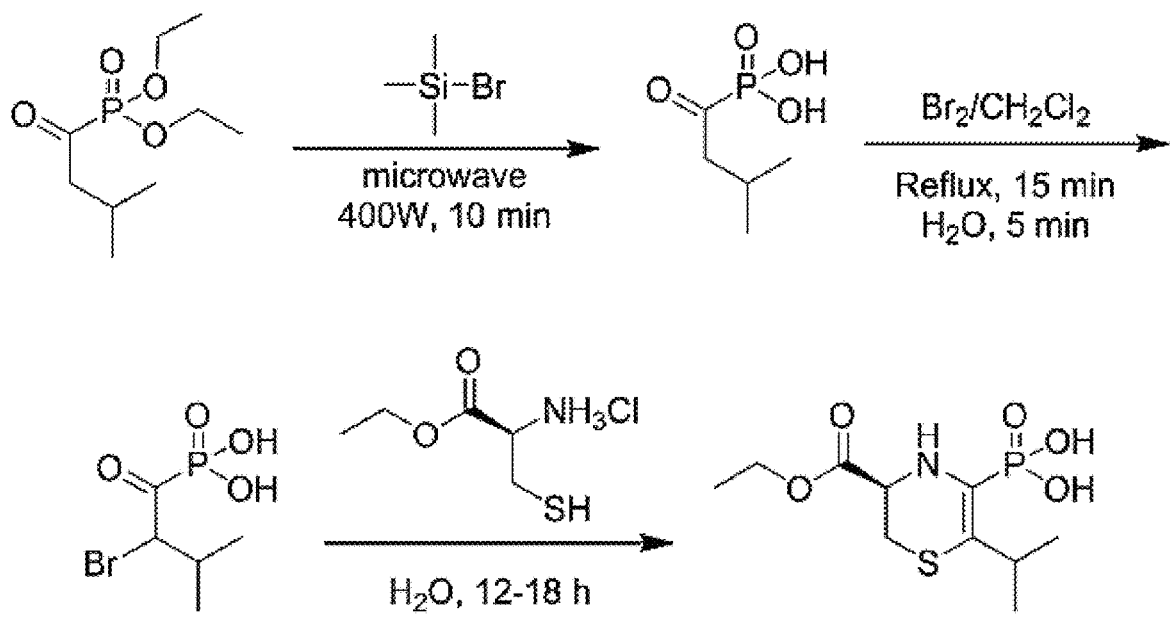
FIG. 28: Scheme showing the synthesis of 2-isopropyl-LKE-P (X).

2-isopropyl-LKE-P was synthesized according to the scheme shown in FIG. 28. Briefly, to a solution of DEIVP (500.0 mg, 2.222 mmol), in a biotage microwave vial, was added bromotrimethylsilane (1.333 mL, 2.222 mmol). The tube was purged with argon, covered and heated at 400 W for 10 min. The contents of the vial were transferred to a round bottom flask, the vial was washed with dichloromethane (3×3 mL) which was transferred to the flask. The solvent and excess bromotrimethylsilane were removed in vacuo. To the flask was added dichloromethane (10 mL) which was subsequently removed in vacuo to aid in the removal of any residual bromotrimethylsilane. To the flask was added dichloromethane (9 mL) and, to this solution, with stirring, was added a solution of bromine (333 mL, 2222 mmol) in dichloromethane (3 mL). The resultant solution was heated to reflux for 15 min and the solvent was removed in vacuo. The residue was dissolved in water, stirred for 5 min followed by the addition of cysteine dissolved in water (3 mL) and the resultant solution was stirred O/N (12-18 h). The white solid was isolated by vacuum filtration, washed with water followed by acetone followed by diethyl ether to afford the product as a white solid.

Synthesis of 2-isopropyl AECK-P

Figure 29:
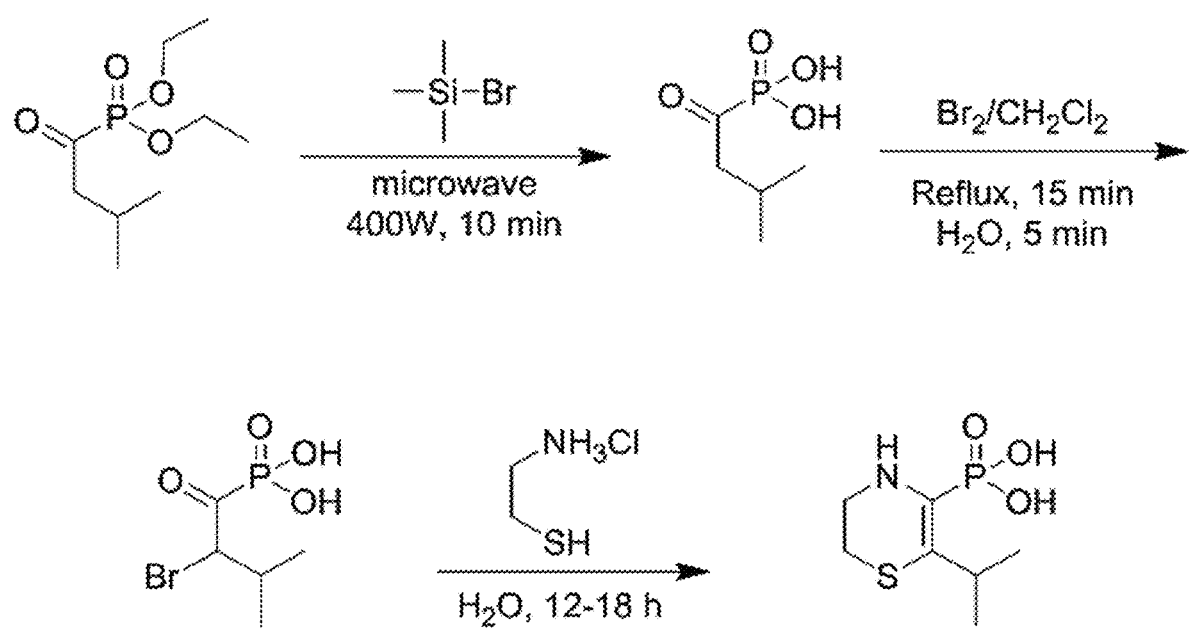
FIG. 29: Scheme showing the synthesis of 2-isopropyl AECK-P.

FIG. 29 shows the synthesis of 2-isopropyl AECK-P. To a solution of DEIVP (500.0 mg, 2.222 mmol), in a biotage microwave vial, was added bromotrimethylsilane (1.333 mL, 2.222 mmol). The tube was purged with argon, covered and heated under Biotage program number 1. The contents of the vial were transferred to a round bottom flask and the vial was washed with dichloromethane and transferred to the flask (3×3 mL). The solvent and excess bromotrimethylsilane were removed in vacuo. To the flask was added dichloromethane (10 mL) which was subsequently removed in vacuo. To the flask was added dichloromethane (9 mL) and, to this solution, with stirring, was added a solution of bromine (333 mL, 2222 mmol) in dichloromethane (3 mL). The resultant solution was heated to reflux for 15 min and the solvent was removed in vacuo. The residue was dissolved in water, stirred for 5 min, followed by the addition of cysteine dissolved in water (3 mL), and the resultant solution was stirred O/N (12-18 h). The white solid was isolated by vacuum filtration, washed with water followed by acetone followed by diethyl ether to afford the product as a white solid.

2-n-hexyl-LK-P

The 2-n-hexyl-LK-P product turned into a powdery substance without visual or spectral decomposition. This corresponds to the 2-octyl LK-P as it immediately precipitates as a large wax-like ball which almost stopped the stir bar. However, the product turned to a pink wax-like substance on the high vac, indicating this may make it decompose.

Alternate Synthesis of 2-isopropyl-LK-P

Figure 31:
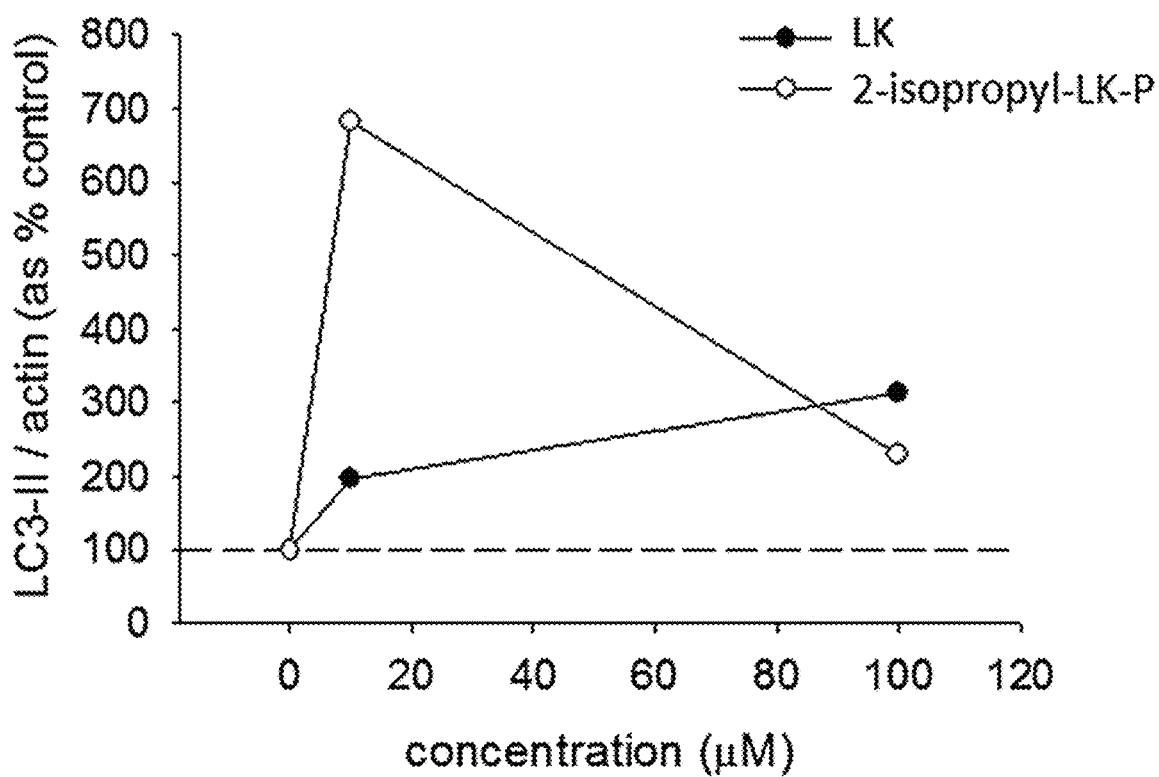
FIG. 31: C2-alkyl derivatives of LK-phosphonates activate cellular autophagy.

To a solution of DiMethylIsoValerylPhosphonate (DMIVP) (690.5 mg, 3.56 mmol), in a biotage microwave vial, was added bromotrimethylsilane (2.82 mL, 21.36 mmol). The tube was purged with argon, covered, and heated under microwave irradiation at 100° C. for 10 min. The contents of the vial were cooled to rt and transferred to a round bottom flask. The vial was washed with dichloromethane (3×3 mL) which was subsequently transferred to the flask. The solvent and excess bromotrimethylsilane were removed in vacuo. To the flask was added dichloromethane (10 mL), which was subsequently removed in vacuo to aid in the removal of any residual bromotrimethylsilane followed by the addition of dichloromethane (9 mL) and, to this solution, with stirring, was added a solution of bromine (360. µL, 7.12 mmol) in dichloromethane (3 mL). The flask was thoroughly purged with Ar(g) and the resultant solution was heated to reflux for 20 min, under an argon atmosphere, followed by the removal of the solvent and excess bromine in vacuo. The residue was dissolved in water, stirred for 5 min, followed by the addition of cysteine hydrochloride (641.7 mg, 3.556 mmol) dissolved in water (3 mL). The flask was thoroughly purged with Ar(g) and the resultant solution was stirred for 12 h under a blanket of argon(g). The white solid was isolated by centrifugation, the supernatant was discarded, and the precipitate was triturated with water and isolated by centrifugation (ca. 30 mL, 3×), and the residual solvent was removed in vacuo. The dry, solid, colored material was triturated with ethyl ether and isolated by centrifugation (ca. 30 mL, 3×), and the residual solvent was removed in vacuo to afford the product (137.2 mg, 14.4% yield) as a white solid: $^1$H NMR (500 MHz, DMSO-$d_6$) δ=3.98 (dd, J=2.8, 7.9 Hz, 1H), 3.38 (td, J=6.7, 13.5 Hz, 1H), 3.01 (dd, J=2.7, 12.1 Hz, 1H), 2.64 (dd, J=7.9, 12.3 Hz, 1H), 0.97 (t, J=6.9 Hz, 6H); $^{13}$C NMR (125 MHz, DMSO-$d_6$) δ 218.1 (d, JC-P), 167.1 Hz), 175.6, 62.7, 38.3 (d, $J_{C-P}$ 51.1 Hz), 27.8, 14.0; $^{31}$P NMR (202 MHz, DMSO-$d_6$) δ 3.97; HRMS calcd for $C_8H_{15}NO_5PS$ 268.0409, found 268.0410 ([M+H]$^+$). The activity of 2-isopropyl-LK-P prepared in this example is shown in FIGS. 8, 31.

Synthesis of 2-n-butyl-LK-P

To a solution of DiMethylHexanoylPhosphonate (DMHP) (608.5 mg, 3.66 mmol), in a biotage microwave vial, was added bromotrimethylsilane (2.42 mL, 18.3 mmol). The tube was purged with argon, covered, and heated under microwave irradiation at 100° C. for 10 min. The contents of the vial were cooled to rt and transferred to a round bottom flask, and the vial was washed with dichloromethane (3×3 mL) which was subsequently transferred to the flask. The solvent and excess bromotrimethylsilane were removed in vacuo. To the flask was added dichloromethane (10 mL) which was subsequently removed in vacuo to aid in the removal of any residual bromotrimethylsilane followed by the addition of dichloromethane (9 mL) and, to this solution, with stirring, was added a solution of bromine (370. µL, 7.32 mmol) in dichloromethane (3 mL). The flask was thoroughly purged with Ar(g) and the resultant solution was heated to reflux for 20 min, under an argon atmosphere, followed by the removal of the solvent and excess bromine in vacuo. The residue was dissolved in water, stirred for 5 min, followed by the addition of cysteine hydrochloride (639.2 mg, 3.639 mmol) dissolved in water (3 mL). The flask was thoroughly purged with Ar(g) and the resultant solution was stirred for 12 h under a blanket of argon(g). The white solid was isolated by centrifugation, the supernatant was discarded, the precipitate was triturated with water and isolated by centrifugation (ca. 30 mL, 3×), and the residual solvent was removed in vacuo. The dry, solid, colored, material was triturated with ethyl ether and isolated by centrifugation (ca. 30 mL, 3×) and the residual solvent was removed in vacuo to afford the product (88.1 mg, 16.3% yield) as a white solid: $^1$H NMR (500 MHz, DMSO-$d_6$) 5=3.98 (dd, J=2.8, 7.9 Hz, 1H), 3.38 (td, J=6.7, 13.5 Hz, 1H), 3.01 (dd, J=2.7, 12.1 Hz, 1H), 2.64 (dd, J=7.9, 12.3 Hz, 1H), 0.97 (t, J==6.9 Hz, 6H); $^{13}$C NMR (125 MHz, DMSO-$d_6$) δ 218.1 (d, JC-P) 167.1 Hz), 175.6, 62.7, 38.3 (d, $J_{C-P}$) 51.1 Hz), 27.8, 14.0; $^{31}$P NMR (202 MHz, DMSO-$d_6$) δ 3.97; HRMS calcd for $C_9H_{17}NO_5PS$ 282.0565, found 282.0572 ([M+H]$^+$).

Synthesis of 2-n-butyl-LKE-P

To hexanoyl chloride (3.233 g, 24.02 mmol) in a round bottom flask, cooled by an external ice bath, was added trimethylphosphite (2.278 g, 26.42 mmol) at a rate to prevent boiling of the flask contents. Upon completion of the addition, the flask was purged with argon, covered, and allowed to stir at ambient temperature overnight (ca. 16 h). The chloromethane and excess trimethylphosphite were removed in vacuo and to the resultant oil, under a blanket of argon(g), was added bromotrimethylsilane (15.85 mL, 120.1 mmol). The flask was purged with argon, covered, and allowed to stir at ambient temperature overnight (ca. 16 h). The solvent and excess bromotrimethylsilane were removed in vacuo. To the flask was added dichloromethane (10 mL), which was subsequently removed in vacuo to aid in the removal of any residual bromotrimethylsilane followed by the addition of dichloromethane (10 mL). To this solution, with stirring, was added a solution of bromine (2.46 mL, 48.0 mmol) in dichloromethane (5 mL). The flask was thoroughly purged with Ar(g), and the resultant solution was heated to reflux for one hour, under an argon atmosphere, followed by the removal of the solvent and excess bromine in vacuo. The residue was dissolved in 200 mL of 5% sodium bisulfite, stirred for 5 min, followed by the addition of a solution of cysteine ethyl ester, hydrochloride (4.461 g, 24.02 mmol) dissolved in 5% sodium bisulfite (10 mL). The flask was thoroughly purged with Ar(g) and the resultant solution was stirred for 12 h under a blanket of argon(g). The white solid was isolated by centrifugation, the supernatant was discarded, the precipitate was triturated with water and isolated by centrifugation (ca. 30 mL, 3×), and the residual solvent was removed in vacuo. The dry, solid, colored material was triturated with ethyl ether and isolated by centrifugation (ca. 30 mL, 3×) and the residual solvent was removed in vacuo to afford the product (3.3463 g, 45.07% yield) as a white solid: $^1$H NMR (500 MHz, DMSO-$d_6$) δ=4.21-4.06 (m, 3H), 3.00 (dd, J=2.7, 12.5 Hz, 1H), 2.88 (dd, J=6.3, 12.3 Hz, 1H), 2.42-2.27 (m, 2H), 1.47-1.33 (m, 2H), 1.29-1.14 (m, 5H), 0.83 (t, J=7.4 Hz, 3H); $^{13}$C NMR (125 MHz, DMSO-$d_6$) δ 218.1 (d, JC-P) 167.1 Hz), 175.6, 62.7, 38.3 (d, $J_{C-P}$) 51.1 Hz), 27.8, 14.0; $^{31}$P NMR (202 MHz, DMSO-$d_6$) δ 3.97; HRMS calcd for $C_{11}H_{21}NO_5PS$ 310.0878, found 310.0887 ([M+H]$^+$).

Alternate Synthesis of 2-n-hexyl-LKE-P

To octanoyl chloride (3.445 g, 21.18 mmol) in a round bottom flask, cooled by an external ice bath, was added trimethylphosphite (2.890 g, 23.29 mmol) at a rate to prevent boiling of the flask contents. Upon completion of the addition, the flask was purged with argon, covered, and allowed to stir at ambient temperature overnight (ca. 16 h). The chloromethane and excess trimethylphosphite were removed in vacuo and the resultant oil, under a blanket of argon(g), was added bromotrimethylsilane (11.18 mL, 84.72 mmol). The flask was purged with argon, covered, and allowed to stir at ambient temperature overnight (ca. 16 h). The solvent and excess bromotrimethylsilane were removed in vacuo. To the flask was added dichloromethane (10 mL) which was subsequently removed in vacuo to aid in the removal of any residual bromotrimethylsilane followed by the addition of dichloromethane (10 mL) and, to this solution, with stirring, was added a solution of bromine (2.17 mL, 42.36 mmol) in dichloromethane (5 mL). The flask was thoroughly purged with Ar(g) and the resultant solution was heated to reflux for one hour, under an argon atmosphere, followed by the removal of the solvent and excess bromine in vacuo. The residue was dissolved in 200 mL of 5% sodium bisulfite, stirred for 5 min, followed by the addition of a solution of cysteine ethyl ester, hydrochloride (3.933 g, 21.18 mmol) dissolved in 5% sodium bisulfite (10 mL). The flask was thoroughly purged with Ar(g) and the resultant solution was stirred for 12 h under a blanket of argon$_{(g)}$. The white solid was isolated by centrifugation, the supernatant was discarded, the precipitate was triturated with water and isolated by centrifugation (ca. 30 mL, 3×), and the residual solvent was removed in vacuo. The dry, solid, colored material was triturated with ethyl ether and isolated by centrifugation (ca. 30 mL, 3×) and the residual solvent was removed in vacuo to afford the product (2.105 g, 29.45% yield) as a white solid: $^1$H NMR (500 MHz, DMSO-$d_6$) δ=4.20-4.05 (m, 3H), 3.00 (dd, J=3.2, 12.3 Hz, 1H), 2.87 (dd, J=6.5, 12.1 Hz, 1H), 2.39-2.28 (m, 2H), 1.46-1.35 (m, 2H), 1.29-1.14 (m, 8H), 0.89-0.77 (m, 3H); $^{13}$C NMR (125 MHz, DMSO-$d_6$) δ 218.1 (d, $J_{C-P}$) 167.1 Hz), 175.6, 62.7, 38.3 (d, $J_{C-P}$) 51.1 Hz), 27.8, 14.0; $^{31}$P NMR (202 MHz, DMSO-$d_6$) δ 3.97; HRMS calcd for $C_{13}H_{25}NO_5PS$ 338.1191, found 338.1208 ([M+H]$^+$).

Synthesis of 2-n-hexyl-LK-P

To a solution of DiMethylOctanoylPhosphonate (DMOP) (1.076 g, 4.299 mmol), in a biotage microwave vial, was added bromotrimethylsilane (1.700 mL, 12.90 mmol). The tube was purged with argon, covered, and heated under microwave irradiation at 100° C. for 10 min. The contents of the vial were cooled to rt and transferred to a round bottom flask, the vial was washed with dichloromethane (3×3 mL) which was subsequently transferred to the flask. The solvent and excess bromotrimethylsilane were removed in vacuo. To the flask was added dichloromethane (10 mL) which was subsequently removed in vacuo to aid in the removal of any residual bromotrimethylsilane followed by the addition of dichloromethane (9 mL) and, to this solution, with stirring, was added a solution of bromine (440. μL, 8.60 mmol) in dichloromethane (3 mL). The flask was thoroughly purged with Ar(g) and the resultant solution was heated to reflux for 20 min, under an argon atmosphere, followed by the removal of the solvent and excess bromine in vacuo. The residue was dissolved in water, stirred for 5 min, followed by the addition of cysteine hydrochloride (755.1 mg, 4.299 mmol) dissolved in water (3 mL). The flask was thoroughly purged with Ar(g) and the resultant solution was stirred for 12 h under a blanket of argon$_{<g>}$). The white solid was isolated by centrifugation, the supernatant was discarded, the precipitate was triturated with water and isolated by centrifugation (ca. 30 mL, 3×), and the residual solvent was removed in vacuo. The dry, solid, colored material was triturated with ethyl ether and isolated by centrifugation (ca. 30 mL, 3×), and the residual solvent was removed in vacuo to afford the product (643.7 mg, 48.4% yield) as a white solid: $^1$H NMR (500 MHz, DMSO-d$_6$) δ=3.97 (d, J=5.7 Hz, 1H), 3.05 (d, J=11.7 Hz, 1H), 2.75 (dd, J=7.9, 12.0 Hz, 1H), 2.42-2.25 (m, 2H), 1.57-1.33 (m, 2H), 1.31-1.13 (m, 6H), 0.84 (t, J=6.6 Hz, 3H); $^{13}$C NMR (125 MHz, DMSO-d$_6$) δ 218.1 (d, JC-P) 167.1 Hz), 175.6, 62.7, 38.3 (d, J$_{C-P}$) 51.1 Hz), 27.8, 14.0; $^{31}$P NMR (202 MHz, DMSO-d$_6$) δ 3.97; HRMS calcd for C$_{11}$H$_{21}$NO$_5$PS 310.0878, found 310.0886 ([M+H]$^+$).

Synthesis of 2-methyl-LKE

To a solution of 2-oxobutanoic acid (494.6 mg, 4.845 mmol), in dichloromethane (6 mL), was added a solution of bromine (747.9 μL, 14.53 mmol) in dichloromethane (1.5 mL). The flask was thoroughly purged with Ar$_{(g)}$ and the resultant solution was heated to reflux for 30 min, under an argon atmosphere, followed by the removal of the solvent and excess bromine in vacuo. The residue was dissolved in water (4.5 mL), stirred for 1 min, followed by the addition of ethyl cysteine hydrochloride (901.2 mg, 4.854 mmol) dissolved in water (3 mL). The flask was thoroughly purged with Ar(g) and the resultant solution was stirred for 1 h under a blanket of argon$_{(g)}$. The white solid was isolated by centrifugation, the supernatant was discarded, the precipitate was triturated with water and isolated by vacuum filtration, and the residual solvent was removed in vacuo to afford the product (494.3 mg, 44.0% yield) as a white solid: $^1$H NMR (500 MHz, DMSO-d$_6$) δ=4.27 (dd, J=3.6, 4.9 Hz, 1H), 4.11 (q, J=6.9 Hz, 2H), 3.18-3.07 (m, 1H), 3.07-2.98 (m, 1H), 1.17 (t, J=7.1 Hz, 3H); $^{13}$C NMR (125 MHz, DMSO-d$_6$) δ 218.1 (d, JC-P) 167.1 Hz), 175.6, 62.7, 38.3 (d, J$_{C-P}$) 51.1 Hz), 27.8, 14.0; $^{31}$P NMR (202 MHz, DMSO-d$_6$) δ 3.97; HRMS calcd for C$_8$H$_{15}$NO$_5$PS 268.0409, found 268.0413 ([M+H]$^+$).

Synthesis of 2-ethyl-LKE

To a solution of 2-oxopentanoic acid (372.0 mg, 3.204 mmol), in dichloromethane (6 mL), was added a solution of bromine (247.5 μL, 9.611 mmol) in dichloromethane (1.5 mL). The flask was thoroughly purged with Ar$_{(g)}$ and the resultant solution was heated to reflux for 30 min, under an argon atmosphere, followed by the removal of the solvent and excess bromine in vacuo. The residue was dissolved in water (4.5 mL), stirred for 1 min, followed by the addition of ethyl cysteine hydrochloride (595.0 mg, 3.204 mmol) dissolved in water (3 mL). The flask was thoroughly purged with Ar(g) and the resultant solution was stirred for 1 h under a blanket of argon(g). The white solid was isolated by centrifugation, the supernatant was discarded, the precipitate was triturated with water and isolated by vacuum filtration, and the residual solvent was removed in vacuo to afford the product (303.4 mg, 47.5% yield) as a white solid: $^1$H NMR (500 MHz, Acetone-d$_6$) δ=4.24 (dd, J=3.2, 6.6 Hz, 1H), 4.19 (q, J=7.3 Hz, 2H), 3.24 (dd, J=3.3, 12.1 Hz, 1H), 3.07 (dd, J=6.5, 12.1 Hz, 1H), 2.57 (q, J=7.3 Hz, 2H), 1.24 (t, J=7.1 Hz, 3H), 1.09 (t, J=7.3 Hz, 3H); $^{13}$C NMR (125 MHz, DMSO-d$_6$) δ 218.1 (d, JC-P) 167.1 Hz), 175.6, 62.7, 38.3 (d, J$_{C-P}$) 51.1 Hz), 27.8, 14.0; $^{31}$P NMR (202 MHz, DMSO-d$_6$) δ 3.97; HRMS calcd for C$_8$H$_{15}$NO$_5$PS 268.0409, found 268.0413 ([M+H]$^+$).

Biological Activities Inherent to Phosphonate Substituted 5-Carboxy-1-Thia-4-Aza-2-Cyclohexenes and C2-Alkyl Substituted Derivatives Thereof Activation of Cellular Autophagy RG2 glioma cells (American Tissue Type Collection, ATTC, Rockville Md. USA) were treated for 4 h with 50 nM bafilomycin-A1 (previously dissolved to 1000× final concentration in dimethylsulfoxide). Thirty minutes after addition of bafilomycin, cells were treated with test agents at 100× final concentration. Cells were lysed in RIPA buffer containing protease and phosphatase inhibitors. Protein concentration was assayed and normalized to constant values (typically 5-7 mg/mL). Proteins were electrophoresed across 4-20% polyacrylamide gels and wet blotted onto polyvinylidine difluoride (PVDF) membranes. Proteins were blotted with commercially available antibodies against LC3.

As shown in FIGS. 8, 31-32, autophagy is substantially enhanced in RG2 glioma cells by a variety of C3-substituted LK-phosphonates bearing an alkyl group on C3. C2-alkyl substituted LKE also has substantial autophagy enhancing activity (FIGS. 32A-32B). In all cases, the relative LC3-II increase was greater or occurred at lower concentration than observed when RG2 cells were treated with unsubstituted LKE.

Figure 33:
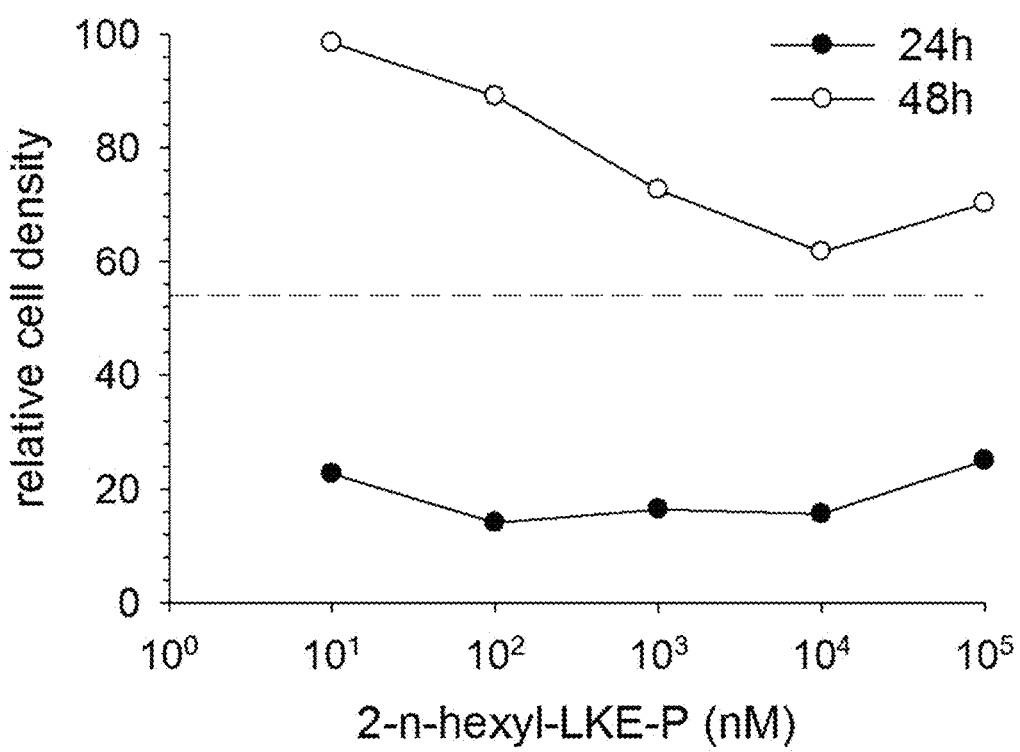
FIG. 33: Reduction in proliferative capacity of RG2 glioma cells exposed to 2-n-hexyl-LKE-P. Glioma cells were plated at low density and treated with the indicated concentration of compound for 24 or 48 h, at which time relative cell number was estimated using a tetrazolium reduction assay. At 24 h, cultures treated with greater than or equal to 1 nM of the test agent displayed at least 50% fewer cells (50% reduced replicative capacity) relative to cells treated with no drug (dashed line). By 48 h, the cell number had approximately doubled from the 24 h time point, but a dose-dependent reduction in the cell number was still observed in 2-n-hexyl-LKE-P treated cultures, with a minimum in the 1-10 mM range.

Reduction in Proliferative Capacity of Glioma Cells in Culture by C2-Alkyl Substituted, C3-LKE Phosphonates Biomarkers of autophagy have been positively correlated with relatively better prognosis (longer patient lifespan) in humans suffering from high grade glioma. Accordingly, phosphonate analogs were tested for ability to reduce replicative capacity in RG2 glioma cells wherein the compounds increase autophagy. Cells were plated at low density (approximately 25,000 cells/60 mm$^2$ dish) using general cell culture methods, and treated with logarithmic dilutions of test agent. After 24 or 48 hours, cell number was estimated by tetrazolium reduction assay using a commercially available kit (Promega Aqueous OneStep™). As shown in FIG. 33, cultures treated with 2-n-hexyl-LKE-P replicated more slowly in the first 24 h. By 48 h the cells had largely achieved confluence and became somewhat contact inhibited, thus reducing the difference between control and treatment groups.

The skilled person will recognize that a large variety and number of LKE, LK-P, LK-PE, LKE-P and LKE-PE compounds can be prepared while addressing the balance between structure, brain penetration probability, and activity, and still fall within the scope of the present disclosure.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound comprising Formula E:

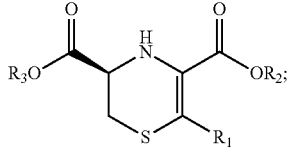

Formula E wherein:

R₁ is a substituted or unsubstituted alkyl, aryl, alkoxy, ester, alkenylamino, alkynylamino, aryloxy, aralkoxy, acyloxy, alkylamino, arylamino, aralkylamino, or amido group;

R₂ is hydrogen or substituted or unsubstituted alkyl, alkoxy, ester, alkenylamino, alkynylamino, aryloxy, aralkoxy, acyloxy, alkylamino, arylamino, aralkylamino, or amido; and R₃ is hydrogen or a substituted or unsubstituted alkyl, alkoxy, ester, alkenylamino, alkynylamino, aryloxy, aralkoxy, acyloxy, alkylamino, arylamino, aralkylamino, or amido;

and salts, stereoisomers, racemates, hydrates, solvates, polymorphs, and alkene reduction products thereof.

2. The compound of claim 1, wherein:

R₂ is selected from the group consisting of hydrogen, or heteroatom substituted or unsubstituted versions of $C_1$-$C_{15}$-alkoxy, $C_2$-$C_{15}$-alkenylamino, $C_2$-$C_{15}$-alkynylamino, $C_1$-$C_{15}$-aryloxy, $C_2$-$C_{15}$-aralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_1$-$C_{15}$-arylamino, $C_2$-$C_{15}$-aralkylamino, and $C_1$-$C_{15}$-amido; and R₃ is selected from the group consisting of heteroatom substituted or unsubstituted versions of $C_1$-$C_{15}$-alkoxy, $C_2$-$C_{15}$-alkenylamino, $C_2$-$C_{15}$-alkynylamino, $C_1$-$C_{15}$-aryloxy, $C_2$-$C_{15}$-aralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_1$-$C_{15}$-arylamino, $C_2$-$C_{15}$-aralkylamino, and $C_1$-$C_{15}$-amido.

3. The compound of claim 1, wherein the compound is 5-ethyl 2-methyl-LK:

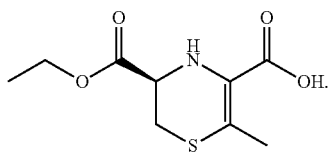

4. The compound of claim 1, wherein the compound is 5-methyl 2-ethyl-LK:

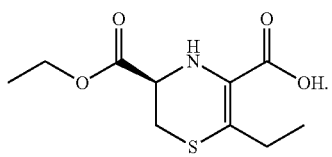 [SMILES: CCOC(=O)[C@@H]1CSC(CC)=C(C(=O)O)N1]

5. A compound comprising 2-isopropyl-AECK-P:

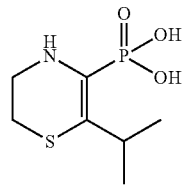

and salts, stereoisomers, racemates, hydrates, solvates, polymorphs, and alkene reduction products thereof.

6. A method of treating a glioma, the method comprising administering an effective amount of an 2-ethyl-LKE or a 2-n-hexyl-LKE-P compound of claim 1, to a subject in need thereof and treating the disorder;

wherein

"LKE" refers to a 5-ester of lanthionine ketamine compound, and "LKE-P" refers to a 5-ester of a lanthionine ketimine phosphonate compound.

7. A method of reducing damage to a cell resulting from cellular autophagy, the method comprising contacting a cell with an LK, LKE, 2 isopropyl-AECK-P, 2-n-butyl LK-P, or 2-isopropyl LK P, compound of claim 6, and reducing damage to the cell, wherein the cell is a neuron, macrophage, or glial cell;

wherein "LK" refers to lanthionine ketamine compound,

"LKE" refers to a 5-ester of lanthionine ketamine compound,

"LK-P" refers to a lanthionine ketimine phosphonate compound; and,

"2-isopropyl-AECK-P" refers to a compound having a structure of:

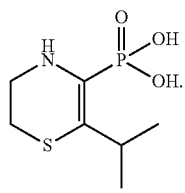

8. A method of making a compound of claim 1, the method comprising:

reacting an enolate of a carboxylic acid ester with a dialkyl oxalate to produce a 2-substituted-3-oxosuccinate diester;

hydrolyzing and decarboxylating the 2-substituted-3-oxosuccinate diester to produce an α-ketocarboxylic acid; and either (i) directly brominating the α-ketocarboxylic acid followed by reacting with a cysteine derivative to produce a 2-substituted lanthionine ketimine compound, or (ii) esterifying the α-ketocarboxylic acid to produce an α-ketoacid ester, and brominating the α-ketoacid ester followed by reacting with a cysteine derivative to produce a 2-substituted lanthionine ketimine compound.

9. The compound of claim 1, comprising 2-ethyl LK:

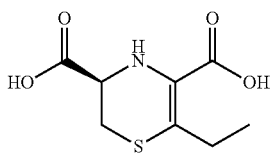

and salts, stereoisomers, racemates, hydrates, solvates, polymorphs, and alkene reduction products thereof.

10. The compound of claim 1, comprising 5-ethyl 2-isopropyl-LK:

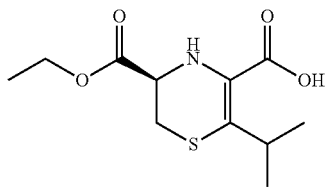 [SMILES: CCOC(=O)[C@@H]1CSC(C(C)C)=C(C(=O)O)N1]

and salts, stereoisomers, racemates, hydrates, solvates, polymorphs, and alkene reduction products thereof.

11. The compound of claim 1, comprising 5-ethyl 2-phenyl-LK:

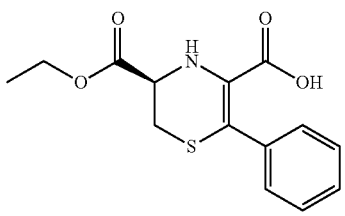 [SMILES: CCOC(=O)[C@@H]1CSC(c2ccccc2)=C(C(=O)O)N1]

and salts, stereoisomers, racemates, hydrates, solvates, polymorphs, and alkene reduction products thereof.

12. The compound of claim 1, comprising 3-methyl, 5-ethyl LK:

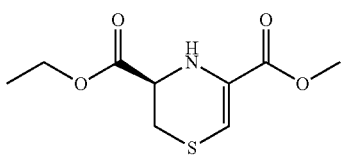

and salts, stereoisomers, racemates, hydrates, solvates, polymorphs, and alkene reduction products thereof.

13. The compound of claim 1, comprising 3-benzyl, 5-ethyl LK:

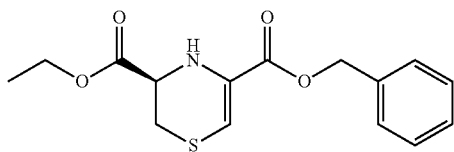 [SMILES: CCOC(=O)[C@@H]1CSC=C(C(=O)OCc2ccccc2)N1]

and salts, stereoisomers, racemates, hydrates, solvates, polymorphs, and alkene reduction products thereof.

14. The compound of claim 1, comprising 5-ethyl, 3-(3-triflouromethyl)benzyl LK:

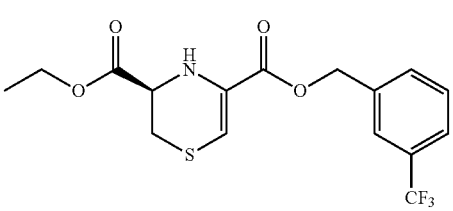 [SMILES: CCOC(=O)[C@@H]1CSC=C(C(=O)OCc2cccc(C(F)(F)F)c2)N1]

and salts, stereoisomers, racemates, hydrates, solvates, polymorphs, and alkene reduction products thereof.

15. The compound of claim 1, comprising 5-ethyl, 3-pivaloyloxymethyl LK:

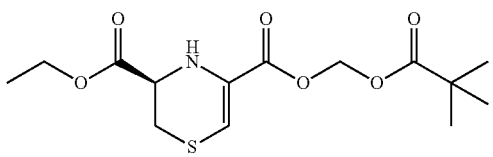 [SMILES: CCOC(=O)[C@@H]1CSC=C(C(=O)OCOC(=O)C(C)(C)C)N1]

and salts, stereoisomers, racemates, hydrates, solvates, polymorphs, and alkene reduction products thereof.

16. The compound of claim 1, comprising 5-ethyl, 3-octyl LK:

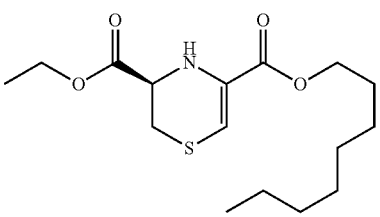 [SMILES: CCCCCCCCOC(=O)C1=CSC[C@@H](C(=O)OCC)N1]

and salts, stereoisomers, racemates, hydrates, solvates, polymorphs, and alkene reduction products thereof.

17. The compound of claim 1, comprising 5-methyl, 2-ethyl LK:

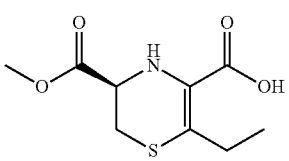

and salts, stereoisomers, racemates, hydrates, solvates, polymorphs, and alkene reduction products thereof.

18. The compound of claim 1, 3,5-dimethyl LK:

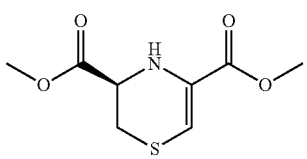

and salts, stereoisomers, racemates, hydrates, solvates, polymorphs, and alkene reduction products thereof.

19. The compound of claim 1, comprising 3,5-di(3-trifluoromethylbenzyl) LK:

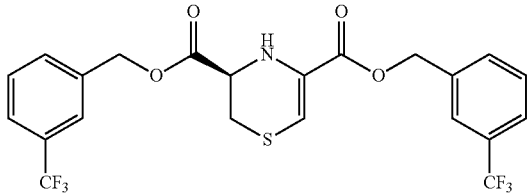 [SMILES: O=C(OCc1cccc(C(F)(F)F)c1)C1=CSC[C@@H](C(=O)OCc2cccc(C(F)(F)F)c2)N1]

and salts, stereoisomers, racemates, hydrates, solvates, polymorphs, and alkene reduction products thereof.

20. The compound of claim 1, comprising 3,5-dioctyl LK:

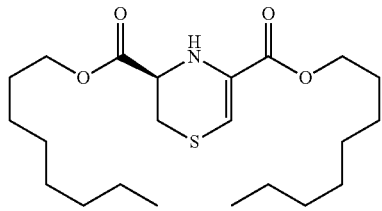 [SMILES: CCCCCCCCOC(=O)C1=CSC[C@@H](C(=O)OCCCCCCCC)N1]

and salts, stereoisomers, racemates, hydrates, solvates, polymorphs, and alkene reduction products thereof.

21. The compound of claim 1, comprising 5-ethyl 2-n-hexyl LK-P:

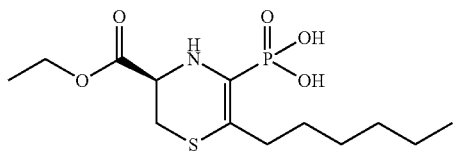 [SMILES: CCCCCCC1=C(P(=O)(O)O)N[C@H](C(=O)OCC)CS1]

and salts, stereoisomers, racemates, hydrates, solvates, polymorphs, and alkene reduction products thereof.

22. The compound of claim 1, comprising 5-ethyl 2-n-butyl LK-P:

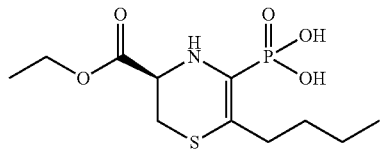 [SMILES: CCCCC1=C(P(=O)(O)O)N[C@H](C(=O)OCC)CS1]

and salts, stereoisomers, racemates, hydrates, solvates, polymorphs, and alkene reduction products thereof.

23. The compound of claim 1, comprising 5-ethyl 2-n-octyl LK-P:

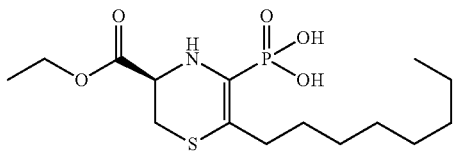 [SMILES: CCCCCCCCC1=C(P(=O)(O)O)N[C@H](C(=O)OCC)CS1]

and salts, stereoisomers, racemates, hydrates, solvates, polymorphs, and alkene reduction products thereof.

24. The compound of claim 1, comprising 2-isopropyl LK-P:

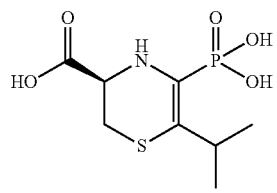 [SMILES: CC(C)C1=C(P(=O)(O)O)N[C@H](C(=O)O)CS1]

and salts, stereoisomers, racemates, hydrates, solvates, polymorphs, and alkene reduction products thereof.

25. The compound of claim 1, comprising 2-phenyl LK-P:

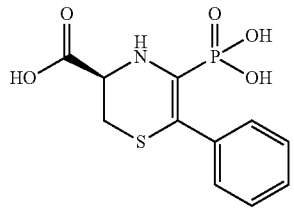 [SMILES: O=C(O)[C@@H]1CSC(c2ccccc2)=C(P(=O)(O)O)N1]

and salts, stereoisomers, racemates, hydrates, solvates, polymorphs, and alkene reduction products thereof.

26. The compound of claim 1, comprising 2-benzyl LK-P:

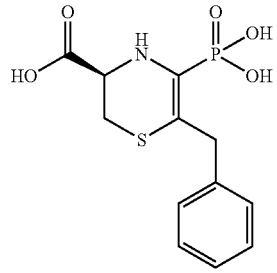 [SMILES: O=C(O)[C@@H]1CSC(Cc2ccccc2)=C(P(=O)(O)O)N1]

and salts, stereoisomers, racemates, hydrates, solvates, polymorphs, and alkene reduction products thereof.

27. The compound of claim 1, comprising 2-n-butyl LK-P:

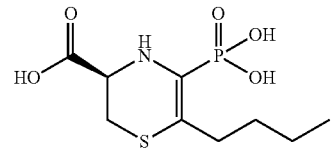 [SMILES: CCCCC1=C(P(=O)(O)O)N[C@H](C(=O)O)CS1]

and salts, stereoisomers, racemates, hydrates, solvates, polymorphs, and alkene reduction products thereof.

28. The compound of claim 1, comprising 2-n-hexyl LK-P:

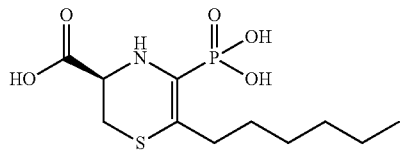 [SMILES: CCCCCCC1=C(P(=O)(O)O)N[C@H](C(=O)O)CS1]

and salts, stereoisomers, racemates, hydrates, solvates, polymorphs, and alkene reduction products thereof.

29. The compound of claim 1, comprising 3-ethyl 2-n-hexyl LK-P:

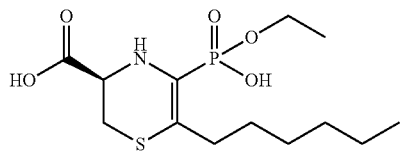 [SMILES: CCCCCCC1=C(P(=O)(O)OCC)N[C@H](C(=O)O)CS1]

and salts, stereoisomers, racemates, hydrates, solvates, polymorphs, and alkene reduction products thereof.

* * * * *

UNITED STATES PATENT AND TRADEMARK OFFICE
CERTIFICATE OF CORRECTION

Page 1 of 1

PATENT NO. : 10,882,831 B2
APPLICATION NO. : 16/487960
DATED : January 5, 2021
INVENTOR(S) : Kenneth Hensley and Travis Denton It is certified that error appears in the above-identified patent and that said Letters Patent is hereby corrected as shown below:

In the Claims

Column 54, Claim 7, Line 29 please correct:
"claim 6, and reducing"
To:
--claim 1, and reducing--

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*